(12) United States Patent
Slack

(10) Patent No.: US 8,039,233 B2
(45) Date of Patent: Oct. 18, 2011

(54) NUCLEIC ACID SEQUENCES AND THEIR USE IN METHODS TO IDENTIFY UMAMI MODULATIORS

(75) Inventor: Jay Patrick Slack, Loveland, OH (US)

(73) Assignee: Givaudan S.A. (CH)

(*) Notice: Subject to any disclaimer, the term of this patent is extended or adjusted under 35 U.S.C. 154(b) by 0 days.

(21) Appl. No.: 12/523,669

(22) PCT Filed: Dec. 14, 2007

(86) PCT No.: PCT/CH2007/000636
§ 371 (c)(1), (2), (4) Date: Jul. 28, 2009

(87) PCT Pub. No.: WO2008/086634
PCT Pub. Date: Jul. 24, 2008

(65) Prior Publication Data
US 2010/0015640 A1    Jan. 21, 2010

Related U.S. Application Data

(60) Provisional application No. 60/880,981, filed on Jan. 18, 2007.

(51) Int. Cl.
*C07K 14/705* (2006.01)
*C07K 19/00* (2006.01)
*C12N 15/62* (2006.01)

(52) U.S. Cl. ............. 435/69.7; 435/252.3; 435/320.1; 530/350; 536/23.4

(58) Field of Classification Search .............. None
See application file for complete search history.

(56) References Cited

U.S. PATENT DOCUMENTS

| | | |
|---|---|---|
| 4,115,538 A | 9/1978 | Satoh et al. |
| 5,401,629 A | 3/1995 | Harpold et al. |
| 5,436,128 A | 7/1995 | Harpold et al. |
| 5,462,856 A | 10/1995 | Lerner et al. |
| 5,919,649 A | 7/1999 | Habener et al. |
| 6,051,386 A | 4/2000 | Lerner et al. |
| 7,297,543 B2 | 11/2007 | Zoller et al. |
| 7,364,903 B2 | 4/2008 | Zoller et al. |
| 2003/0166137 A1 | 9/2003 | Zucker et al. |
| 2003/0232407 A1 | 12/2003 | Zoller et al. |
| 2004/0175792 A1 | 9/2004 | Zoller et al. |
| 2004/0175793 A1 | 9/2004 | Zoller et al. |
| 2005/0032158 A1 | 2/2005 | Adler et al. |
| 2006/0045953 A1 | 3/2006 | Tachdjian et al. |
| 2006/0275765 A1 | 12/2006 | Slack et al. |
| 2008/0085994 A1 | 4/2008 | Li et al. |

FOREIGN PATENT DOCUMENTS

| | | |
|---|---|---|
| WO | WO 92/01810 A1 | 2/1992 |
| WO | WO 01/18050 A2 | 3/2001 |
| WO | WO 03/004992 A2 | 1/2003 |
| WO | WO 2004/055048 A2 | 7/2004 |
| WO | WO 2005/015158 A2 | 2/2005 |
| WO | WO 2005/041684 A2 | 5/2005 |
| WO | WO 2007/147275 A1 | 12/2007 |

OTHER PUBLICATIONS

Broach, J.R. and J. Thorner "High-throughput screening for drug discovery", (1996) Nature 384 (supp.): 14-16).
Felley-Bosco et al., "Constitutive Expression of Inducible Nitric Oxide Synthase in Human Bronchial Epithelial Cells Induces c-*fos* and Stimulates the cGMP Pathway" Am. J. Resp. Cell and mol. Biol., (1994) 11:159-164.
Gijon et al., "Cytosolic Phospholipase $A_2$ Is Required for Macrophage Arachidonic Acid Release by Agonists That Do and Do Not Mobilize Calcium" 2000, J.Biol. Chem., 275:20146-20156.
Hafner, "Cytosensor Mircrophysiometer: technology and recent applications", 2000, Biosens. Bioelectron. 15: 149-158.
Horton & Baxendale, "Mass Measurements of Cyclic AMP Formation by Radioimmunoassay, Enzyme Immunoassay, and Scintillation Proximity Assay" 1995, Methods Mol. Biol. 41: Chap. 8, 91-105.
Kenimer & Nirenberg, "Desensitization of Adenylate Cyclase to Prostaglandin $E^1$ or 2-Chloroadenosine" 1981, Mol. Pharmacol. 20: 585-591.
Kikkawa et al., 1982, "Calcium-activated, Phospholipid-dependent Protein Kinase from Rat Brain"; Journal of Biological Chemistry; 257: 13341-13348.
Knight and Grigliatti, "Chimeric G Proteins Extend the Range of Insect Cell-Based Functional Assays for Human G Protein-Coupled Receptors" (2004) Journal of Receptors and Signal Transduction 24: 241-256.
Pinna & Ruzzene, "How do protein kinases recognize their substrates?" 1996, Biochem. Biophys. Acta 1314: 191-225.
Ryan, et al. "Biophysical Properties of the Extra-Cellular Domain of the Calcium-Sensing Receptor", Biochemical and Biophysical Research Communications, Oct. 13, 2006, pp. 339-344, vol. 349, No. 1, Academic Press, Inc., Orlando, Florida, US.
Traynor and Nahorski, "Modulation by µ-Opioid Agonists of Guanosine-5'-O-(3-[$^{35}$S]thio)triphosphate Binding to Membranes from Human Neuroblastoma SH-SY5Y Cells" 1995, Mol. Pharmacol. 47: 848-854.
Xu, H. et al., "Different Functional Roles of TiR Subunits in the Heteromeric Taste Receptors", Proceedings of the National Academy of Sciences of USA, Sep. 28, 2004, pp. 14258-14263, vol. 101, No. 39, National Academy of Science, Washington, D.C., US.

*Primary Examiner* — John Ulm
(74) *Attorney, Agent, or Firm* — Curatolo Sidoti Co., LPA; Joseph G. Curatolo; Salvatore A. Sidoti

(57) ABSTRACT

Novel chimeric proteins functional to screen for umami taste modulators, the corresponding nucleic acid sequences, expression vectors, transfected host cells, and screening methods for modulators and enhancers of the umami taste response employing the aforementioned are provided.

28 Claims, No Drawings

US 8,039,233 B2

NUCLEIC ACID SEQUENCES AND THEIR USE IN METHODS TO IDENTIFY UMAMI MODULATORS

CROSS REFERENCE TO RELATED APPLICATIONS

This application is a national stage application of International Application No. PCT/CH2007/000636, filed 14 Dec. 2007, which claims the benefit of U. S. Provisional Patent Application Ser. No. 60/880,981, filed 18 Jan. 2007, from which applications priority is claimed, and which are incorporated herein by reference.

Provided are novel nucleotides and proteins, constructs and cells containing them as well as methods employing these nucleotides, proteins, constructs and cells.

Umami taste is elicited by salts of glutamate and in particular monosodium glutamate (MSG) and other amino acids or salts thereof and is important for flavor attributes of savory foods. The umami taste is important for detecting the presence of amino acids in the diet, which are critical to the nutritional health of humans. However, a part of the general human population can be adversely affected by added MSG in processed foods and would therefore prefer umami tastants that are non-MSG or non-amino acid in nature. Currently, the umami taste of glutamate can be enhanced by the addition of the naturally occurring purine nucleotides, IMP and GMP, but these are difficult to purify or are expensive to produce, thus limiting their widespread use. Less expensive umami modulators and in particular umami tastants or their enhancers that could be used as substitutes for glutamate, IMP or GMP would be useful in the commercial food applications. Of particular interest are umami tastants or their enhancers that can be used at very low concentrations to reduce costs as well as minimize any potential adverse effects on health.

Known screens for umami modulators including umami tastants (agonists of the umami receptor), umami enhancers and umami inhibitors employ the wildtype T1R1/T1R3 heterodimeric umami receptor. Functional assays based on the T1R1/T1R3 umami taste receptor heteromeric dimer are described, for example, in US20040175793.

However, a disadvantage of known screens is that the wildtype T1R1/T1R3 receptor comprises several binding domains, in particular the extracellular amino terminal domains including the venus flytrap domain (VFT) that binds to glutamate, MSG, amino acids and potentially other umami tastants. Therefore, a screen for specific modulators of specific ligands, and in particular for ligands of the transmembrane domains ("TMD(s)") of T1R1 and/or T1R3 and excluding the VFT ligands, including but not limited to MSG, is not possible with known screening methods. Use of the known T1R1/T1R3 heterodimer would allow for identification of agents that also bind in the VFT that may compete for binding with glutamate and could thus identify agents that may later prove ineffective as umami enhancers in food applications.

Accordingly, there remains a need for an alternative screening method that avoids the above problems and in particular avoids the identification of agents that may compete with glutamate for binding to the receptor, and allows to identify umami receptor modulators (incl. agonists, enhancers, inhibitors) that bind at a site physically distinct from the VFT domains, and in particular in the TMD.

The screening methods and binding assays that are provided avoid the above problems and allow for improved results by using the novel CSR::T1R chimeric proteins.

Further, the CSR::T1R chimeric protein as described herein allows the use of calcium as a ligand/agonist for receptor activation instead of umami tastants such as glutamate/MSG, allowing for identification of modulators (incl. agonists, enhancers, inhibitors) that bind outside of the MSG binding site.

SUMMARY

In a first aspect, provided is a CSR::T1R chimeric protein able to bind to at least one compound selected from umami modulator including umami tastant, umami tastant enhancer, and umami tastant inhibitor, comprising one or more CSR::T1R selected from:
 a CSR::T1R1 polypeptide substantially homologous to SEQ ID NO:2 with a sequence identity of at least 90%, and
 a CSR::T1R3 polypeptide substantially homologous to SEQ ID NO:4 with a sequence identity of at least 90%.

Such CSR::T1R chimeric proteins able to bind to at least one compound selected from umami modulator including umami tastant, umami tastant enhancer, and umami tastant inhibitor are in particular a CSR::T1R1 homomeric chimeric protein, a CSR::T1R1/CSR::T1R3 heterodimeric chimeric protein, a CSR::T1R1/T1R3 heterodimeric chimeric protein, and a T1R1/CSR::T1R3 heterodimeric chimeric protein.

In another aspect, provided is a CSR::T1R chimeric protein as defined herein-above comprising
 two polypeptide subunits in the form of a heterodimeric protein selected from the group consisting of
  a CSR::T1R1/CSR::T1R3 heterodimeric chimeric protein,
  a CSR::T1R1/T1R3 heterodimeric chimeric protein, and
  a T1R1/CSR::T1R3 heterodimeric chimeric protein,
 wherein the T1R1 subunit of the heterodimer comprises a polypeptide essentially homologous to SEQ ID NO:8 with a sequence identity of at least 90%; and
 wherein the T1R3 subunit of the heterodimer comprises a polypeptide essentially homologous to SEQ ID NO:10 with a sequence identity of at least 90%.

In another aspect, provided is a CSR::T1R chimeric protein as defined herein-above which is a CSR::T1R1 homomeric chimeric protein.

In another aspect, provided is a CSR::T1R chimeric protein comprising two polypeptide subunits as defined herein-above which is the CSR::T1R1/CSR::T1R3 heterodimeric chimeric protein.

In another aspect, provided is a nucleic acid encoding a CSR::T1R chimeric protein able to bind at least one compound selected from umami modulator including umami tastant, umami tastant enhancer, and umami tastant inhibitor, comprising one or more of
 a nucleic acid substantially homologous to a nucleotide sequence selected from the group consisting of SEQ ID NO:1 (CSR::T1R1) and SEQ ID NO:3 (CSR::T1R3) as determined by sequence identity,
 a nucleic acid substantially homologous to a nucleotide sequence selected from the group consisting of SEQ ID NO:1 (CSR::T1R1) and SEQ ID NO:3 (CSR::T1R3) as determined by hybridisation,
 a nucleic acid substantially homologous to a nucleotide sequence encoding the CSR::T1R chimeric protein as defined herein-above,
 wherein the substantially homologous nucleic acid as determined by sequence identity has a sequence identity of at least 90%;
 wherein the substantially homologous nucleic acid as determined by hybridisation hybridises under stringent hybridization conditions at a temperature of 42° C. in a solution consisting of 50% formamide, 5×SSC, and 1% SDS, and washing at 65° C. in a solution consisting of 0.2×SSC and 0.1% SDS;

wherein the nucleic acid optionally comprises SEQ ID NO:6 (HSV tag) at or near its end to form the C-terminus in the corresponding protein.

In another aspect, provided is a nucleic acid encoding a CSR::T1R1 chimeric protein able to bind at least one compound selected from umami modulator including umami tastant, umami tastant enhancer, and umami tastant inhibitor, comprising one or more of a nucleic acid substantially homologous to the nucleotide sequence of SEQ ID NO:1 (CSR::T1R1) as determined by sequence identity, a nucleic acid substantially homologous to of the nucleotide sequence of SEQ ID NO:1 (CSR::T1R1) as determined by hybridisation, a nucleic acid substantially homologous to a nucleotide sequence encoding the CSR::T1R1 chimeric protein as defined in claim 1, wherein the substantially homologous nucleic acid as determined by sequence identity has a sequence identity of at least 90%;

wherein the substantially homologous nucleic acid as determined by hybridisation hybridises under stringent hybridization conditions at a temperature of 42° C. in a solution consisting of 50% formamide, 5×SSC, and 1% SDS, and washing at 65° C. in a solution consisting of 0.2×SSC and 0.1% SDS;

wherein the nucleic acid optionally comprises SEQ ID NO:6 (HSV tag) at or near its end to form the C-terminus in the corresponding protein.

In another aspect, provided is an expression vector comprising the nucleic acid as defined herein-above.

In another aspect, provided is a host cell transfected with an expression vector as defined in herein-above.

In another aspect, provided is a host cell as described herein-above stably expressing a CSR::T1R chimeric protein as defined herein-above and a G-Protein, optionally a G-Protein substantially homologous to Gaq-Gustducin.

In another aspect, provided is a host cell as described herein-above, transiently expressing a CSR::T1R chimeric protein as described herein-above and a G-Protein, optionally a G-Protein substantially homologous to Gaq-Gustducin.

In another aspect, provided is a method of producing a CSR::T1R chimeric protein as defined herein-above, comprising the step of culturing host cells comprising an expression vector encoding for the CSR::T1R chimeric protein, under conditions sufficient for expression, thereby forming the CSR::T1R chimeric protein and optionally recovering it from the cells.

In another aspect, provided is a method to identify an agent that modulates umami taste signaling in taste cells, the method comprising the steps of:
(i) contacting the cells that express a CSR::T1R chimeric protein that responds to stimuli selected from umami taste stimuli and calcium stimuli with an agent thereby providing a functional response, optionally in presence of another agent; and
(ii) determining whether at least one agent affects the functional response of said CSR::T1R chimeric protein in said cells by at least one functional response in said cells; wherein said CSR::T1R chimeric protein is as defined herein-above.

In another aspect, provided is a method as defined herein-above wherein the cells also express a G-Protein.

In another aspect, provided is a method as defined herein-above wherein the G-Protein is a chimeric G-protein substantially homologous to Gaq-Gustducin.

In another aspect, provided is a method as defined herein-above wherein the G-Protein is the chimeric G-protein G alpha 16-gustducin 44.

In another aspect, provided is a method as defined herein-above wherein step (ii) is performed by measuring a change in or caused by intracellular messengers.

In another aspect, provided is a method as defined herein-above wherein the functional response is determined by measuring a change in an intracellular messenger selected from IP3 and calcium$^{2+}$.

In another aspect, provided is a method as defined herein-above wherein said cells are selected from the group consisting of bacterial cells, eucaryotic cells, yeast cells, insect cells, mammalian cells, amphibian cells, worm cells, and combinations thereof.

In another aspect, provided is a method as described herein-above, wherein the cell is a mammalian cell.

In another aspect, provided is a method as described herein-above wherein the cell is a mammalian cell selected from the group consisting of CHO, COS, HeLa, HEK-293 cells, and combinations thereof.

In another aspect, provided is a method as described herein-above, wherein step (i) further comprises contacting the CSR::T1R chimeric protein with a test agent in presence of calcium.

In another aspect, provided is a method as described herein-above, wherein the calcium is provided in the form of calcium chloride.

In another aspect, provided is a kit comprising
(i) recombinant cells that express a CSR::T1R chimeric protein as defined herein-above, and
(ii) an agonist of the CSR::T1R chimeric protein, for combined use to identify test agents as modulators of the CSR::T1R chimeric protein.

In another aspect, provided is a method of using the kit as defined herein-above, comprising:
(i) growing recombinant cells that express the CSR::T1R chimeric protein,
(ii) adding test agents in the presence of the agonist in a suitable concentration, and
(iii) determining a change in a functional response of the cells by comparing the response in presence and absence of the test agent, and the test agent is thereby identified as a modulator of the CSR::T1R chimeric protein as defined herein-above.

The test agents may be added in a suitable concentration, for example from about 1 nM to 100 mM or more.

In another aspect, provided is a method to identify an agent that modulates the CSR::T1R chimeric protein as defined herein-above, the method comprising the steps of:
(i) measuring a parameter that changes in response to a ligand binding to the CSR::T1R chimeric protein, and
(ii) determining a change of the parameter in response to a test agent, optionally in presence of a ligand, in comparison to a negative control and thereby identifying a modulator including a ligand.

In another aspect, provided is a method as defined herein-above wherein the ligand is selected from the group consisting of calcium, calcium ions, calcium chloride and combinations thereof.

In another aspect, provided is a method as defined herein-above, wherein step (i) is performed by a method selected from the group consisting of fluorescence spectroscopy, NMR spectroscopy, measuring of one or more of absorbance, refractive index, hydrodynamic methods, chromatography, measuring solubility, biochemical methods, wherein the methods measure the properties of the CSR::T1R chimeric protein in a suitable environment selected from the group consisting of solution, bilayer membrane, attached to a solid phase, in a lipid monolayer, bound on a membrane, and in vesicles.

DETAILED DESCRIPTION

The term CSR::T1R or CSR::T1R chimeric protein, as used herein, designates the CSR::T1R1 homomer (i.e. in absence of any T1R3); or the heterodimeric complex of CSR::T1R1 with CSR::T1R3 or with the wildtype T1R3 (CSR::T1R1/CSR::T1R3 or CSR::T1R1/T1R3); or the heterodimeric complex of CSR::T1R3 with CSR::T1R1 or with the wildtype T1R1 (CSR::T1R1/CSR::T1R3 or T1R1/CSR::T1R3).

More generally, as the receptor is coupled to a G-Protein in vivo and in many in vitro methods, CSR::T1R is also referred to as "the GPCR".

By "homomer"/"homomeric" is meant the relevant subunit without the other subunit, i.e. either T1R1 without T1R3, or T1R3 without T1R1—while it is believed that each subunit probably forms a homomer/homo-oligomer, this is not necessarily the case, for example, it may act as a monomer.

Similarly, by "heterodimer" is meant the two relevant subunits in combination, i.e. T1R1 with T1R3, in any form—while an actual heterodimer may be formed, this is not necessarily the case, for example, the receptor may act in form of a hetero-oligomer comprising a complex wherein the two subunits are present in more than one copy.

Chimeric proteins are joined fragments of two or more original proteins that sometimes are able to combine desired properties or eliminate unwanted ones. As the folding of a protein in the three dimensional space is critical and the position of amino acids will influence the folding, not any two fragments can be joined. Even if critical domains and amino acids are known, the successful expression, correct folding and intact functionality of desired properties is very much unpredictable. For example, applicant has found that various GABA::T1R chimeric protein variants did not work.

The novel chimeric homomers CSR::T1R1 and CSR::T1R3, were found to be functional and are able to form a functional CSR::T1R1/CSR::T1R3 heterodimer providing a functional response.

A "functional response" means that the CSR::T1R is able to bind directly or indirectly (for example via an accessory protein) to a modulator (for example an agonist, antagonist, ligand, enhancer or inhibitor) and show modulation by said modulator (for example activation by said ligand) of the natural cellular response to the umami receptor or the respective in vitro or in vivo surrogate of said response. This will naturally depend on the method used. In the examples this is the change in the calcium signal, in other methods this might be an activated map kinase signal or arrestin translocation or receptor internalisation. The determination of a functional response includes the determination of any change in parameter including physiological, physical and chemical parameter. Such parameters that may be measured depend on the method chosen and include, for example radioactivity, fluorescence, enzyme-activity, changes in ion flux, membrane potential, current flow, transcription, concentrations, in particular second messenger concentrations (e.g., cAMP, cGMP, IP3, or intracellular calcium), change in neurotransmitter or hormone release. A functional response can be measured by any suitable means known to those skilled in the art, for example changes in spectroscopic characteristics (e.g., fluorescence, absorbency, refractive index), hydrodynamic (e.g., shape), chromatographic, or solubility properties, patch clamping, voltage-sensitive dyes, whole cell currents, radioisotope efflux, inducible markers, oocyte gene expression; tissue culture cell gene expression; transcriptional activation of genes; ligand-binding assays; voltage, membrane potential and conductance changes; ion flux assays; changes in intracellular second messengers such as cAMP, cGMP, and inositol triphosphate (IP3); changes in intracellular calcium levels; neurotransmitter release, conformational assays.

Further examples of functional responses and how to measure them are included in the methods described herein-below.

Experiments of the applicant indicate that the CSR::T1R1 homomeric subunit also functions as a functional umami receptor on its own, without forming a heterodimer.

Preliminary experiments indicate that while the homomeric CSR::T1R3 subunit may have difficulties in engaging and/or activating certain G-proteins; CSR::T1R3 is still useful in binding assays that do not require the ability to activate a G-Protein. Heterodimers that include a chimeric protein coexpressed with a wildtype protein (CSR::T1R1/T1R3 and T1R1/CSR::T1R3) may also work.

In the CSR::T1R1/CSR::T1R3 heterodimer, each of the CSR::T1R subunits of the heterodimeric complex comprises a sequence that stems from two source proteins. The two source proteins are the human calcium-sensing receptor (hCaSR), and a T1R protein (T1R1 or T1R3). The hCaSR-derived fragment (CSR) common to both subunits comprises the extracellular domain (ECD) of hCaSR. The T1R-derived fragments comprise the transmembrane domains (TMD) of the T1R sequences and differ, as they are derived from either T1R1 or T1R3.

A CSR::T1R chimeric protein as described herein does not possess the VFT domains of either T1R1, or of T1R3, or of both T1R1 and T1R3, and therefore allows to specifically identify compounds (umami modulators including umami tastants, umami tastant enhancers and umami tastant inhibitors) that bind to the TMD domains and/or the cysteine-rich domains of T1R1 and/or T1R3.

These umami modulators are of particular interest as they do not include compounds that compete with amino acids or their salts such as MSG that are believed to bind in the VFT site of the umami taste receptor, and the screen employing CSR::T1R will therefore tend to identify the more interesting potentially synergistic compounds.

The novel chimeric CSR::T1R constructs that are provided (DNA, vectors, transfected cells, proteins) are useful when screening, without limitation, for modulators of the umami taste response (including umami agonists, umami enhancers, and umami inhibitors) Traditional screening methods and binding assays may be used to screen with the novel chimeric CSR::T1R proteins for modulators and enhancers. Such screening methodology is well-known in the art, and is outlined herein below. To identify an umami tastant, a signal linked with the binding and/or activation of the CSR::T1R receptor proteins as described herein is monitored in presence and absence of the candidate umami tastant.

To identify or characterise an umami enhancer or inhibitor, usually the results of samples with and without potential enhancer/inhibitor, both samples additionally containing one or more of calcium, glutamate, MSG or another umami tastant, for example another amino acid (to bind and activate the receptor), are compared.

Using calcium (for example, without limitation, in the form of calcium chloride) instead of a ligand like, for example, MSG, has the additional advantage of avoiding any negative effects/artifacts (for example due to high salt) or competition between of the actual ligand/agonist (MSG) and the test compound.

Cells Used in the Assays:

Transfected or endogenous T1R3 and T1R1 can negatively interfere with methods that determine agonist responses of CSR::T1R1 and/or CSR::T1R3, respectively, or the change of said responses dependent on another modulator. The absence of T1R3 and T1R1 provides a null background for the determination of CSR::T1R1 and/or CSR::T1R3 activation, so that observed signals can be directly attributed to CSR::T1R1 and/or CSR::T1R3 activity. This allows the identification of agents that specifically modulate CSR::T1R1 and/or CSR:: T1R3, and excludes agents that activate the wildtype T1R1 and T1R3, which could in the case of T1R3 also include sweet tastants, as T1R3 is part of both the sweet and the umami heterodimers.

The presence of the endogenous wildtype T1R1 and/or T1R3 will cause some backgrounds signals, which are undesirable. While cells with endogenous T1R1 and/or T1R3 can still be useful to obtain results with sufficiently low background, a better choice are cells that do not contain the endogenous T1R1 and T1R3 receptors. An exception occurs when using a CSR::T1R1/T1R3 chimeric protein, which may contain wildtype T1R3 without adverse effect on the background, or a T1R1/CSR::T1R3 chimeric protein, which may contain wildtype T1R1 without adverse effects on the background.

The cells listed below are particularly useful as they do not contain endogenous/wildtype T1R3, or endogenous wildtype T1R1. However, alternative cells are also useful in the methods described herein.

Suitable eucaryotic cells include eucaryotic cells, for example, without limitation, mammalian cells, yeast cells, or insect cells (including Sf9), amphibian cells (including melanophore cells), or worm cells including cells of *Caenorhabditis* (including *Caenorhabditis elegans*).

Suitable mammalian cells include, for example, without limitation, COS cells (including Cos-1 and Cos-7), CHO cells, HEK293 cells, HEK293T cells, HEK293 T-Rex™ cells, or other transfectable eucaryotic cell lines.

Suitable bacterial cells include without limitation *E. coli*.

Cells may be transfected with a GPCR and a G-protein (which links the receptor to a phospholipase C signal transduction pathway) transiently or stably, as is well known in the art. An excellent heterologous expression system that employs the chimeric G-protein G alpha 16-gustducin 44 (also known as G.sub.alpha.16 gust(ducin)44, G.sub.alpha.16gust(ducin)44, Gα16gust(ducin)44, Ga16gust(ducin)44, Gα16-gustducin 44, or as used hereinbelow, "G16gust44") which provides for enhanced coupling to taste GPCRs, is described in detail in WO 2004/055048. Alternatively, other chimeric G-proteins based on Gaq-Gustducin described in WO 2004/055048, or other G-Proteins, for example, G16 or G15, may also be used.

The CSR::T1R can be expressed in a cell with a G-protein that links the receptor to a signal transduction pathway, for example, the phospholipase C signal transduction pathway, or signal transduction pathways including, for example, the following: adenylate cyclase, guanylate cyclase, phospholipase C, IP3, GTPase/GTP binding, arachnoid acid, cAMP/cGMP, DAG, protein kinase c (PKC), MAP kinase tyrosine kinase, or ERK kinase.

Alternatively, any suitable reporter gene may be linked to a CSR::T1R-activation responsive promoter and used to determine CSR::T1R activity, as described in more detail hereinbelow.

Vector Constructs Used in Cells Described Herein-Above:

The vector constructs for expressing the GPCR and/or the G-protein in such cells may be produced in a manner known per se using Polymerase Chain Reactions. After verification of the sequence, cDNA fragments may be sub-cloned into a suitable vector, for example pcDNA 3.1 mammalian expression vector for mammalian cells, and transiently transfected in a corresponding host cell to enable the correct expression of the gene.

After a post-transfection period, for example 48 hours, cell lysates may be prepared, analysed by a Western-Blot analysis in order to confirm the correct expression of the protein. Once correct protein expression is confirmed, suitable cells, for example mammalian cells including HEK293T cells and HEK T-Rex™, may be transfected to generate cells stably expressing the protein according to techniques well known in the art.

Alternatively, a variety of non-mammalian expression vector/host systems can be used to contain and express sequences encoding the CSR::T1R G-Protein coupled receptor (GPCR). These include, for example, microorganisms including bacteria transformed with recombinant bacteriophage, plasmid, or cosmid DNA expression vectors; yeast transformed with yeast expression vectors; insect cell systems infected with viral expression vectors (for example baculovirus), or with bacterial expression vectors (for example pBR322 plasmids).

Examples of specific vectors that may be used with the systems described herein-above are described in "G-protein coupled receptors (Signal Transduction Series)"; Editors: Tatsuya Haga and Gabriel Berstein, 1st ed., CRC Press—Boca Raton Fla.; September 1999.

In bacterial systems, a number of cloning and expression vectors may be selected depending upon the use intended for polynucleotide sequences encoding the GPCR. For example, routine cloning, subcloning, and propagation of polynucleotide sequences encoding a GPCR can be achieved using a multifunctional *E. coli* vector such as pBLUESCRIPT (Stratagene, La Jolla Calif.) or pSPORT1 plasmid (Life Technologies). Ligation of sequences encoding a GPCR into the vector's multiple cloning site disrupts the lacZ gene, allowing a calorimetric screening procedure for identification of transformed bacteria containing recombinant molecules. In addition, these vectors may be useful for in vitro transcription, dideoxy sequencing, single strand rescue with helper phage, and creation of nested deletions in the cloned sequence. When large quantities of a GPCR are needed, for example, for the production of antibodies, vectors which direct high level expression of a GPCR may be used. For example, vectors containing the strong, inducible SP6 or T7 bacteriophage promoter may be used.

Yeast expression systems may be used for production of a GPCR. A number of vectors containing constitutive or inducible promoters, such as alpha factor, alcohol oxidase, and PGH promoters, may be used in the yeast *Saccharomyces cerevisiae* or *Pichia pastoris*. In addition, such vectors direct either the secretion or intracellular retention of expressed proteins and enable integration of foreign sequences into the host genome for stable propagation.

For the expression of heterologous proteins in insect cell lines is, for example, derivatives of the Lepidopteran baculovirus, *Autographa californica* multicapsid nucleo-virus (AcMNPV) can be used. In this system, foreign gene expression is directed by a very strong late viral promoter, either the polyhedrin or p10 promoters, and a wide array of vectors is available that optimises expression and recovery of recombinant proteins. These vectors enable expression of both membrane-bound and secreted proteins at high levels, and also many post-translational modifications known to occur in mammalian systems, including N- and O-linked glycosylation, phosphorylation, acylation, proteolysis and secreted vaccine components. A number of vectors are commercially available, for example the InsectSelect™ System from Invitrogen.

Expression Systems:

In order to express cDNAs encoding the desired proteins (GPCR (CSR::T1R) and G-protein), one typically subclones the appropriate cDNA into an expression vector that contains a strong promoter to direct transcription, a transcription/translation terminator, and a ribosome-binding site for translational initiation. Suitable bacterial promoters are well known in the art, for example, E. coli, Bacillus sp., and Salmonella, and kits for such expression systems are commercially available. Similarly, eukaryotic expression systems for mammalian cells, yeast, and insect cells are commercially available. The eukaryotic expression vector may be, for example, an adenoviral vector, an adeno-associated vector, or a retroviral vector.

In addition to the promoter, the expression vector typically contains a transcription unit or expression cassette that contains all the additional elements required for the expression of the protein-encoding nucleic acid in host cells. A typical expression cassette thus contains a promoter operably linked to the nucleic acid sequence encoding the protein and signals required for efficient polyadenylation of the transcript, ribosome binding sites, and translation termination. The nucleic acid sequence encoding the protein may typically be linked to a membrane-targeting signal such as the N-terminal 45 amino acids of the rat Somatostatin-3 receptor sequence to promote efficient cell-surface expression of the recombinant protein, which is useful for cell-surface receptors. Additional elements may include, for example, enhancers.

An expression cassette should also contain a transcription termination region downstream of the structural gene to provide for efficient termination. The termination region may be obtained from the same gene as the promoter sequence or may be obtained from different genes.

For expression of the proteins, conventional vectors for expression in eucaryotic or procaryotic cells well known in the art may be used. Examples of vectors include bacterial expression vectors, for example, plasmids including pBR322-based plasmids, pSKF, and pET23D, and fusion expression systems, for example, GST and LacZ.

Expression vectors containing regulatory elements from eukaryotic viruses are typically used in eukaryotic expression vectors, for example SV40 vectors, cytomegalovirus vectors, papilloma virus vectors, and vectors derived from Epstein-Barr virus. Other exemplary eukaryotic vectors include pMSG, pAV009/A+, pMTO10/A+, pMAMneo-5, baculovirus pDSVE, pcDNA3.1, pIRES and any other vector allowing expression of proteins under the direction of the SV40 early promoter, SV40 later promoter, metallothionein promoter, murine mammary tumor virus promoter, Rous sarcoma virus promoter, polyhedrin promoter, or other promoters shown effective for expression in eukaryotic cells.

Some expression systems have markers that provide gene amplification such as thymidine kinase, hygromycin B phosphotransferase, dihydrofolate reductase and the like.

The elements that are typically included in expression vectors may also include a replicon that functions in E. coli, a gene encoding drug resistance to permit selection of bacteria that harbor recombinant plasmids, and unique restriction sites in non-essential regions of the plasmid to allow insertion of eukaryotic sequences. The particular drug resistance gene chosen is not critical, any of the many drug resistance genes known in the art are suitable. The prokaryotic sequences are optionally chosen such that they do not interfere with the replication of the DNA in eukaryotic cells, if necessary.

In bacterial systems the GPCR cDNA fragment may be expressed alone or as a fusion protein wherein the GPCR of interest is fused to the E. coli periplasmic maltose-binding protein (MBP) wherein the MBP, including its signal peptide, is linked to the amino terminus of the GPCR. The wild-type GPCR cDNA or the MBP:GPCR fusion cDNA is subcloned into a suitable plasmid, for example pBR322, where in E. coli, GPCR expression is driven by the lac wild-type promoter. Methods of expression of GPCRs in E. coli are described, for example, in "G-protein coupled receptors (Signal Transduction Series)"; Editors: Tatsuya Haga and Gabriel Berstein, 1st ed., pp. 265-280 CRC Press—Boca Raton Fla.; September 1999.

Genetically engineered yeast systems and insect cell systems which lack endogenous GPCRs provide the advantage of a null background for CSR::T1R activation screening.

Genetically engineered yeast systems substitute a human GPCR and Gα protein for the corresponding components of the endogenous yeast pheromone receptor pathway. Downstream signaling pathways are also modified so that the normal yeast response to the signal is converted to positive growth on selective media or to reporter gene expression (described by Broach, J. R. and J. Thorner (1996) Nature 384 (supp.):14-16).

Genetically engineered insect systems incorporate a human GPCR and Gα protein that enables receptor coupling the phospholipase C signaling pathway (see for example Knight and Grigliatti, (2004) J Receptors and Signal Transduction 24: 241-256).

Amphibian cell systems, in particular melanophore cells, are described, for example, in WO 92/01810 that describes a GPCR expression system.

Overexpression of CSR::T1R:

CSR::T1R may be overexpressed by placing it under the control of a strong constitutive promoter, for example the CMV early promoter. Alternatively, certain mutations of conserved GPCR amino acids or amino acid domains can be introduced to render the employed GPCR constitutively active.

Alternatively, overexpression may be achieved under control of an inducible promoter such as the T-rex system described herein below.

Transfection of CSR::T1R Expression Vector Constructs into Cells:

Standard transfection methods can be used to produce bacterial, mammalian, yeast or insect cell lines that express large quantities of the protein.

Any known method for introducing nucleotide sequences into host cells may be used. It is only necessary that the particular genetic engineering procedure used be capable of successfully introducing the relevant genes into the host cell capable of expressing the proteins of interest. These methods may involve introducing cloned genomic DNA, cDNA, synthetic DNA or other foreign genetic material into a host cell and include the use of calcium phosphate transfection, polybrene, protoplast fusion, electroporation, liposomes, microinjection, plasma vectors, viral vectors and the like.

For example, without limitation, the T-Rex™ expression system (Invitrogen Corp., Carlsbad, Calif.) may be used. The T-Rex™ System is a tetracycline-regulated mammalian expression system that uses regulatory elements from the *E. coli* Tn10-encoded tetracycline (Tet) resistance operon. Tetracycline regulation in the T-Rex™ System is based on the binding of tetracycline to the Tet repressor and derepression of the promoter controlling expression of the gene of interest.

Cell Culture:

After transfection, the transfected cells may be cultured using standard culturing conditions well known in the art. It will be apparent to the skilled person that different cells require different culture conditions including appropriate temperature and cell culture media.

CSR::T1R Receptor Protein Recovery:

If desired, the protein may be recovered from the cell culture using standard techniques. For example, the cells may be burst open either mechanically or by osmotic shock before being subject to precipitation and chromatography steps, the nature and sequence of which will depend on the particular recombinant material to be recovered.

Alternatively, the recombinant protein may be recovered from the culture medium in which the recombinant cells had been cultured.

Modulators that May be Identified by the Assays:

Modulators (various types including ligands, agonists, partial agonists, antagonists, inverse agonists, inhibitors, enhancers) of CSR::T1R receptor activity can be identified as described herein below.

The type of a modulator may include more than one type at a time, and may depend on the concentration. For example, an agent may act as an agonist in a certain concentration range, but act as a modulator or enhancer of another agonist (for example a umami tastant) in another concentration range. Therefore, agents should be tested at different concentrations to identify them as modulators.

There now follows a definition of the agents to be identified in the methods described herein.

A modulator is an agent that effects an increase or decrease of one or more of the following: the cell surface expression of a receptor, the binding of a ligand to a receptor, the intracellular response initiated by an active form of the receptor (either in the presence or absence or an agonist). The modulator can itself be an agonist that binds to the receptor, activates it and thereby modulates an increase in the cellular response.

Modulators include various types of compounds, including small molecules, peptides, proteins, nucleic acids, antibodies or fragments thereof. These can be derived from various sources including synthetic or natural, extracts of natural material, for example from animal, mammalian, insect, plant, bacterial or fungal cell material or cultured cells, or conditioned medium of such cells.

A ligand is an agent that binds to the receptor; it may be an agonist, partial agonist, enhancer, antagonist, or inverse agonist.

An agonist is a ligand of the CSR::T1R chimeric protein receptor that activates the receptor and increases an intracellular response when it binds to a receptor compared to the intracellular response in the absence of the agonist. Additionally or alternatively, an agonist may decrease internalization of a cell surface receptor such that the cell surface expression of a receptor is increased as compared to the number of cell surface receptors present on the surface of a cell in the absence of an agonist.

Agonists of CSR::T1R include, for example, calcium and N-(2-Methoxy-4-methyl-benzyl)-N'-(2-pyridin-2-yl-ethyl)-oxalamide.

A ligand of the CSR::T1R chimeric protein can be divided into two types, a CSR-domain-ligand which binds in the CSR part of the chimeric protein (calcium), or a T1R-domain ligand, which binds in the T1R-part of the chimeric protein (modulators of the umami taste response).

A partial agonist is an agonist that only partially activates the receptor in comparison to other agonists that maximally activate the receptor.

An antagonist is a ligand which binds to the receptor at the same (competitive antagonist) or at a different site (allosteric antagonist) as an agonist, but does not activate an intracellular response initiated by an active form of a receptor, thereby inhibiting the intracellular response induced by an agonist as compared to the intracellular response in the presence of an agonist and in the absence of an antagonist.

An inverse agonist, binding to a receptor, decreases the constitutive intracellular response mediated by a receptor as compared to the intracellular response in the absence of the inverse agonist.

An inhibitor decreases the binding of an agonist to the receptor as compared to the binding of the agonist in the absence of inhibitor, and/or decreases the intracellular response induced by an agonist.

An enhancer increases the binding of an agonist to the receptor as compared to the binding of the agonist in the absence of enhancer, and/or increases the intracellular response induced by an agonist.

The activity, or changes in activity, of a receptor binding a ligand and transmitting the signal through, for example, a G-protein (i.e. due to different interactions with modulators) can be determined by the assays described herein-below.

Assays to Identify Modulators of the CSR::T1R Receptor:

Modulators can be identified using a wide variety of in vitro and in vivo assays to determine and compare functional effects/parameters, or alternatively by binding assays. The effects of the test agents upon the function of the receptors can be measured by examining suitable functional parameters. Any physiological change that affects receptor activity can be used to identify modulators.

Such functional assays are well-known in the art, for example assays using intact cells or tissues isolated from animals based on measuring the concentration or activity or their change of a secondary messenger (including, for example, intracellular calcium ($Ca2+$), cAMP, cGMP, inositol phosphate (IP3), diacylglycerol/DAG, arachnoid acid, MAP kinase or tyrosine kinase), ion flux, phosphorylation levels, transcription levels, neurotransmitter levels, and assays based on GTP-binding, GTPase, adenylate cyclase, phospholipid-breakdown, diacylglycerol, inositol triphosphate, arachidonic acid release, PKC, kinase and transcriptional reporters. Some suitable assays are, for example, described in WO 01 18050.

Receptor activation typically initiates subsequent intracellular events, for example, increases in second messengers, for example, IP3, which releases intracellular stores of calcium ions. Activation of some G-protein coupled receptors stimulates the formation of inositol triphosphate (IP3) through phospholipase C-mediated hydrolysis of phosphatidylinositol. IP3 in turn stimulates the release of intracellular calcium ion stores. Thus, a change in cytoplasmic calcium ion levels, or a change in second messenger levels such as IP3 can be used to determine G-protein coupled receptor activity.

All functional assays may be performed by samples containing cells expressing the receptor on their surfaces or on isolated cell membrane fractions. Useful cells are described herein-above. Instead of samples with separate cells or cell membranes, tissues from transgenic animals may be used.

The screening methods described herein are particularly useful to identify modulators of the umami taste response, for example, umami enhancers.

To identify a modulator which is not an agonist itself (e.g. an antagonist, partial agonist, inverse agonist, inhibitor, or enhancer), samples with and without test agent both containing an agonist are compared. As agonist, for example, calcium can be used. Using calcium has the advantage that both TMDs will be accessible. Other known or identified agonists can also be used, for example, N-(2-Methoxy-4-methyl-benzyl)-N'-(2-pyridin-2-yl-ethyl)-oxalamide, but will partially occupy ligand/agonist binding sites which may coincide with the modulator binding site of the to-be identified modulator, and may cause lower signals. For example, a control (with agonist but without modulator) is assigned a relative receptor activity value of 100. A decrease in activity relative to the control identifies an inhibitor, antagonist or inverse agonist, an increase identifies an enhancer. Usually, an increase or decrease in the measured activity of 10% or more in a sample with test agent compared to a sample without test agent or compared to a sample with test agent but based on cells that do not express CSR::T1R (mock-transfected cells) can be considered significant.

To identify an umami enhancer, samples with and without test agent are compared. For example, a control (with agonist, for example calcium chloride, but without modulator) is assigned a relative receptor activity value of 100. An increase identifies an enhancer. Usually, an increase or decrease in the measured activity of 10% or more in a sample with test agent compared to a sample without test agent or compared to a sample with test agent but based on cells that do not express CSR::T1R (mock-transfected cells) can be considered significant.

For screens that employ the CSR::T1R chimeric protein, calcium can be used as agonist. Alternatively, agonists binding in the relevant parts of the T1R1 and/or T1R3 fragments of CSR::T1R may be used. These agonists include, for example, N-(2-Methoxy-4-methyl-benzyl)-N'-(2-pyridin-2-yl-ethyl)-oxalamide, Cas No. 745047-97-6; which is a known synthetic agonist of the hT1R1/hT1R3 wildtype umami receptor. The compound and its preparation is described in WO2005041684 and in related US2006045953 (example 132).

Identification of Agonists or Partial Agonists:

To identify an agonist or partial agonist that does not bind in the VFT domains, a sample with test agent is compared to a positive control with an agonist (for example calcium chloride, N-(2-Methoxy-4-methyl-benzyl)-N'-(2-pyridin-2-yl-ethyl)-oxalamide, or another identified ligand/agonist).

Alternatively/additionally, samples with and without test agent are compared in their activity of the CSR::T1R chimeric protein.

For example, an agonist or partial agonist will have a biological activity corresponding to at least 10% of the maximal biological activity of the positive control umami agonist when the agonist or partial agonist is present at 100 mM or less, for example it may have a maximal biological activity comparable to the agonist or higher. Maximal biological activity is defined as the maximal achievable receptor response to an agonist, for example calcium chloride or N-(2-Methoxy-4-methyl-benzyl)-N'-(2-pyridin-2-yl-ethyl)-oxalamide that can be achieved within a given receptor assay format and this response fails to increase further despite application of increasing concentrations of that same agonist.

The above-mentioned agonists may, at a different concentration, also act as an enhancer of an agonist of the CSR::T1R chimeric protein. This may be tested in a screening method by using calcium or other agonist to test the agonist-test agent for signals indicating an umami enhancing effect.

Alternatively, an increase in the measured activity of, for example, 10% or more in a sample with test agent is compared to a sample without test agent or is compared to a sample with test agent but based on cells that do not express CSR::T1R (mock-transfected cells).

To identify antagonists, receptor activity in the presence of a known agonist with and without a test agent is compared. Antagonists show a reduction of agonist-stimulated receptor activity, for example by at least 10%.

To identify inverse agonists, receptor activity in the presence of a known agonist with and without a test agent is compared in samples comprising animals/cells/membranes that overexpress the receptor as described herein-above. Inverse agonists show a reduction of constitutive activity of the receptor, for example by at least 10%.

Various examples of suitable detection methods that measure CSR::T1R receptor activity in assays described herein-above follow.

Many screens rely on calcium activity, and for these a buffer system low in calcium should be used to avoid unspecific stimulation of cells, receptor, enzyme or reporter genes)

Detection of Changes of Cytoplasmic Ions or Membrane Voltage:

Cells are loaded with ion sensitive dyes to report receptor activity, as described in detail in "G-protein coupled receptors (Signal Transduction Series)", CRC Press 1999; 1st Edition; Eds Haga and Berstein. Changes in the concentration of ions in the cytoplasm or membrane voltage are measured using an ion sensitive or membrane voltage fluorescent indicator, respectively.

Calcium Flux:

Intracellular calcium release induced by the activation of GPCRs is detected using cell-permeant dyes that bind to calcium. The calcium-bound dyes generate a fluorescence signal that is proportional to the rise in intracellular calcium. The methods allows for rapid and quantitative measurement of receptor activity.

Cells used are transfected cells that co-express the CSR::T1R GPCR and a G-protein which allows for coupling to the phospholipase C pathway as described herein-above. Negative controls include cells or their membranes not expressing CSR::T1R (mock transfected), to exclude possible non-specific effects of the candidate compound.

The calcium flux detection protocol is described in detail in "G-protein coupled receptors (Signal Transduction Series)"; Editors: Tatsuya Haga and Gabriel Berstein, 1st ed., 424 pp. CRC Press—Boca Raton Fla.; September 1999, and an adapted version with is summarised below:

Day 0: 96-well plates are seeded with 8.5K cells per well and maintained at 37° C. overnight in nutritive growth media.

Day 1: Cells are transfected using 150 ng total of GPCR DNA and 0.3 µl of Lipofectamine 2000 (Invitrogen) per well. Transfected cells are maintained at 37° C. overnight in nutritive growth media.

Day 2: Growth media is discarded and cells are incubated for 1 hour (at room temperature in the dark) with 50 µl of calcium assay solution consisting of 1.5 µM Fluo-4 AM (Molecular Probes) and 2.5 µM probenicid dissolved in a reduced calcium C1 buffer solution which contains 130 mM NaCl, 5 mM KCl, 10 mM Hepes, 0.5 mM CaCl2 and 10 mM glucose (pH 7.4) at 37° C. 125 µl of the reduced calcium C1 buffer is added to each well and the plate is further incubated for 30 minutes at room temperature in the dark. Buffer solutions are discarded and plate is washed 5 times with 100 μl reduced calcium C1 buffer as a washing buffer and cells are reconstituted in 200 μl of reduced calcium C1 buffer.

Then the plate is placed in a fluorescent microplate reader, for example, the Flexstation (Molecular Devices) or the FLIPR (Molecular Devices) and receptor activation is initiated following addition of 20 μl of a 10× concentrated ligand stock solution. Fluorescence is continuously monitored for 15 seconds prior to ligand addition and for 45-110 seconds after ligand addition. Receptor activation levels are defined as by the three following equations: % Activation=(Maximum fluorescence−baseline fluorescence/baseline fluorescence) *100 or Fluorescence Increase=Maximum Fluorescence−baseline fluorescence, where baseline fluorescence represents the average fluorescence levels prior to ligand addition; or by determining the increase in peak fluorescence (F) normalized to the baseline fluorescence ($F_0$). The data are normalized using the following equation: $\Delta F/F=(F-F_0)/F_0$, where F is the peak fluorescence signal and $F_0$ is the baseline fluorescence signal, wherein the baseline fluorescence represents the mean fluorescence calculated for the first 10 to 15 seconds prior to ligand addition.

Useful cells are, without limitation, mammalian cells as described herein-above, for example HEK293T cells and HEK293 T-Rex™ cells. Cells may be transfected with a GPCR and a G-Protein transiently or stably as is well known in the art. An excellent heterologous expression system is described in detail in WO 2004/055048.

A calcium flux assay can be performed, for example, as described in example 1 herein-below.

The identification of a modulator is performed as described above subject to the following modifications. The signals are compared to the baseline level of CSR::T1R activity obtained from recombinant cells expressing CSR::T1R in the presence of an agonist but in the absence of a test agent. An increase or decrease in CSR::T1R activity, for example of at least 2 fold, at least 5 fold, at least 10 fold, at least a 100 fold, or more identifies a modulator.

Alternatively, the identification involves an increase or decrease fluorescence intensity of, for example, 10% or more, when compared to a sample without modulator, or when compared to a sample with modulator but in cells that do not express the CSR::T1R polypeptide (mock-transfected cells).

Adenylate Cyclase Activity:

Assays for adenylate cyclase activity are performed, for example, as described in detail by Kenimer & Nirenberg, 1981, Mol. Pharmacol. 20: 585-591. Reaction mixtures are incubated usually at 37° C. for less than 10 minutes. Following incubation, reaction mixtures are deproteinized by the addition of 0.9 ml of cold 6% trichloroacetic acid. Tubes are centrifuged and each supernatant solution is added to a Dowex AG50W-X4 column. The cAMP fraction from the column is eluted with 4 ml of 0.1 mM imidazole-HCl (pH 7.5) into a counting vial in order to measure the levels of cAMP generated following receptor activation by the agonist. Control reactions should also be performed using protein homogenate from cells that do not express a CSR::T1R polypeptide.

IP3/$Ca^{2+}$ Signals:

In cells expressing G-proteins, signals corresponding to inositol triphosphate (IP3)/$Ca^{2+}$ and thereby receptor activity can be detected using fluorescence. Cells expressing a GPCR may exhibit increased cytoplasmic calcium levels as a result of contribution from both intracellular stores and via activation of ion channels, in which case it may be desirable, although not necessary, to conduct such assays in calcium-free buffer, optionally supplemented with a chelating agent such as EDTA, to distinguish fluorescence response resulting from calcium release from internal stores.

Phospholipase C/Intracellular $Ca^{2+}$ Signals:

CSR::T1R is expressed in a cell with a G-protein that links the receptor to a phospholipase C signal transduction pathway. Changes in intracellular $Ca^{2+}$ concentration are measured, for example using fluorescent $Ca^{2+}$ indicator dyes and/or fluorometric imaging.

GTPase/GTP Binding:

For a GPCR including CSR::T1R, a measure of receptor activity is the binding of GTP by cell membranes containing the GPCR. Measured is the G-protein coupling to membranes by detecting the binding of labeled GTP.

Membranes isolated from cells expressing the receptor are incubated in a buffer containing 35S-GTPγS and unlabeled GDP. Active GTPase releases the label as inorganic phosphate, which is detected by separation of free inorganic phosphate in a 5% suspension of activated charcoal in 20 mM $H_3PO_4$, followed by scintillation counting.

The mixture is incubated and unbound labeled GTP is removed by filtration onto GF/B filters. Bound and labeled GTP is measured by liquid scintillation counting. Controls include assays using membranes isolated from cells not expressing CSR::T1R (mock-transfected), in order to exclude possible non-specific effects of the test agent. The method is described in detail by Traynor and Nahorski, 1995, Mol. Pharmacol. 47: 848-854.

To identify modulators, as described herein-above, a change (increase or decrease) of 10% or more in GTP binding or GTPase activity is usually sufficient. However, to identify agonists, the assays described herein-above are performed subject to the following modifications. An agent is identified as an agonist usually if the activity is at least 50% of that of a known agonist (for example N-(2-Methoxy-4-methyl-benzyl)-N'-(2-pyridin-2-yl-ethyl)-oxalamide) when the compound is present at 100 mM or less, for example 10 to 500 μM, for example about 100 μM, or if it will induce a level the same as or higher than that induced by a known agonist.

Microphysiometer or Biosensor:

Such assays can be performed as described in detail in Hafner, 2000, Biosens. Bioelectron. 15: 149-158.

Arachinoid Acid:

The intracellular level of arachinoid acid is employed as an indicator of receptor activity. Such a method is described in detail by Gijon et al., 2000, J. Biol. Chem., 275:20146-20156.

cAMP/cGMP:

Intracellular or extracellular cAMP is measured using a cAMP radioimmunoassay (RIA) or cAMP binding protein, for example as described by Horton & Baxendale, 1995, Methods Mol. Biol. 41: 91-105. Alternatively, a number of kits for the measurement of cAMP are commercially available, for example the High Efficiency Fluorescence Polarization-based homogeneous assay by LJL Biosystems and NEN Life Science Products. Alternatively, the intracellular or extracellular levels of cGMP may measured using an immunoassay. For example, the method described in Felley-Bosco et al., Am. J. Resp. Cell and Mol. Biol., 11:159-164 (1994), may be used to determine the level of cGMP. Alternatively an assay kit for measuring cAMP and/or cGMP as described in U.S. Pat. No. 4,115,538 can be used.

Negative controls with mock-transfected cells or extracts thereof to exclude possible non-specific effects of test agents may be used.

DAG/IP3:

Second messengers Diacylglycerol (DAG) and/or inositol triphosphate (IP3), which are released by Phospholipid breakdown, that is caused by receptor activity, can be detected and used as an indicator of GPCR (CSR::T1R) activity, for example as described in Phospholipid Signalling Protocols, edited by Ian M. Bird, Totowa, N.J., Humana Press, 1998. Alternatively, kits for the measurement of inositol triphosphates are available commercially from Perkin Elmer and CisBio International.

Negative controls with mock-transfected cells or extracts thereof to exclude possible non-specific effects of test agents may be used.

PKC Activity:

Growth factor receptor tyrosine kinases can signal via a pathway involving activation of Protein Kinase C (PKC), which is a family of phospholipid- and calcium-activated protein kinases.

Increases in gene products induced by PKC show PKC activation and thereby receptor activity. These gene products include, for example, proto-oncogene transcription factor-encoding genes (including c-fos, c-myc and c-jun), proteases, protease inhibitors (including collagenase type I and plasminogen activator inhibitor), and adhesion molecules (including intracellular adhesion molecule I (ICAM I)).

PKC activity may be directly measured as described by Kikkawa et al., 1982, J. Biol. Chem. 257: 13341, where the phosphorylation of a PKC substrate peptide, which is subsequently separated by binding to phosphocellulose paper, is measured. It can be used to measure activity of purified kinase, or in crude cellular extracts. Protein kinase C sample can be diluted in 20 mM HEPES/2 mM DTT immediately prior to the assay.

An alternative assay can be performed using the Protein Kinase C Assay Kit commercially available by PanVera.

The above-described PKC assays are performed on extracts from cells expressing the GPCR (CSR::T1R).

Alternatively, activity can be measured through the use of reporter gene constructs driven by the control sequences of genes activated by PKC activation.

Negative controls with mock-transfected cells or extracts thereof to exclude possible non-specific effects of test agents may be used.

MAP Kinase Activity:

MAP kinase activity can be measured using commercially available kits, for example, the p38 MAP Kinase assay kit by New England Biolabs, or the FlashPlate™ MAP Kinase assays by Perkin-Elmer Life Sciences. p42/44 MAP kinases or ERK1/2 can be measured to show GPCR (CSR::T1R) activity when cells with Gq and Gi coupled GPCRs are used, and an ERK1/2 assay kit is commercially available by TGR Biosciences, which measures the phosphorylation of endogenous ERK1/2 kinases following GPCR activation.

Alternatively, direct measurements of tyrosine kinase activity through known synthetic or natural tyrosine kinase substrates and labeled phosphate are well known; the activity of other types of kinases (for example, Serine/Threonine kinases) can be measured similarly.

All kinase assays can be performed with both purified kinases and crude extracts prepared from cells expressing one or more CSR::T1R polypeptide.

The substrates of kinases that are used can be either full-length protein or synthetic peptides representing the substrate. Pinna & Ruzzene (1996, Biochem. Biophys. Acta 1314: 191-225) lists a number of phosphorylation substrate sites useful for detecting kinase activities. A number of kinase substrate peptides are commercially available. One that is particularly useful is the "Src-related peptide," (commercially available from Sigma), which is a substrate for many receptor and nonreceptor tyrosine kinases. Some methods require the binding of peptide substrates to filters, then the peptide substrates should have a net positive charge to facilitate binding. Generally, peptide substrates should have at least 2 basic residues and a free-amino terminus. Reactions generally use a peptide concentration of 0.7-1.5 mM.

Negative controls with mock-transfected cells or extracts thereof to exclude possible non-specific effects of test agents may be used.

Transcriptional Reporters/CSR::T1R-Responsive Promoter/Reporter Gene:

To identify modulators with reporter gene assays, an at least 2-fold increase or 10% decrease in the signal is significant. An agonist stimulates for example at least 2-fold, 5-fold, 10-fold or more when comparing activity in presence and absence of the test agent.

The intracellular signal initiated by binding of an agonist to CSR::T1R sets in motion a cascade of intracellular events, the ultimate consequence of which is a rapid and detectable change in the transcription or translation of one or more genes.

The activity of the receptor can therefore be determined by measuring the expression of a reporter gene driven by a promoter responsive to CSR::T1R activation.

A "promoter" as used herein is one or more transcriptional control elements or sequences necessary for receptor-mediated regulation of gene expression, including one or more of basal promoter, enhancers and transcription-factor binding sites necessary for receptor-regulated expression. Promoters responsive to the intracellular signals resulting from agonist binding to CSR::T1R are selected and operatively linked to a corresponding promoter-controlled reporter gene whose transcription, translation or ultimate activity is readily detectable and measurable.

Reporter genes may be selected, for example, from luciferase, CAT, GFP, β-lactamase, β-galactosidase, and the so-called "immediate early" genes, c-fos proto-oncogene, transcription factor CREB, vasoactive intestinal peptide (VIP) gene, the somatostatin gene, the proenkephalin gene, the phosphoenolpyruvate carboxy-kinase (PEPCK) gene, genes responsive to NF-κB, and AP-1-responsive genes (including the genes for Fos and Jun, Fos-related antigens (Fra) 1 and 2, IκBα, ornithine decarboxylase, and annexins I and II).

Promoters will be selected according to the selected reporter gene, as will be apparent to the skilled person.

Luciferase, CAT, GFP, β-lactamase, β-galactosidase and assays for the detection of their products are well known in the art. Examples of further reporter genes are described herein-below.

The "immediate early" genes are suitable and are rapidly induced (for example within minutes of contact between the receptor and the effector protein or ligand). Desirable properties in reporter genes include one or more of the following: rapid responsiveness to ligand binding, low or undetectable expression in quiescent cells; induction that is transient and independent of new protein synthesis; subsequent shut-off of transcription requires new protein synthesis; and mRNAs transcribed from these genes which have a short half-life of several minutes to a few hours. Similarly, the promoter may have one, several or all of these properties.

The c-fos proto-oncogene is an example of a gene that is responsive to a number of different stimuli and has an rapid induction. The c-fos regulatory elements include a TATA box that is required for transcription initiation; two upstream elements for basal transcription, and an enhancer, which includes an element with dyad symmetry and which is required for induction by TPA, serum, EGF, and PMA. The 20 bp c-fos transcriptional enhancer element located between −317 and −298 bp upstream from the c-fos mRNA cap site, is essential for serum induction in serum starved NIH 3T3 cells. One of the two upstream elements is located at −63 to −57 and it resembles the consensus sequence for cAMP regulation.

The transcription factor CREB (cyclic AMP responsive element binding protein) is responsive to levels of intracellular cAMP. Therefore, the activation of a receptor that signals via modulation of cAMP levels can be determined by detecting either the binding of the transcription factor, or the expression of a reporter gene linked to a CREB-binding element (termed the CRE, or cAMP response element). The DNA sequence of the CRE is TGACGTCA. Reporter constructs responsive to CREB binding activity are described in U.S. Pat. No. 5,919,649.

Other suitable reporter genes and their promoters include the vasoactive intestinal peptide (VIP) gene and its promoter which is cAMP responsive; the somatostatin gene and its promoter which is cAMP responsive; the proenkephalin and its promoter which is responsive to cAMP, nicotinic agonists, and phorbol esters; and the phosphoenolpyruvate carboxykinase (PEPCK) gene and its promoter which is cAMP responsive.

Additional examples of reporter genes and their promoters that are responsive to changes in GPCR activity include the AP-1 transcription factor and NF-κB.

The AP-1 promoter is characterised by a consensus AP-1 binding site which is the palindrome TGA(C/G)TCA. The AP-1 site is also responsible for mediating induction by tumor promoters including the phorbol ester 12-O-tetradecanoylphorbol-β-acetate (TPA), and are therefore sometimes also referred to as a TRE, for TPA-response element. AP-1 activates numerous genes that are involved in the early response of cells to growth stimuli. Examples of AP-1-responsive genes include the genes for Fos and Jun (which proteins themselves make up AP-1 activity), Fos-related antigens (Fra) 1 and 2, IκBα, ornithine decarboxylase, and annexins I and II.

A large number of genes have been identified as NF-κB responsive, and their control elements can be linked to a reporter gene to monitor GPCR activity. Genes responsive to NF-κB include for example those encoding IL-1~, TNF-a, CCR5, P-selection, Fas ligand, GM-CSF and IKBa. Vectors encoding NF-KB-responsive reporters are known in the art or can be readily formed using ordinary skill in the art, for example, synthetic NFKB elements and a minimal promoter, or using the NF-KB-responsive sequences of a gene known to be subject to NF-KB regulation. Further, NF-KB responsive reporter constructs are commercially available from, for example, CLONTECH.

A given promoter construct can easily be tested by exposing GPCR (CSR::T1R)-expressing cells, transfected with the construct, to an agonist (for example N-(2-Methoxy-4-methyl-benzyl)-N'-(2-pyridin-2-yl-ethyl)-oxalamide). An increase of at least 2-fold in the expression of reporter gene in response to the agonist indicates that the reporter is suitable to measure GPCR (CSR::T1R) activity.

Controls for transcription assays include both cells not expressing GPCR (CSR::T1R), but carrying the reporter construct, and cells with a promoterless reporter construct.

Agents that modulate GPCR (CSR::T1R) activity as shown by reporter gene activation can be verified by using other promoters and/or other receptors to verify GPCR (CSR::T1R) specificity of the signal and determine the spectrum of their activity, thereby excluding any non-specific signals, for example non-specific signals via the reporter gene pathway.

Inositol Phosphates (IP) Measurement:

Phosphatidyl inositol (PI) hydrolysis may be determined as described in U.S. Pat. No. 5,436,128, which involves labelling of cells with 3H-myoinositol for at least 48 hours or more. The labeled cells are contacted with a test agent for one hour, then these cells are lysed and extracted in chloroformmethanol-water. This is followed by separating the inositol phosphates by ion exchange chromatography and quantifying them by scintillation counting. For agonists, fold stimulation is determined by calculating the ratio of counts per minute (cpm) in the presence of tested agent, to cpm in the presence of buffer control. Likewise, for inhibitors, antagonists and inverse agonists, fold inhibition is determined by calculating the ratio of cpm in the presence of test agent, to cpm in the presence of buffer control (which may or may not contain an agonist).

Binding Assays:

Alternatively to the functional assays described hereinabove that measure a change in parameters caused by a functional response to ligand binding, ligand binding may be determined by binding assays that measure the binding of a ligand to a CSR::T1R receptor.

Binding assays are well known in the art and can be tested in solution, in a bilayer membrane, optionally attached to a solid phase, in a lipid monolayer, or in vesicles. Binding of a modulator to a CSR::T1R polypeptide can be determined, for example, by measuring changes in spectroscopic characteristics (for example fluorescence, absorbance, or refractive index), hydrodynamic methods (employing for example shape), chromatography, measuring solubility properties of a CSR::T1R polypeptide. In one embodiment, binding assays are biochemical and use membrane extracts from cells/tissue expressing recombinant CSR::T1R polypeptides.

A binding assay may, for example, be performed as described for T1Rs by Adler et al. in US20050032158, paragraphs [0169] to [0198].

CSR::T1R Receptor Polypeptide and Nucleic Acid, and Substantially Homologous Polypeptides and Nucleic Acids:

The CSR::T1R chimeric proteins useful in methods described herein may be selected from the group consisting of the polypeptide selected from SEQ ID NO:2, SEQ ID NO:4, the chimeric heterodimer of SEQ ID NO: 2 and SEQ ID NO:4, a heterodimer of SEQ ID NO:2 with wildtype T1R3, and a heterodimer of SEQ ID NO: 4 with wildtype T1R1. Alternatively, the CSR::T1R chimeric proteins (or nucleic acid encoding the CSR::T1R) may be a receptor (or nucleotide sequence to form such a CSR::T1R receptor) which is substantially homologous and remains functional (i.e. binds to ligands and/or is activated by ligands, or encodes such a receptor).

A substantially homologous CSR::T1R chimeric protein includes such proteins where the T1R1 or T1R3 part is replaced with the relevant part of an allelic variant or different species, including T1R1 and/or T1R3 from mouse, rat, hamster, ape, and dog.

Further, substantially homologous CSR::T1R nucleotide or polypeptide sequences may be formed by conservative mutations and/or point mutations and include any conservatively modified variant as detailed below.

With respect to nucleic acid sequences, conservatively modified variants means nucleic acids which encode identical or essentially identical amino acid sequences (conservatively substituted amino acids, i.e. lysine switched to arginine and further examples as explained herein-below).

Because of the degeneracy of the genetic code, a large number of nucleic acids different in sequence but functionally identical encode any given polypeptide/protein. Such nucleic acid variations are "silent variations," which are one species of conservatively modified variations. Each nucleic acid sequence which encodes a polypeptide also describes every possible silent variation of the nucleic acid. Therefore, each codon in a nucleic acid (except AUG, which is ordinarily the only codon for methionine, and TGG, which is ordinarily the only codon for tryptophan) can be modified to yield a functionally identical nucleic acid sequence that will produce an identical polypeptide. Accordingly, each silent variation of a nucleic acid which encodes a polypeptide is implicit in each given nucleic acid sequence.

With respect to amino acid sequences, amino acid substitutions may be introduced using known protocols of recombinant gene technology including PCR, gene cloning, site-directed mutagenesis of cDNA, transfection of host cells, and in-vitro transcription which may be used to introduce such changes to the CSR::T1R sequence. The variants can then be screened for taste-cell-specific GPCR functional activity. Conservative substitution tables providing functionally similar amino acids are well known in the art. For example, one exemplary guideline to select conservative substitutions includes (original residue followed by exemplary substitution): ala/gly or ser; arg/lys; asn/gln or his; asp/glu; cys/ser; gln/asn; gly/asp; gly/ala or pro; his/asn or gin; ile/leu or val; leu/ile or val; lys/arg or gin or glu; met/leu or tyr or ile; phe/met or leu or tyr; ser/thr; thr/ser; trp/tyr; tyr/trp or phe; val/ile or leu.

An alternative exemplary guideline uses the following six groups, each containing amino acids that are conservative substitutions for one another: 1) Alanine (A), Serine (S), Threonine (T); 2) Aspartic acid (D), Glutamic acid (E); 3) Asparagine (N), Glutamine (Q); 4) Arginine (R), Lysine (I); 5) Isoleucine (I), Leucine (L), Methionine (M), Valine (V); and 6) Phenylalanine (F), Tyrosine (Y), Tryptophan (W).

Another alternative guideline is to allow for all charged amino acids as conservative substitutions for each other whether they are positive or negative.

In addition, individual substitutions, deletions or additions that alter, add or delete a single amino acid or a small percentage (for example up to 26%, or up to 20%, or up to 10%) of amino acids in an encoded sequence are also considered to be conservatively modified variations.

Substantially homologous nucleotide or polypeptide sequences have the degree of sequence identity or hybridize under certain stringent hybridization conditions as indicated below.

% Sequence Identity:

A substantially homologous nucleotide sequence has a % sequence identity of at least at least 90%, at least 95%, or at least 98%.

A substantially homologous polypeptide sequence has a % sequence identity of at least at least 90%, at least 95% or at least 98%.

Calculation of % Sequence Identity is determined as follows.

BLAST (Basic Local Alignment Search Tool) is the heuristic search algorithm employed by the programs blastn which is available at the internet website of the National Center For Biotechnology Information.

To determine % identity of a nucleotide query sequence against another nucleotide sequence, Blastn is used, using default parameters of BLAST version 2.2.1.3, including an EXPECT (statistical significance threshold for reporting matches against database sequences) of 10, and DUST filtering.

Stringent Hybridization Conditions:

Nucleotide sequences are considered substantially homologous provided that they are capable of selectively hybridizing to the nucleotide sequences presented herein, or to their complement, under stringent hybridisation conditions detailed below.

Stringent conditions are temperature of 42° C. in a solution consisting of 50% formamide, 5×SSC, and 1% SDS and washing at 65° C. in a solution consisting of 0.2×SSC and 0.1% SDS (1×SSC=0.15 M NaCl, 0.015 M Na3 Citrate pH 7.0).

Background hybridization may occur because of other nucleotide sequences present, for example, in the cDNA or genomic DNA library being screened.

A signal that is 2 fold less intense or optionally 10 fold less intense than the specific interaction observed with the target DNA is considered background. The intensity of interaction may be measured, for example, by radiolabeling the probe, e.g. with 32P.

Kit to Identify a Modulator:

A kit, for example a screening kit or high throughput screening kit, that comprises recombinant cells that express the CSR::T1R, or a substantially homologous sequence thereto; and that comprises an agonist of the CSR::T1R, for example; and without limitation, calcium chloride, N-(2-Methoxy-4-methyl-benzyl)-N'-(2-pyridin-2-yl-ethyl)-oxalamide CAS No 745047-97-6.

Using a kit comprising calcium has the advantage of binding to and activating the chimeric protein only, but not the wild-type receptor or the T1R1 and T1R3 part of the chimeric protein.

Optionally, the cells further comprise a G-protein for example for calcium signalling. Suitable G-proteins are known and described herein-above; the skilled person is aware how to introduce them to the cells if necessary. A very useful chimeric G-protein is Galpha16-gustducin 44, which is described in WO 2004/055048.

The agonist is provided in suitable concentrations, for example 1 nM to 10 mM, or 0.1 microM to 1 milliM, for example 0.1 microM to 100 microM.

Useful concentrations are, for example, for calcium chloride 0.2 to 20 mM, for N-(2-Methoxy-4-methyl-benzyl)-N'-(2-pyridin-2-yl-ethyl)-oxalamide 5 to 500 µM.

Optional kit components may include a suitable medium for culturing the recombinant cells provided, and a solid support to grow the cells on, for example, a cell culture dish or microtiter plate, these optional components will be readily available to the skilled person.

The kit may be used as follows:
(i) Recombinant cells that express the CSR::T1R chimeric protein are grown on the solid support.
(ii) test agents at concentrations from about 1 nM to 100 mM or more are added to the culture medium of defined plates or wells in the presence of the agonist in a suitable concentration
(iii) a change in a functional response of the cells is determined by comparing the response in presence and absence of the test agent, and the test agent is thereby identified as a modulator.

For example, (iii) may be performed according to any one of the assays described-herein above, in combination with any one of the detection methods that report receptor activity described herein-above. This may require specifically chosen or adapted recombinant cells, which are also described herein-above. A suitable assay is, for example, the calcium flux assay to determine activation of CSR::T1R and its change in response to a test agent.

The kit may be used to identify an enhancer as follows:
(i) Recombinant cells that express the CSR::T1R chimeric protein are grown on the solid support.
(ii) rest agents at concentrations from about 1 nM to 100 mM or more are added to the culture medium of defined plates or wells in the presence of the calcium agonist (for example, without limitation, in form of calcium chloride) in a suitable concentration.
(iii) a change in a functional response of the cells to calcium is determined by comparing the response in presence and absence of the test agent, and the test agent is thereby identified as an enhancer.

A suitable calcium chloride concentration is, for example, from about 0.2 to 20 mM, or 0.5 to 10 mM, or about 1 mM.

Confirmation of Identified Modulators:

A modulator identified by a method described hereinabove may easily be confirmed by simple sensory experiments using a panel of flavorists or test persons to taste the identified modulators. The compounds are tasted e.g. in water to confirm umami taste or together with umami tastants in comparison to a negative control without modulator to confirm a modulator that enhances the umami taste.

Large Scale Screening Assays:

Transcriptional reporter assays and most cell-based assays described herein-above are well suited for screening libraries for agents that modulate CSR::T1R activity.

The assays may be designed to screen large chemical libraries by automating the assay steps and providing compounds from any convenient source to the assays, which are typically run in parallel (for example in microtiter formats on microtiter plates in robotic assays).

Assays may be run in high throughput screening methods that involve providing a combinatorial chemical or peptide library containing a large number of potential modulators. Such libraries are then screened in one or more assays described herein-above to identify those library agents (particular chemical species or subclasses) that display the activity described herein-above. The modulators thus identified can be directly used or may serve as leads to identify further modulators by making and testing derivatives.

Synthetic compound libraries are commercially available from a number of companies including Maybridge Chemical Co. (Trevillet, Cornwall, UK), Comgenex (Princeton, N.J.), Brandon Associates (Merrimack, N.H.), and Microsource (New Milford, Conn.).

Libraries of Test Agents:

A combinatorial chemical library is a collection of diverse chemical compounds generated by either chemical synthesis or biological synthesis, by combining a number of chemical "building blocks" such as reagents. For example, a linear combinatorial chemical library such as a polypeptide library is formed by combining a set of chemical building blocks (amino acids) in every possible way for a given compound length (i.e., the number of amino acids in a polypeptide compound). Millions of chemical compounds can be synthesized through such combinatorial mixing of chemical building blocks.

A rare chemical library is available from Aldrich (Milwaukee, Wis.).

Libraries of natural compounds in the form of bacterial, fungal, plant and animal extracts are commercially available for example from Pan Laboratories (Bothell, Wash.) or Myco-Search (NC), or are readily produceable by methods well known in the art. Additionally, natural and synthetically produced libraries and compounds are readily modified through conventional chemical, physical, and biochemical means.

Other libraries include protein/expression libraries, cDNA libraries from natural sources, including, for example, foods, plants, animals, bacteria, libraries expressing randomly or systematically mutated variants of one or more polypeptides, genomic libraries in viral vectors that are used to express the mRNA content of one cell or tissue.

In a high throughput assay, it is possible to screen up to several thousand different modulators or ligands in a single day. In particular, each well of a microtiter plate can be used to run a separate assay against a selected potential modulator, or, if concentration or incubation time effects are to be observed, every 5-10 wells can test a single modulator. Thus, a single standard microtiter plate can assay about 100 modulators. If 1536 well plates are used, then a single plate can easily assay from about 100 to about 1500 different compounds. It is possible to assay several different plates per day; assay screens for up to about 6,000-20,000 different compounds is possible.

Types of Test Agents that May be Tested for their CSR::T1R Modulating Effect in the Assay Methods:

The test agents may be any agent including small chemical compounds, chemical polymers, biological polymers, peptides, proteins, sugars, carbohydrates, nucleic acids and lipids. An agent can be a synthetic compound, a mixture of compounds, a natural product or natural sample, for example plant extract, culture supernatant, or tissue sample.

As examples of compounds that may modulate, for example elicit or enhance, umami taste include glutamate or one of its salts including monosodium glutamate (MSG), inosine monophosphate (IMP), and guanosine monophosphate (GMP).

Identified modulators of umami tastants may include, for example, N-(2-Methoxy-4-methyl-benzyl)-N'-(2-pyridin-2-yl-ethyl)-oxalamide. Modulators of umami tastants are able to elicit (agonist), enhance, or inhibit an umami taste sensation. Other examples of synthetic umami agonists and/or umami modulators can also be found in WO2005041684 or related US2006045953.

Consumables include food products, beverages, oral care products, and compositions for admixture to such products, in particular flavour compositions. Flavour compositions may be added to processed foods or beverages during their processing, or they may actually be consumables in their own right, e.g. condiments such as sauces and the like. Savoury consumables usually contain salt or salt substitutes, examples of such savoury consumables include but are not limited to potato products, chips, crisps, cereal products, rice products, tapioca products, sago products, baker's products, pastry products, bread products, yeast products, salt and spice products, mustard products, vinegar products, sauces (condiments), processed foods, cooked fruits and vegetable products, meat and meat products, egg products, milk and dairy products, yoghurts, cheese products, butter and butter substitute products, milk substitute products, soy products, edible oils and fat products, beverages, alcoholic beverages, beers, soft drinks, tablets, lozenges, drops, emulsions, elixirs, syrups and other preparations for making beverages, food extracts, plant extracts, meat extracts, condiments, and combinations thereof.

Sequences of Nucleic Acids and Proteins:

The sequences employed in the constructs and methods described-herein can be found in the sequence listing hereinbelow.

SEQ ID NO:1 corresponds to the nucleotide/nucleic acid sequence encoding the CSR::T1R1 chimeric protein, SEQ ID NO: 2 corresponds to the polypeptide/amino acid sequence of the CSR::T1R1 chimeric protein.

SEQ ID NO:3 corresponds to the nucleotide/nucleic acid sequence encoding the CSR::T1R3 chimeric protein, SEQ ID NO: 4 corresponds to the polypeptide/amino acid sequence of the CSR::T1R3 chimeric protein.

Together as a complex comprising two subunits, the CSR::T1R1 chimeric protein and the CSR::T1R3 chimeric protein form a functional chimeric umami receptor.

In the transfected construct, the nucleic acid coding for the novel chimeric protein (SEQ ID NO:1 or 3) is followed by the HSV tag at the C-terminus (SEQ ID NO:5).

The resulting protein will accordingly comprise the following amino acids: amino acids of SEQ ID NO:1 followed by SEQ ID NO:5, or SEQ ID NO: 3 followed by SEQ ID NO:5.

The known full-length nucleic acid and protein sequences of the known T1R1 and T1R3 subunits of the T1R1/T1R3 receptor complex are given in SEQ ID NO: 7+8 for T1R1, and SEQ ID NO: 9+10 for T1R3.

The known full length hCaSR receptor nucleic acid and protein sequences are given in SEQ ID NO: 11+12.
SEQ ID NO: 1+2: CSR::T1R1 nucleic acid+protein
SEQ ID NO: 3+4: CSR::T1R3 nucleic acid+protein
SEQ ID NO: 5+6: HSV tag at C-terminus nucleic acid+protein
SEQ ID NO: 7+8: T1R1 (full length coding sequence) nucleic acid+protein
SEQ ID NO: 9+10: T1R3: (full length coding sequence) nucleic acid+protein
SEQ ID NO: 11+12: hCaSR nucleic acid+protein
SEQ ID NO: 13-18: primer sequences, compare example 2 and example 3

There now follows a series of examples that serve to illustrate the above-described methods. The following examples are merely illustrative and should not be construed as limiting the polypeptides, nucleic acids, expression vectors, host cells, methods, or kit in any manner.

EXAMPLES

All examples use the DNA sequences derived from human T1R1, T1R3 and hCaSR.

Example 1

Fluo-4 Calcium Assay

Fluo-4 is a fluorescent indicator for intracellular calcium and allows for determination of changes in the intracellular calcium concentration, in particular an increase in response to receptor activation occurring after ligand addition.

HEK293 cells stably expressing Gα16-gustducin 44 were used as host cells and transfected with various constructs as described in example 4.

Black, clear-bottom 96-well plates were used for all assays. They were seeded the day before with 8500 transfected cells per well and maintained at 37° C. overnight in an a growth medium appropriate for the cells used. For HEK293 cells, Dulbecco's Modified Eagle medium containing high glucose, L-glutamine, pyroxidine hydrochloride, and supplemented with 10% fetal bovine serum was used for growth and maintenance of the HEK293 cells.

At the time of the assay, the growth medium was discarded and cells were incubated for 1 hour (at 37° C. in the dark) with 50 µl of a calcium assay solution consisting of 1.5 µM Fluo-4 AM (Molecular Probes™, Invitrogen, US) and 2.5 µM probenicid (Sigma-Aldrich) dissolved in a reduced calcium C1 buffer solution. Reduced calcium C1 buffer solution contains 130 mM NaCl, 5 mM KCl, 10 mM Hepes, 0.5 mM CaCl2 (reduced from 2 mM) and 10 mM glucose (pH 7.4).

After the initial 1 hour loading period, the plates were washed 5 times with 100 µl per well of reduced calcium C1 buffer using an automated plate washer (BioTek) and after washing, the plate was further incubated for 30 minutes at room temperature in the dark to allow for complete de-esterification of the Fluo-4-AM. The buffer solutions were discarded, the plate was washed 5 times with 100 µl reduced calcium C1 wash buffer and finally the cells were reconstituted in 180 µl of reduced calcium C1 wash buffer.

For assay reading, the plate was placed in a FLIPR (fluorescence imaging plate reader (FLIPR-Tetra, Molecular Devices)), and receptor activation was initiated following addition of 20 µl of a 10× concentrated ligand stock solution, which were prepared in reduced calcium C1 buffer.

Fluorescence was continuously monitored for 15 seconds prior to ligand addition and for 105 seconds after ligand addition (45-105 sec may be sufficient).

Receptor activation is determined by the increase in peak fluorescence (F) normalized to the baseline fluorescence ($F_0$). The data are normalized using the following equation: $\Delta F/F = (F-F_0)/F_0$, where F is the peak fluorescence signal and $F_0$ is the baseline fluorescence signal, wherein the baseline fluorescence represents the mean fluorescence calculated for the first 10 to 15 seconds prior to ligand addition.

This value obtained corresponds to the calcium increase of the cell in response to a direct or indirect interaction with the transfected receptor ("signal").

As a negative control, mock transfected cells were exposed to the same concentration of ligand and the concentration of calcium traces not corresponding to a signal was determined.

Cells with an activated receptor were identified by the signal ($\Delta F/F$) being significantly above the negative control.

Example 2

Preparation of CSR::T1R1 Vector Construct

The CSR::T1R1 chimeric cDNA vector construct was generated by joining two DNA fragments generated by PCR via a common restriction enzyme site in both PCR products, namely of a PCR product containing the extracellular amino terminal domain (ATD) and the cysteine-rich domain (CRD) of hCaSR (1-Lys$^{601}$) to a PCR product representing a fragment of T1R1, containing its transmembrane domain (TMD) and its C-terminus beginning at Thr$^{610}$.

To facilitate the making of the CSR:T1R1 chimeric DNA, a BsiW I site was introduced to the primers that were used to form the two fragments described hereinabove. Using these introduced sites and the appropriate restriction enzyme in buffers and under conditions well known in the art, the fragments were joined by enzymatic ligation.

These BsiW I sites in the formed PCR-products/fragments are located at the C-terminal end of the hCaSR ATD fragment and the N-terminal end of the T1R1 fragment, respectively, allowing for ligation of the two PCR-products/fragments of the chimeric DNA. Incorporation of this BsiW I site converts the original hT1R1 sequence to a sequence wherein the Thr$^{609}$/Valine$^{610}$ of the original hT1R1 are converted into an Arg$^{609}$/Thr$^{610}$ in the resulting sequence. PCR using Platinum Taq High Fidelity Polymerase was used to amplify the fragments that comprise the CSR:T1R1 chimeric cDNA fragment using the specific primers of SEQ ID 13-16 which are given below. F designates the forward primer, R the reverse primer.

The underligned letters designate restriction sites located within the primers for subsequent subcloning of the PCR products.

```
hCaSR-ATD primer F (Seq ID NO: 13):
CACCAAGCTTATGGCATTTTATAGCTGC hCaSR-ATD primer R (Seq ID NO: 14):
ATATCGTACGCTTGGCAATGCAGGAGGT TAS1R1-fragment primer F (Seq ID NO: 15):
ATATCGTACGGTGTTTTTGGCTTTGCGT TAS1R1-fragment primer R (Seq ID NO: 16):
ATATGCGGCCGCAGGTGGAGCCGCAGCGCCT
```

The template for the PCR amplification was a full length cDNA for either the human CaSR (commercially available from Origene Inc., USA), or the human T1R1, which was isolated from a cDNA library generated from human fungiform papillae taste tissue. PCR reaction parameters were: 94° C. for 5 min followed by 35 cycles of 94° C. for 45 seconds, 54° C. for 15 seconds and 72° C. for 2 minutes, followed by a final extension cycle of 72° C. for 10 minutes.

The resulting nucleic acid fragments were separated by gel electrophoresis, purified and subcloned into the pCR-Topo-II vector (Invitrogen) and the resulting clones were verified by DNA sequencing to ensure absence of mutations arising from the PCR amplification. After sequencing, the inserts were subcloned into an expression cassette vector construct based on the pcDNA4-TO vector (purchased from Invitrogen, USA) via 3-piece ligation, allowing for assembly of the CSR::T1R1 chimeric cDNA fragment in the vector construct.

The C-terminus of the formed vector construct encodes the herpes simplex virus (HSV) glycoprotein D epitope, which can be used for immuncytochemistry studies using a specific antibody that binds to this epitope. The resulting CSR:T1R1 vector construct with CSR:T1R1 cDNA allows for expression of the CSR:T1R1:HSV protein of joined amino acid sequences of Seq ID NO:2 (CSR:T1R1) followed by Seq ID NO:6 (HSV epitope) (in amino terminus to C terminus direction).

Example 3

Preparation of the CSR::T1R3 Vector Construct

The CSR::T1R3 chimeric cDNA vector construct was generated by joining two DNA fragments generated by PCR via a common restriction enzyme site in both PCR products, namely the joining of a PCR product containing the extracellular amino terminal domain (ATD) and cysteine-rich domain (CRD) of hCaSR (1-Lys$^{601}$) to a PCR product of a fragment of T1R3 containing its transmembrane domain (TMD) and its C-terminus beginning at Arg$^{609}$.

To facilitate the making of the CSR::T1R3 chimeric cDNA vector construct, a BsiW I site was introduced into the primers which were used to make the above-described two fragments. These BsiW I sites in the formed PCR-products/fragments are located at the C-terminal end of the hCaSR-ATD fragment and the N-terminal end of the T1R3 fragment, respectively, allowing for ligation of the two fragments. Incorporation of the BsiW I site results in a vector construct that comprises a sequence wherein the Arg$^{609}$/Ser$^{610}$ of the previous hT1R3 are converted into Arg$^{609}$/Thr$^{610}$. Using the introduced ligation sites and the appropriate restriction enzyme in buffers and under conditions well known in the art, the fragments were joined by enzymatic ligation.

PCR using Platinum Taq High Fidelity Polymerase was used to amplify the fragments that comprise the CSR::T1R3 chimeric cDNA fragment using the specific primers of Seq ID NO: 17 and Seq ID NO:18 listed below. Afterwards, the amplified PCR-products of T1R3 and the amplified PCR products of hCaSR (the latter formed as described in example 2 above) were ligated via the restriction sites indicated in the primer listed below. F designates the forward primer, R the reverse primer. The underligned letters designate restriction sites located within the primers for subsequent ligation and subcloning of the amplified PCR products.

```
hCaSR-ATD F and hCaSR-ATD R:
Seq ID NO: 13 and Seq ID NO: 14
as indicated in example 2 above.

TAS1R3-fragment primer F (Seq ID NO: 17):
ATATCGTACGCGGTTCCTGGCATGGGG C

TAS1R3-fragment primer R (Seq ID NO: 18):
ATATGCGGCCGCACTCATGTTTCCCCTGATT
```

The template for the PCR amplification was a full length cDNA for either the hCaSR (purchased from Origene Inc., USA), or the hT1R3, which was isolated from a cDNA library generated from human fungiform papillae taste tissue.

PCR reaction parameters were: 94° C. for 5 min followed by 35 cycles of 94° C. for 45 seconds, 54° C. for 15 seconds and 72° C. for 2 minutes, followed by a final extension cycle of 72° C. for 10 minutes.

The resulting PCR products (ligation is performed later after the PCR products are verified) were separated by gel electrophoresis, purified and subcloned into the pCR-Topo-II vector (Invitrogen, USA). The resulting clones were verified by DNA sequencing to ensure absence of mutations arising from the PCR amplification.

After sequencing, the inserts were subcloned into an expression cassette vector construct based on the pcDNA4-TO vector (purchased from Invitrogen, USA) via 3-piece ligation, forming the CSR::T1R3 vector construct. The C-terminus of the formed vector construct encodes the herpes simplex virus (HSV) glycoprotein D epitope, which can be used for immunocytochemistry studies using a specific antibody that binds to this epitope. The resulting vector construct allows for expression of the CSR::T1R3::HSV protein of joined amino acid sequences of Seq ID NO:4 (CSR::T1R3) followed by Seq ID NO:6 (HSV epitope) (in amino terminus to C terminus direction).

Example 4

Transfections of CSR::T1R1/CSR::T1R3

Transfected vector constructs used were those described in examples 2 and 3 formed as described above. For hCaSR, a commercially available pCMV-based vector construct which is based on the full length cDNA was used (TRUECLONE collection, Origene Inc., USA).

HEK293T cells that stably express Gα16-gustducin 44 (formed as described in WO 2004/055048) were transfected with the CSR::T1R1, CSR::T1R3 constructs, or with hCaSR as follows:

On day 0, the HEK293T/Gα16-gustducin 44 cells were plated in 96-well black, clear-bottom plates at a density of 8500 cells per well and grown overnight in selective growth media. On day 1, the media was changed to an antibiotic-free and serum-free growth medium and the cells were transfected using 75 ng each of CSR:T1R1 and CSR:T1R3 (total 150 ng), T1R1 and T1R3 (total 150 ng), or 75 ng hCaSR vector construct DNA and 0.3 µl of Lipofectamine 2000 (Invitrogen).

The hCaSR vector is used as positive control for a GPCR that is sensitive to calcium, as it is sensitive to calcium and the calcium binding site lies in the VFT (venus fly trap domain) of this receptor, which is where the VFT for the chimera is derived from.

For transfection of either the CSR:T1R1/CSR:T1R3 heterodimer, 75 ng of each vector construct was combined for a total of 150 ng per pair and used together with 0.3 µl of Lipofectamine 2000. 75 ng of hCaSR vector DNA was used for this calcium-sensing monomeric GPCR The above-described lipofectamine/DNA mixtures were incubated on the cells for 3-4 hours and then replaced with an antibiotic-free, serum-containing growth medium. The cells were grown overnight and the Fluo-4 calcium assay was performed as described in example 1.

The cells transiently transfected with one of the above-described vector constructs were identified using a fluorescence imaging plate reader (FLIPR-Tetra, Molecular Devices) as described in example 1.

Example 5

Activation of the CSR:T1R1 Homomer and the CSR:T1R1/CSR:T1R3 Heterodimer by a Synthetic Umami Agonist The intracellular calcium response following stimulation with various ligands was determined in HEK293T cells stably expressing Gα16-gustducin 44 and transfected with CSR:T1R1 and/or CSR:T1R3 chimeric constructs. The results were compared to results obtained in mock transfected cells or cells transfected with the hCaSR vector construct described in example 5 (to form monomeric hCaSR).

The transfections were performed as described in example 4. Results were calculated as described in example 1 (data indicates the normalized increase in fluorescence over baseline after stimulation ($\Delta F/F$); the mean (AVG) and the ±Standard deviation (STD) of six replicate experiments is given). The following ligands were used for to stimulate the transfected cells in the concentrations as indicated in brackets:

Calcium Chloride (2 mM), N-(2-Methoxy-4-methyl-benzyl)-N'-(2-pyridin-2-yl-ethyl)-oxalamide ("745047-97-6") (25 µM), and a combination of Monosodium Glutamate (2.5 mM) together with Inosine monophosphate (0.2 mM), termed "MSG+IMP" in the table below.

The calcium mobilization signals obtained are increase in peak fluorescence (F) normalized to the baseline fluorescence ($F_0$). The data are normalized using the following equation: $\Delta F/F = (F-F_0)/F_0$, where F is the peak fluorescence signal and $F_0$ is the baseline fluorescence signal, which is determined from the average fluorescence signal measured prior to ligand addition. The $\Delta F/F$ value obtained corresponds to the calcium increase of the cell in response to a direct or indirect interaction with the transfected receptor ("signal").

Mock transfected HEK293T/Gα16-gustducin 44 cells transfected without construct that do not express a umami receptor were used as a negative control to determine signals corresponding merely to the background.

The transfected cells are exposed to the umami agonists as indicated and to a positive control (calcium) for the proteins containing calcium-sensing domains, and to a negative control (C1 buffer).

The results are shown in the table below.

The AVG column gives the mean $\Delta F/F$, the STD column gives the standard deviation. The table below shows the average change in $\Delta F/F+/-STD$ for the 6 replicates for each of the various vector constructs tested.

TABLE 1

| | Results | | | | | | | |
|---|---|---|---|---|---|---|---|---|
| | CSR:T1R1 | | CSR:T1R1/CSR:T1R3 | | hCaSR | | Neg. control (mock transfection) | |
| | AVG | STD | AVG | STD | AVG | STD | AVG | STD |
| Positive control (Calcium) | 0.78 | 0.06 | 0.72 | 0.08 | 1.44 | 0.33 | 0.24 | 0.02 |
| 745047-97-6-oxalamide | 0.31 | 0.03 | 0.43 | 0.01 | 0.04 | 0.01 | 0.03 | 0.01 |
| MSG + IMP | 0.03 | 0.01 | 0.03 | 0.01 | 0.03 | 0.01 | 0.04 | 0.003 |
| Negative control (C1 buffer) | 0.04 | 0.02 | 0.04 | 0.01 | 0.04 | 0.01 | 0.04 | 0.01 |

The negative control/mock transfection shows the signal level corresponding to background signals.

As the positive control (calcium) shows, all transfected cells which have a calcium-sensing domain react to calcium (CSR:T1R1 homomer, CSR:T1R1/CSR:T1R3 heterodimer and hCaCSR).

No response of the CSR:T1R1 chimeric homomer upon stimulation with a mixture of MSG+IMP was observed. For MSG+IMP the lack of response of the CSR:T1R chimera can be attributed to the absence of the VFT domain derived from T1R1, a domain that is absent in the CSR:T1R chimera and, without wishing to be bound by theory, is believed to contain the binding sites for MSG and IMP.

The hCaSR protein responded only to calcium chloride and could not be activated by either of the umami tastants tested.

For calcium chloride and N-(2-Methoxy-4-methyl-benzyl)-N'-(2-pyridin-2-yl-ethyl)-oxalamide (745047-97-6), a significant increase of the signal was observed in cells expressing the CSR:T1R1 chimeric homomer and the CSR:T1R1/CSR:T1R3 chimeric heterodimer. No response could be observed in either mock transfected negative control or C1 buffer negative control.

The calcium chloride and N-(2-Methoxy-4-methyl-benzyl)-N'-(2-pyridin-2-yl-ethyl)-oxalamide (745047-97-6) signals detected in the cells transfected with the chimeric CSR:T1R1/CSR:T1R3 heterodimer were significantly higher the background signals obtained in the negative control (mock transfected HEK293T/Gα16-gustducin 44 cells), and were approximately 50% of the magnitude of signals obtained in cells transfected with the hCaSR receptor.

The results demonstrate that CSR:T1R1 chimeric homomer and the CSR:T1R1/CSR:T1R3 chimeric heterodimer are activated by calcium and N-(2-Methoxy-4-methyl-benzyl)-N'-(2-pyridin-2-yl-ethyl)-oxalamide (745047-97-6).

While the receptors, nucleic acids, polypeptides, expression vectors, host cells, methods and kit have been described above in connection with certain illustrative embodiments, it is to be understood that other similar embodiments may be used or modifications and additions may be made to the described embodiments for performing the same function(s). Further, all embodiments disclosed are not necessarily in the alternative, as various embodiments may be combined to provide the desired characteristics. Variations can be made by one having ordinary skill in the art without departing from the spirit and scope of the disclosure. Therefore, the receptors, nucleic acids, polypeptides, expression vectors, host cells, methods and kit should not be limited to any single embodiment, but rather construed in breadth and scope in accordance with the recitation of the attached claims.

The invention claimed is:

1. A CSR::T1R chimeric protein able to bind to at least one of an umami modulator or an umami tastant, wherein said protein comprises one or more CSR::T1R polypeptides selected from:
   a CSR::T1R1 polypeptide comprising an amino acid sequence with a sequence identity of at least 90% to SEQ ID NO:2 and
   a CSR::T1R3 polypeptide comprising an amino acid sequence with a sequence identity of at least 90% to SEQ ID NO:4
   and wherein said protein is selected from the group consisting of a CSR::T1R1 homomeric chimeric protein, a CSR::T1R1/CSR::T1R3 heterodimeric chimeric protein, a CSR::T1R1/T1R3 heterodimeric chimeric protein, and a T1R1/CSR::T1R3 heterodimeric chimeric protein.

2. A CSR::T1R chimeric protein according to claim 1 comprising two polypeptide subunits in form of a heterodimeric protein selected from the group consisting of
   a CSR::T1R1/CSR::T1R3 heterodimeric chimeric protein,
   a CSR::T1R1/T1R3 heterodimeric chimeric protein, and a T1R1/CSR::T1R3 heterodimeric chimeric protein,
   wherein the T1R1 subunit of the heterodimer comprises a polypeptide essentially homologous to SEQ ID NO:8 with a sequence identity of at least 90%;
   and wherein the T1R3 subunit of the heterodimer comprises a polypeptide essentially homologous to SEQ ID NO:10 with a sequence identity of at least 90%.

3. A CSR::T1R chimeric protein according to claim 1 which is a CSR::T1R1 homomeric chimeric protein.

4. A CSR::T1R chimeric protein comprising two polypeptide subunits according to claim 2 which is the CSR::T1R1/CSR::T1R3 heterodimeric chimeric protein.

5. A method of producing a CSR::T1R chimeric protein as defined in claim 1 comprising the step of culturing host cells comprising an expression vector encoding for the CSR::T1R chimeric protein under conditions sufficient for expression, thereby forming the CSR::T1R chimeric protein and optionally recovering it from the cells.

6. A method to identify an agent that modulates umami taste signaling in taste cells, the method comprising the steps of:(i) contacting the cells that express a CSR::T1R chimeric protein that responds to stimuli selected from umami taste stimuli and calcium stimuli with an agent thereby providing a functional response, optionally in presence of another agent; and(ii) determining whether at least one agent affects the functional response of said CSR::T1R chimeric protein in said cells by at least one functional response in said cells; wherein said CSR::T1R chimeric protein is as defined in claim 1.

7. A method according to claim 6 wherein the cells also express a G-Protein.

8. A method according to claim 7 wherein the G-Protein is a chimeric G-protein substantially homologous to Gaq-Gustducin.

9. A method according to claim 7 wherein the G-Protein is the chimeric G-protein G alpha 16-gustducin 44.

10. A method according to claim 6 wherein step (ii) is performed by measuring a change in or caused by intracellular messengers.

11. A method according to claim 10 wherein the functional response is determined by measuring a change in an intracellular messenger selected from IP3 and calcium$^{2+}$.

12. The method of claim 6 wherein said cells are selected from the group consisting of eucaryotic cells, yeast cells, insect cells, mammalian cells, amphibian cells, worm cells and combinations thereof.

13. The method according to claim 12 wherein the cell is a mammalian cell.

14. The method according to claim 13 wherein the cell is a mammalian cell selected from the group consisting of CHO, COS, HeLa and HEK-293 cells.

15. The method according to claim 6 wherein step (i) further comprises contacting the CSR::T1R chimeric protein with a test agent in presence of calcium.

16. The method according to claim 15 wherein the calcium is provided in the form of calcium chloride.

17. A kit comprising:(i) recombinant cells that express a CSR::T1R chimeric protein as defined in claim 1 and(ii) an agonist of the CSR::T1R chimeric protein, for combined use to identify test agents as modulators of the CSR::T1R chimeric protein.

18. A method of using the kit of claim 17 comprising:(i) growing recombinant cells that express the CSR::T1R chimeric protein,(ii) adding test agents in the presence of the agonist in a suitable concentration, and(iii) determining a change in a functional response of the cells by comparing the response in presence and absence of the test agent, and the test agent is thereby identified as a modulator of the CSR::T1R chimeric protein.

19. A method to identify an agent that modulates the CSR::T1R chimeric protein as defined in claim 1, the method comprising the steps of:(i) measuring a parameter that changes in response to a ligand binding to the CSR::T1R chimeric protein, and(ii) determining a change of the parameter in response to a test agent, optionally in presence of a ligand, in comparison to a negative control and thereby identifying a modulator including a ligand.

20. Method according to claim 19 wherein the ligand is selected from the group consisting of calcium, calcium ions and calcium chloride.

21. Method according to claim 19 wherein step (i) is performed by a method selected from the group consisting of fluorescence spectroscopy, NMR spectroscopy, measuring of one or more of absorbance, refractive index, hydrodynamic methods, chromatography, measuring solubility, biochemical, wherein the methods measure the properties of the CSR::T1R chimeric protein in a suitable environment selected form the group consisting of solution, bilayer membrane, attached to a solid phase, in a lipid monolayer, bound on a membrane, and in vesicles.

22. A CSR::T1R chimeric protein according to claim 1 wherein the umami modulator is a umami taste receptor ligand, agonist, partial agonist, antagonist, inverse agonist, inhibitor, or enhancer.

23. A nucleic acid encoding a CSR::T1R1 chimeric protein able to bind at least one of an umami modulator or an umami tastant, comprising one or more of
  a nucleic acid comprising a nucleotide sequence with a sequence identity of at least 90% to SEQ ID NO:1 encoding a CSR::T1R1 polypeptide comprising an amino acid sequence with a sequence identity of at least 90% to SEQ ID NO:2 or a CSR::T1R3 polypeptide comprising an amino acid sequence with a sequence identity of at least 90% to SEQ ID NO:4
  wherein the nucleic acid optionally comprises SEQ ID NO:6 (HSV tag) at or near its end to form the C-terminus in the corresponding protein.

24. An expression vector comprising the nucleic acid as defined in claim 23.

25. A host cell transfected with an expression vector as defined in claim 24.

26. The host cell of claim 25 stably expressing the CSR::T1R chimeric protein and a G-Protein, optionally a G-Protein substantially homologous to Gaq-Gustducin.

27. The host cell of claim 25 transiently expressing the CSR::T1R chimeric protein and a G-Protein, optionally a G-Protein substantially homologous to Gaq-Gustducin.

28. A nucleic acid according to claim 23 wherein the umami modulator is a umami taste receptor ligand, agonist, partial agonist, antagonist, inverse agonist, inhibitor, or enhancer.

* * * * *

SEQUENCE LISTING

<160> NUMBER OF SEQ ID NOS: 18

<210> SEQ ID NO 1
<211> LENGTH: 2661
<212> TYPE: DNA
<213> ORGANISM: human
<220> FEATURE:
<221> NAME/KEY: CDS
<222> LOCATION: (1)..(2661)

<400> SEQUENCE: 1

| | | | | | | | | | | | | | | | |
|---|---|---|---|---|---|---|---|---|---|---|---|---|---|---|---|
| atg | gca | ttt | tat | agc | tgc | tgc | tgg | gtc | ctc | ttg | gca | ctc | acc | tgg cac | 48 |
| Met | Ala | Phe | Tyr | Ser | Cys | Cys | Trp | Val | Leu | Leu | Ala | Leu | Thr | Trp His | |
| 1 | | | | 5 | | | | | 10 | | | | | 15 | |

| acc | tct | gcc | tac | ggg | cca | gac | cag | cga | gcc | caa | aag | aag | ggg | gac att | 96 |
|---|---|---|---|---|---|---|---|---|---|---|---|---|---|---|---|
| Thr | Ser | Ala | Tyr | Gly | Pro | Asp | Gln | Arg | Ala | Gln | Lys | Lys | Gly | Asp Ile | |
| | | | 20 | | | | | 25 | | | | | 30 | | |

| atc | ctt | ggg | ggg | ctc | ttt | cct | att | cat | ttt | gga | gta | gca | gct | aaa gat | 144 |
|---|---|---|---|---|---|---|---|---|---|---|---|---|---|---|---|
| Ile | Leu | Gly | Gly | Leu | Phe | Pro | Ile | His | Phe | Gly | Val | Ala | Ala | Lys Asp | |
| | | 35 | | | | | 40 | | | | | 45 | | | |

| caa | gat | ctc | aaa | tca | agg | ccg | gag | tct | gtg | gaa | tgt | atc | agg | tat aat | 192 |
|---|---|---|---|---|---|---|---|---|---|---|---|---|---|---|---|
| Gln | Asp | Leu | Lys | Ser | Arg | Pro | Glu | Ser | Val | Glu | Cys | Ile | Arg | Tyr Asn | |
| 50 | | | | | 55 | | | | | 60 | | | | | |

| ttc | cgt | ggg | ttt | cgc | tgg | tta | cag | gct | atg | ata | ttt | gcc | ata | gag gag | 240 |
|---|---|---|---|---|---|---|---|---|---|---|---|---|---|---|---|
| Phe | Arg | Gly | Phe | Arg | Trp | Leu | Gln | Ala | Met | Ile | Phe | Ala | Ile | Glu Glu | |
| 65 | | | | | 70 | | | | | 75 | | | | | 80 |

| ata | aac | agc | agc | cca | gcc | ctt | ctt | ccc | aac | ttg | acg | ctg | gga | tac agg | 288 |
|---|---|---|---|---|---|---|---|---|---|---|---|---|---|---|---|
| Ile | Asn | Ser | Ser | Pro | Ala | Leu | Leu | Pro | Asn | Leu | Thr | Leu | Gly | Tyr Arg | |
| | | | | 85 | | | | | 90 | | | | | 95 | |

| ata | ttt | gac | act | tgc | aac | acc | gtt | tct | aag | gcc | ttg | gaa | gcc | acc ctg | 336 |
|---|---|---|---|---|---|---|---|---|---|---|---|---|---|---|---|
| Ile | Phe | Asp | Thr | Cys | Asn | Thr | Val | Ser | Lys | Ala | Leu | Glu | Ala | Thr Leu | |
| | | | 100 | | | | | 105 | | | | | 110 | | |

| agt | ttt | gtt | gct | caa | aac | aaa | att | gat | tct | ttg | aac | ctt | gat | gag ttc | 384 |
|---|---|---|---|---|---|---|---|---|---|---|---|---|---|---|---|
| Ser | Phe | Val | Ala | Gln | Asn | Lys | Ile | Asp | Ser | Leu | Asn | Leu | Asp | Glu Phe | |
| | | 115 | | | | | 120 | | | | | 125 | | | |

| tgc | aac | tgc | tca | gag | cac | att | ccc | tct | acg | att | gct | gtg | gtg | gga gca | 432 |
|---|---|---|---|---|---|---|---|---|---|---|---|---|---|---|---|
| Cys | Asn | Cys | Ser | Glu | His | Ile | Pro | Ser | Thr | Ile | Ala | Val | Val | Gly Ala | |
| | 130 | | | | | 135 | | | | | 140 | | | | |

| act | ggc | tca | ggc | gtc | tcc | acg | gca | gtg | gca | aat | ctg | ctg | ggg | ctc ttc | 480 |
|---|---|---|---|---|---|---|---|---|---|---|---|---|---|---|---|
| Thr | Gly | Ser | Gly | Val | Ser | Thr | Ala | Val | Ala | Asn | Leu | Leu | Gly | Leu Phe | |
| 145 | | | | | 150 | | | | | 155 | | | | | 160 |

| tac | att | ccc | cag | gtc | agt | tat | gcc | tcc | tcc | agc | aga | ctc | ctc | agc aac | 528 |
|---|---|---|---|---|---|---|---|---|---|---|---|---|---|---|---|
| Tyr | Ile | Pro | Gln | Val | Ser | Tyr | Ala | Ser | Ser | Ser | Arg | Leu | Leu | Ser Asn | |
| | | | | 165 | | | | | 170 | | | | | 175 | |

| aag | aat | caa | ttc | aag | tct | ttc | ctc | cga | acc | atc | ccc | aat | gat | gag cac | 576 |
|---|---|---|---|---|---|---|---|---|---|---|---|---|---|---|---|
| Lys | Asn | Gln | Phe | Lys | Ser | Phe | Leu | Arg | Thr | Ile | Pro | Asn | Asp | Glu His | |
| | | | 180 | | | | | 185 | | | | | 190 | | |

| cag | gcc | act | gcc | atg | gca | gac | atc | atc | gag | tat | ttc | cgc | tgg | aac tgg | 624 |
|---|---|---|---|---|---|---|---|---|---|---|---|---|---|---|---|
| Gln | Ala | Thr | Ala | Met | Ala | Asp | Ile | Ile | Glu | Tyr | Phe | Arg | Trp | Asn Trp | |
| | | 195 | | | | | 200 | | | | | 205 | | | |

| gtg | ggc | aca | att | gca | gct | gat | gac | gac | tat | ggg | cgg | ccg | ggg | att gag | 672 |
|---|---|---|---|---|---|---|---|---|---|---|---|---|---|---|---|
| Val | Gly | Thr | Ile | Ala | Ala | Asp | Asp | Asp | Tyr | Gly | Arg | Pro | Gly | Ile Glu | |
| | 210 | | | | | 215 | | | | | 220 | | | | |

| aaa | ttc | cga | gag | gaa | gct | gag | gaa | agg | gat | atc | tgc | atc | gac | ttc agt | 720 |
|---|---|---|---|---|---|---|---|---|---|---|---|---|---|---|---|
| Lys | Phe | Arg | Glu | Glu | Ala | Glu | Glu | Arg | Asp | Ile | Cys | Ile | Asp | Phe Ser | |
| 225 | | | | | 230 | | | | | 235 | | | | | 240 |

| gaa | ctc | atc | tcc | cag | tac | tct | gat | gag | gaa | gag | atc | cag | cat | gtg gta | 768 |
|---|---|---|---|---|---|---|---|---|---|---|---|---|---|---|---|
| Glu | Leu | Ile | Ser | Gln | Tyr | Ser | Asp | Glu | Glu | Glu | Ile | Gln | His | Val Val | |
| | | | | 245 | | | | | 250 | | | | | 255 | |

| gag | gtg | att | caa | aat | tcc | acg | gcc | aaa | gtc | atc | gtg | gtt | ttc | tcc agt | 816 |

|   |   |   |   |   |   |   |   |   |   |   |   |   |   |
|---|---|---|---|---|---|---|---|---|---|---|---|---|---|
| Glu | Val | Ile | Gln | Asn | Ser | Thr | Ala | Lys | Val | Ile | Val | Phe | Ser | Ser |
|  |  |  | 260 |  |  |  | 265 |  |  |  | 270 |  |  |

```
ggc cca gat ctt gag ccc ctc atc aag gag att gtc cgg cgc aat atc      864
Gly Pro Asp Leu Glu Pro Leu Ile Lys Glu Ile Val Arg Arg Asn Ile
        275                 280                 285 acg ggc aag atc tgg ctg gcc agc gag gcc tgg gcc agc tcc tcc ctg      912
Thr Gly Lys Ile Trp Leu Ala Ser Glu Ala Trp Ala Ser Ser Ser Leu
290                 295                 300 atc gcc atg cct cag tac ttc cac gtg gtt ggc ggc acc att gga ttc      960
Ile Ala Met Pro Gln Tyr Phe His Val Val Gly Gly Thr Ile Gly Phe
305                 310                 315                 320 gct ctg aag gct ggg cag atc cca ggc ttc cgg gaa ttc ctg aag aag     1008
Ala Leu Lys Ala Gly Gln Ile Pro Gly Phe Arg Glu Phe Leu Lys Lys
                325                 330                 335 gtc cat ccc agg aag tct gtc cac aat ggt ttt gcc aag gag ttt tgg     1056
Val His Pro Arg Lys Ser Val His Asn Gly Phe Ala Lys Glu Phe Trp
            340                 345                 350 gaa gaa aca ttt aac tgc cac ctc caa gaa ggt gca aaa gga cct tta     1104
Glu Glu Thr Phe Asn Cys His Leu Gln Glu Gly Ala Lys Gly Pro Leu
        355                 360                 365 cct gtg gac acc ttt ctg aga ggt cac gaa gaa agt ggc gac agg ttt     1152
Pro Val Asp Thr Phe Leu Arg Gly His Glu Glu Ser Gly Asp Arg Phe
370                 375                 380 agc aac agc tcg aca gcc ttc cga ccc ctc tgt aca ggg gat gag aac     1200
Ser Asn Ser Ser Thr Ala Phe Arg Pro Leu Cys Thr Gly Asp Glu Asn
385                 390                 395                 400 atc agc agt gtc gag acc cct tac ata gat tac acg cat tta cgg ata     1248
Ile Ser Ser Val Glu Thr Pro Tyr Ile Asp Tyr Thr His Leu Arg Ile
                405                 410                 415 tcc tac aat gtg tac tta gca gtc tac tcc att gcc cac gcc ttg caa     1296
Ser Tyr Asn Val Tyr Leu Ala Val Tyr Ser Ile Ala His Ala Leu Gln
            420                 425                 430 gat ata tat acc tgc tta cct ggg aga ggg ctc ttc acc aat ggc tcc     1344
Asp Ile Tyr Thr Cys Leu Pro Gly Arg Gly Leu Phe Thr Asn Gly Ser
        435                 440                 445 tgt gca gac atc aag aaa gtt gag gcg tgg cag gtc ctg aag cac cta     1392
Cys Ala Asp Ile Lys Lys Val Glu Ala Trp Gln Val Leu Lys His Leu
450                 455                 460 cgg cat cta aac ttt aca aac aat atg ggg gag cag gtg acc ttt gat     1440
Arg His Leu Asn Phe Thr Asn Asn Met Gly Glu Gln Val Thr Phe Asp
465                 470                 475                 480 gag tgt ggt gac ctg gtg ggg aac tat tcc atc atc aac tgg cac ctc     1488
Glu Cys Gly Asp Leu Val Gly Asn Tyr Ser Ile Ile Asn Trp His Leu
                485                 490                 495 tcc cca gag gat ggc tcc atc gtg ttt aag gaa gtc ggg tat tac aac     1536
Ser Pro Glu Asp Gly Ser Ile Val Phe Lys Glu Val Gly Tyr Tyr Asn
            500                 505                 510 gtc tat gcc aag aag gga gaa aga ctc ttc atc aac gag gag aaa atc     1584
Val Tyr Ala Lys Lys Gly Glu Arg Leu Phe Ile Asn Glu Glu Lys Ile
        515                 520                 525 ctg tgg agt ggg ttc tcc agg gag gtg ccc ttc tcc aac tgc agc cga     1632
Leu Trp Ser Gly Phe Ser Arg Glu Val Pro Phe Ser Asn Cys Ser Arg
530                 535                 540 gac tgc ctg gca ggg acc agg aaa ggg atc att gag ggg gag ccc acc     1680
Asp Cys Leu Ala Gly Thr Arg Lys Gly Ile Ile Glu Gly Glu Pro Thr
545                 550                 555                 560 tgc tgc ttt gag tgt gtg gag tgt cct gat ggg gag tat agt gat gag     1728
Cys Cys Phe Glu Cys Val Glu Cys Pro Asp Gly Glu Tyr Ser Asp Glu
                565                 570                 575 aca gat gcc agt gcc tgt aac aag tgc cca gat gac ttc tgg tcc aat     1776
```

```
        Thr Asp Ala Ser Ala Cys Asn Lys Cys Pro Asp Asp Phe Trp Ser Asn
                    580                 585                 590 gag aac cac acc tcc tgc att gcc aag cgt acg gtg ttt ttg gct ttg        1824
Glu Asn His Thr Ser Cys Ile Ala Lys Arg Thr Val Phe Leu Ala Leu
            595                 600                 605 cgt gag cac acc tct tgg gtg ctg ctg gca gct aac acg ctg ctg            1872
Arg Glu His Thr Ser Trp Val Leu Leu Ala Ala Asn Thr Leu Leu Leu
        610                 615                 620 ctg ctg ctg ctt ggg act gct ggc ctg ttt gcc tgg cac cta gac acc        1920
Leu Leu Leu Leu Gly Thr Ala Gly Leu Phe Ala Trp His Leu Asp Thr
625                 630                 635                 640 cct gtg gtg agg tca gca ggg ggc cgc ctg tgc ttt ctt atg ctg ggc        1968
Pro Val Val Arg Ser Ala Gly Gly Arg Leu Cys Phe Leu Met Leu Gly
                645                 650                 655 tcc ctg gca gca ggt agt ggc agc ctc tat ggc ttc ttt ggg gaa ccc        2016
Ser Leu Ala Ala Gly Ser Gly Ser Leu Tyr Gly Phe Phe Gly Glu Pro
            660                 665                 670 aca agg cct gcg tgc ttg cta cgc cag gcc ctc ttt gcc ctt ggt ttc        2064
Thr Arg Pro Ala Cys Leu Leu Arg Gln Ala Leu Phe Ala Leu Gly Phe
        675                 680                 685 acc atc ttc ctg tcc tgc ctg aca gtt cgc tca ttc caa cta atc atc        2112
Thr Ile Phe Leu Ser Cys Leu Thr Val Arg Ser Phe Gln Leu Ile Ile
    690                 695                 700 atc ttc aag ttt tcc acc aag gta cct aca ttc tac cac gcc tgg gtc        2160
Ile Phe Lys Phe Ser Thr Lys Val Pro Thr Phe Tyr His Ala Trp Val
705                 710                 715                 720 caa aac cac ggt gct ggc ctg ttt gtg atg atc agc gcg gcc cag            2208
Gln Asn His Gly Ala Gly Leu Phe Val Met Ile Ser Ala Ala Gln
                725                 730                 735 ctg ctt atc tgt cta act tgg ctg gtg gtg tgg acc cca ctg cct gct        2256
Leu Leu Ile Cys Leu Thr Trp Leu Val Val Trp Thr Pro Leu Pro Ala
            740                 745                 750 agg gaa tac cag cgc ttc ccc cat ctg gtg atg ctt gag tgc aca gag        2304
Arg Glu Tyr Gln Arg Phe Pro His Leu Val Met Leu Glu Cys Thr Glu
        755                 760                 765 acc aac tcc ctg ggc ttc ata ctg gcc ttc ctc tac aat ggc ctc ctc        2352
Thr Asn Ser Leu Gly Phe Ile Leu Ala Phe Leu Tyr Asn Gly Leu Leu
    770                 775                 780 tcc atc agt gcc ttt gcc tgc agc tac ctg ggt aag gac ttg cca gag        2400
Ser Ile Ser Ala Phe Ala Cys Ser Tyr Leu Gly Lys Asp Leu Pro Glu
785                 790                 795                 800 aac tac aac gag gcc aaa tgt gtc acc ttc agc ctg ctc ttc aac ttc        2448
Asn Tyr Asn Glu Ala Lys Cys Val Thr Phe Ser Leu Leu Phe Asn Phe
                805                 810                 815 gtg tcc tgg atc gcc ttc ttc acc acg gcc agc gtc tac gac ggc aag        2496
Val Ser Trp Ile Ala Phe Phe Thr Thr Ala Ser Val Tyr Asp Gly Lys
            820                 825                 830 tac ctg cct gcg gcc aac atg atg gct ggg ctg agc agc ctg agc agc        2544
Tyr Leu Pro Ala Ala Asn Met Met Ala Gly Leu Ser Ser Leu Ser Ser
        835                 840                 845 ggc ttc ggt ggg tat ttt ctg cct aag tgc tac gtg atc ctc tgc cgc        2592
Gly Phe Gly Gly Tyr Phe Leu Pro Lys Cys Tyr Val Ile Leu Cys Arg
    850                 855                 860 cca gac ctc aac agc aca gag cac ttc cag gcc tcc att cag gac tac        2640
Pro Asp Leu Asn Ser Thr Glu His Phe Gln Ala Ser Ile Gln Asp Tyr
865                 870                 875                 880 acg agg cgc tgc ggc tcc acc                                            2661
Thr Arg Arg Cys Gly Ser Thr
                885
```

```
<210> SEQ ID NO 2
<211> LENGTH: 887
<212> TYPE: PRT
<213> ORGANISM: human

<400> SEQUENCE: 2

Met Ala Phe Tyr Ser Cys Cys Trp Val Leu Leu Ala Leu Thr Trp His
  1               5                  10                  15

Thr Ser Ala Tyr Gly Pro Asp Gln Arg Ala Gln Lys Lys Gly Asp Ile
             20                  25                  30

Ile Leu Gly Gly Leu Phe Pro Ile His Phe Gly Val Ala Ala Lys Asp
         35                  40                  45

Gln Asp Leu Lys Ser Arg Pro Glu Ser Val Glu Cys Ile Arg Tyr Asn
     50                  55                  60

Phe Arg Gly Phe Arg Trp Leu Gln Ala Met Ile Phe Ala Ile Glu Glu
 65                  70                  75                  80

Ile Asn Ser Ser Pro Ala Leu Leu Pro Asn Leu Thr Leu Gly Tyr Arg
                 85                  90                  95

Ile Phe Asp Thr Cys Asn Thr Val Ser Lys Ala Leu Glu Ala Thr Leu
            100                 105                 110

Ser Phe Val Ala Gln Asn Lys Ile Asp Ser Leu Asn Leu Asp Glu Phe
        115                 120                 125

Cys Asn Cys Ser Glu His Ile Pro Ser Thr Ile Ala Val Val Gly Ala
    130                 135                 140

Thr Gly Ser Gly Val Ser Thr Ala Val Ala Asn Leu Leu Gly Leu Phe
145                 150                 155                 160

Tyr Ile Pro Gln Val Ser Tyr Ala Ser Ser Arg Leu Leu Ser Asn
                165                 170                 175

Lys Asn Gln Phe Lys Ser Phe Leu Arg Thr Ile Pro Asn Asp Glu His
                180                 185                 190

Gln Ala Thr Ala Met Ala Asp Ile Ile Glu Tyr Phe Arg Trp Asn Trp
            195                 200                 205

Val Gly Thr Ile Ala Ala Asp Asp Tyr Gly Arg Pro Gly Ile Glu
        210                 215                 220

Lys Phe Arg Glu Glu Ala Glu Glu Arg Asp Ile Cys Ile Asp Phe Ser
225                 230                 235                 240

Glu Leu Ile Ser Gln Tyr Ser Asp Glu Glu Ile Gln His Val Val
                245                 250                 255

Glu Val Ile Gln Asn Ser Thr Ala Lys Val Ile Val Phe Ser Ser
            260                 265                 270

Gly Pro Asp Leu Glu Pro Leu Ile Lys Glu Ile Val Arg Arg Asn Ile
        275                 280                 285

Thr Gly Lys Ile Trp Leu Ala Ser Glu Ala Trp Ala Ser Ser Ser Leu
    290                 295                 300

Ile Ala Met Pro Gln Tyr Phe His Val Val Gly Gly Thr Ile Gly Phe
305                 310                 315                 320

Ala Leu Lys Ala Gly Gln Ile Pro Gly Phe Arg Glu Phe Leu Lys Lys
                325                 330                 335

Val His Pro Arg Lys Ser Val His Asn Gly Phe Ala Lys Glu Phe Trp
            340                 345                 350

Glu Glu Thr Phe Asn Cys His Leu Gln Glu Gly Ala Lys Gly Pro Leu
        355                 360                 365

Pro Val Asp Thr Phe Leu Arg Gly His Glu Glu Ser Gly Asp Arg Phe
    370                 375                 380

Ser Asn Ser Ser Thr Ala Phe Arg Pro Leu Cys Thr Gly Asp Glu Asn
```

-continued

```
            385                 390                 395                 400
        Ile Ser Ser Val Glu Thr Pro Tyr Ile Asp Tyr Thr His Leu Arg Ile
                            405                 410                 415

Ser Tyr Asn Val Tyr Leu Ala Val Tyr Ser Ile Ala His Ala Leu Gln
                            420                 425             430

Asp Ile Tyr Thr Cys Leu Pro Gly Arg Gly Leu Phe Thr Asn Gly Ser
                        435                 440                 445

Cys Ala Asp Ile Lys Lys Val Glu Ala Trp Gln Val Leu Lys His Leu
            450                 455                 460

Arg His Leu Asn Phe Thr Asn Asn Met Gly Glu Gln Val Thr Phe Asp
        465                 470                 475                 480

Glu Cys Gly Asp Leu Val Gly Asn Tyr Ser Ile Ile Asn Trp His Leu
                        485                 490                 495

Ser Pro Glu Asp Gly Ser Ile Val Phe Lys Glu Val Gly Tyr Tyr Asn
                    500                 505                 510

Val Tyr Ala Lys Lys Gly Glu Arg Leu Phe Ile Asn Glu Glu Lys Ile
                    515                 520                 525

Leu Trp Ser Gly Phe Ser Arg Glu Val Pro Phe Ser Asn Cys Ser Arg
            530                 535                 540

Asp Cys Leu Ala Gly Thr Arg Lys Gly Ile Ile Glu Gly Glu Pro Thr
        545                 550                 555                 560

Cys Cys Phe Glu Cys Val Glu Cys Pro Asp Gly Glu Tyr Ser Asp Glu
                            565                 570                 575

Thr Asp Ala Ser Ala Cys Asn Lys Cys Pro Asp Asp Phe Trp Ser Asn
                        580                 585                 590

Glu Asn His Thr Ser Cys Ile Ala Lys Arg Thr Val Phe Leu Ala Leu
                    595                 600                 605

Arg Glu His Thr Ser Trp Val Leu Leu Ala Ala Asn Thr Leu Leu Leu
                    610                 615                 620

Leu Leu Leu Leu Gly Thr Ala Gly Leu Phe Ala Trp His Leu Asp Thr
        625                 630                 635                 640

Pro Val Val Arg Ser Ala Gly Gly Arg Leu Cys Phe Leu Met Leu Gly
                        645                 650                 655

Ser Leu Ala Ala Gly Ser Gly Ser Leu Tyr Gly Phe Phe Gly Glu Pro
                        660                 665                 670

Thr Arg Pro Ala Cys Leu Leu Arg Gln Ala Leu Phe Ala Leu Gly Phe
                    675                 680                 685

Thr Ile Phe Leu Ser Cys Leu Thr Val Arg Ser Phe Gln Leu Ile Ile
                690                 695                 700

Ile Phe Lys Phe Ser Thr Lys Val Pro Thr Phe Tyr His Ala Trp Val
        705                 710                 715                 720

Gln Asn His Gly Ala Gly Leu Phe Val Met Ile Ser Ser Ala Ala Gln
                        725                 730                 735

Leu Leu Ile Cys Leu Thr Trp Leu Val Val Trp Thr Pro Leu Pro Ala
                    740                 745                 750

Arg Glu Tyr Gln Arg Phe Pro His Leu Val Met Leu Glu Cys Thr Glu
                755                 760                 765

Thr Asn Ser Leu Gly Phe Ile Leu Ala Phe Leu Tyr Asn Gly Leu Leu
                770                 775                 780

Ser Ile Ser Ala Phe Ala Cys Ser Tyr Leu Gly Lys Asp Leu Pro Glu
        785                 790                 795                 800

Asn Tyr Asn Glu Ala Lys Cys Val Thr Phe Ser Leu Leu Phe Asn Phe
                        805                 810                 815
```

```
Val Ser Trp Ile Ala Phe Phe Thr Thr Ala Ser Val Tyr Asp Gly Lys
            820                 825                 830

Tyr Leu Pro Ala Ala Asn Met Met Ala Gly Leu Ser Ser Leu Ser Ser
        835                 840                 845

Gly Phe Gly Tyr Phe Leu Pro Lys Cys Tyr Val Ile Leu Cys Arg
    850                 855                 860

Pro Asp Leu Asn Ser Thr Glu His Phe Gln Ala Ser Ile Gln Asp Tyr
865                 870                 875                 880

Thr Arg Arg Cys Gly Ser Thr
                885

<210> SEQ ID NO 3
<211> LENGTH: 2688
<212> TYPE: DNA
<213> ORGANISM: human
<220> FEATURE:
<221> NAME/KEY: CDS
<222> LOCATION: (1)..(2688)

<400> SEQUENCE: 3
```

| | | | | | | | | | | | | | | | | |
|---|---|---|---|---|---|---|---|---|---|---|---|---|---|---|---|---|
| atg | gca | ttt | tat | agc | tgc | tgc | tgg | gtc | ctc | ttg | gca | ctc | acc | tgg | cac | 48 |
| Met | Ala | Phe | Tyr | Ser | Cys | Cys | Trp | Val | Leu | Leu | Ala | Leu | Thr | Trp | His | |
| 1 | | | | 5 | | | | | 10 | | | | | 15 | | |
| acc | tct | gcc | tac | ggg | cca | gac | cag | cga | gcc | caa | aag | aag | ggg | gac | att | 96 |
| Thr | Ser | Ala | Tyr | Gly | Pro | Asp | Gln | Arg | Ala | Gln | Lys | Lys | Gly | Asp | Ile | |
| | | 20 | | | | | 25 | | | | | 30 | | | | |
| atc | ctt | ggg | ggg | ctc | ttt | cct | att | cat | ttt | gga | gta | gca | gct | aaa | gat | 144 |
| Ile | Leu | Gly | Gly | Leu | Phe | Pro | Ile | His | Phe | Gly | Val | Ala | Ala | Lys | Asp | |
| | | | 35 | | | | | 40 | | | | | 45 | | | |
| caa | gat | ctc | aaa | tca | agg | ccg | gag | tct | gtg | gaa | tgt | atc | agg | tat | aat | 192 |
| Gln | Asp | Leu | Lys | Ser | Arg | Pro | Glu | Ser | Val | Glu | Cys | Ile | Arg | Tyr | Asn | |
| 50 | | | | | 55 | | | | | 60 | | | | | | |
| ttc | cgt | ggg | ttt | cgc | tgg | tta | cag | gct | atg | ata | ttt | gcc | ata | gag | gag | 240 |
| Phe | Arg | Gly | Phe | Arg | Trp | Leu | Gln | Ala | Met | Ile | Phe | Ala | Ile | Glu | Glu | |
| 65 | | | | | 70 | | | | | 75 | | | | | 80 | |
| ata | aac | agc | agc | cca | gcc | ctt | ctt | ccc | aac | ttg | acg | ctg | gga | tac | agg | 288 |
| Ile | Asn | Ser | Ser | Pro | Ala | Leu | Leu | Pro | Asn | Leu | Thr | Leu | Gly | Tyr | Arg | |
| | | | | 85 | | | | | 90 | | | | | 95 | | |
| ata | ttt | gac | act | tgc | aac | acc | gtt | tct | aag | gcc | ttg | gaa | gcc | acc | ctg | 336 |
| Ile | Phe | Asp | Thr | Cys | Asn | Thr | Val | Ser | Lys | Ala | Leu | Glu | Ala | Thr | Leu | |
| | | | 100 | | | | | 105 | | | | | 110 | | | |
| agt | ttt | gtt | gct | caa | aac | aaa | att | gat | tct | ttg | aac | ctt | gat | gag | ttc | 384 |
| Ser | Phe | Val | Ala | Gln | Asn | Lys | Ile | Asp | Ser | Leu | Asn | Leu | Asp | Glu | Phe | |
| | | | 115 | | | | | 120 | | | | | 125 | | | |
| tgc | aac | tgc | tca | gag | cac | att | ccc | tct | acg | att | gct | gtg | gtg | gga | gca | 432 |
| Cys | Asn | Cys | Ser | Glu | His | Ile | Pro | Ser | Thr | Ile | Ala | Val | Val | Gly | Ala | |
| | | 130 | | | | | 135 | | | | | 140 | | | | |
| act | ggc | tca | ggc | gtc | tcc | acg | gca | gtg | gca | aat | ctg | ctg | ggg | ctc | ttc | 480 |
| Thr | Gly | Ser | Gly | Val | Ser | Thr | Ala | Val | Ala | Asn | Leu | Leu | Gly | Leu | Phe | |
| 145 | | | | | 150 | | | | | 155 | | | | | 160 | |
| tac | att | ccc | cag | gtc | agt | tat | gcc | tcc | tcc | agc | aga | ctc | ctc | agc | aac | 528 |
| Tyr | Ile | Pro | Gln | Val | Ser | Tyr | Ala | Ser | Ser | Ser | Arg | Leu | Leu | Ser | Asn | |
| | | | | 165 | | | | | 170 | | | | | 175 | | |
| aag | aat | caa | ttc | aag | tct | ttc | ctc | cga | acc | atc | ccc | aat | gat | gag | cac | 576 |
| Lys | Asn | Gln | Phe | Lys | Ser | Phe | Leu | Arg | Thr | Ile | Pro | Asn | Asp | Glu | His | |
| | | | 180 | | | | | 185 | | | | | 190 | | | |
| cag | gcc | act | gcc | atg | gca | gac | atc | atc | gag | tat | ttc | cgc | tgg | aac | tgg | 624 |
| Gln | Ala | Thr | Ala | Met | Ala | Asp | Ile | Ile | Glu | Tyr | Phe | Arg | Trp | Asn | Trp | |
| | | | 195 | | | | | 200 | | | | | 205 | | | |
| gtg | ggc | aca | att | gca | gct | gat | gac | gac | tat | ggg | cgg | ccg | ggg | att | gag | 672 |
| Val | Gly | Thr | Ile | Ala | Ala | Asp | Asp | Asp | Tyr | Gly | Arg | Pro | Gly | Ile | Glu | |

-continued

|  |  |  |  | 210 |  |  |  | 215 |  |  |  | 220 |  |  |  |  |
|---|---|---|---|---|---|---|---|---|---|---|---|---|---|---|---|---|
| aaa | ttc | cga | gag | gaa | gct | gag | gaa | agg | gat | atc | tgc | atc | gac | ttc | agt | 720 |
| Lys | Phe | Arg | Glu | Glu | Ala | Glu | Glu | Arg | Asp | Ile | Cys | Ile | Asp | Phe | Ser |  |
| 225 |  |  |  | 230 |  |  |  | 235 |  |  |  | 240 |  |  |  |  |
| gaa | ctc | atc | tcc | cag | tac | tct | gat | gag | gaa | gag | atc | cag | cat | gtg | gta | 768 |
| Glu | Leu | Ile | Ser | Gln | Tyr | Ser | Asp | Glu | Glu | Glu | Ile | Gln | His | Val | Val |  |
|  |  |  |  | 245 |  |  |  | 250 |  |  |  | 255 |  |  |  |  |
| gag | gtg | att | caa | aat | tcc | acg | gcc | aaa | gtc | atc | gtg | gtt | ttc | tcc | agt | 816 |
| Glu | Val | Ile | Gln | Asn | Ser | Thr | Ala | Lys | Val | Ile | Val | Val | Phe | Ser | Ser |  |
| 260 |  |  |  |  |  | 265 |  |  |  | 270 |  |  |  |  |  |  |
| ggc | cca | gat | ctt | gag | ccc | ctc | atc | aag | gag | att | gtc | cgg | cgc | aat | atc | 864 |
| Gly | Pro | Asp | Leu | Glu | Pro | Leu | Ile | Lys | Glu | Ile | Val | Arg | Arg | Asn | Ile |  |
|  |  |  | 275 |  |  |  | 280 |  |  |  | 285 |  |  |  |  |  |
| acg | ggc | aag | atc | tgg | ctg | gcc | agc | gag | gcc | tgg | gcc | agc | tcc | tcc | ctg | 912 |
| Thr | Gly | Lys | Ile | Trp | Leu | Ala | Ser | Glu | Ala | Trp | Ala | Ser | Ser | Ser | Leu |  |
|  | 290 |  |  |  | 295 |  |  |  | 300 |  |  |  |  |  |  |  |
| atc | gcc | atg | cct | cag | tac | ttc | cac | gtg | gtt | ggc | ggc | acc | att | gga | ttc | 960 |
| Ile | Ala | Met | Pro | Gln | Tyr | Phe | His | Val | Val | Gly | Gly | Thr | Ile | Gly | Phe |  |
| 305 |  |  |  | 310 |  |  |  | 315 |  |  |  | 320 |  |  |  |  |
| gct | ctg | aag | gct | ggg | cag | atc | cca | ggc | ttc | cgg | gaa | ttc | ctg | aag | aag | 1008 |
| Ala | Leu | Lys | Ala | Gly | Gln | Ile | Pro | Gly | Phe | Arg | Glu | Phe | Leu | Lys | Lys |  |
|  |  |  | 325 |  |  |  | 330 |  |  |  | 335 |  |  |  |  |  |
| gtc | cat | ccc | agg | aag | tct | gtc | cac | aat | ggt | ttt | gcc | aag | gag | ttt | tgg | 1056 |
| Val | His | Pro | Arg | Lys | Ser | Val | His | Asn | Gly | Phe | Ala | Lys | Glu | Phe | Trp |  |
|  |  | 340 |  |  |  | 345 |  |  |  | 350 |  |  |  |  |  |  |
| gaa | gaa | aca | ttt | aac | tgc | cac | ctc | caa | gaa | ggt | gca | aaa | gga | cct | tta | 1104 |
| Glu | Glu | Thr | Phe | Asn | Cys | His | Leu | Gln | Glu | Gly | Ala | Lys | Gly | Pro | Leu |  |
|  | 355 |  |  |  | 360 |  |  |  | 365 |  |  |  |  |  |  |  |
| cct | gtg | gac | acc | ttt | ctg | aga | ggt | cac | gaa | gaa | agt | ggc | gac | agg | ttt | 1152 |
| Pro | Val | Asp | Thr | Phe | Leu | Arg | Gly | His | Glu | Glu | Ser | Gly | Asp | Arg | Phe |  |
| 370 |  |  |  | 375 |  |  |  | 380 |  |  |  |  |  |  |  |  |
| agc | aac | agc | tcg | aca | gcc | ttc | cga | ccc | ctc | tgt | aca | ggg | gat | gag | aac | 1200 |
| Ser | Asn | Ser | Ser | Thr | Ala | Phe | Arg | Pro | Leu | Cys | Thr | Gly | Asp | Glu | Asn |  |
| 385 |  |  |  | 390 |  |  |  | 395 |  |  |  | 400 |  |  |  |  |
| atc | agc | agt | gtc | gag | acc | cct | tac | ata | gat | tac | acg | cat | tta | cgg | ata | 1248 |
| Ile | Ser | Ser | Val | Glu | Thr | Pro | Tyr | Ile | Asp | Tyr | Thr | His | Leu | Arg | Ile |  |
|  |  |  |  | 405 |  |  |  | 410 |  |  |  | 415 |  |  |  |  |
| tcc | tac | aat | gtg | tac | tta | gca | gtc | tac | tcc | att | gcc | cac | gcc | ttg | caa | 1296 |
| Ser | Tyr | Asn | Val | Tyr | Leu | Ala | Val | Tyr | Ser | Ile | Ala | His | Ala | Leu | Gln |  |
|  |  |  | 420 |  |  |  | 425 |  |  |  | 430 |  |  |  |  |  |
| gat | ata | tat | acc | tgc | tta | cct | ggg | aga | ggg | ctc | ttc | acc | aat | ggc | tcc | 1344 |
| Asp | Ile | Tyr | Thr | Cys | Leu | Pro | Gly | Arg | Gly | Leu | Phe | Thr | Asn | Gly | Ser |  |
|  |  | 435 |  |  |  | 440 |  |  |  | 445 |  |  |  |  |  |  |
| tgt | gca | gac | atc | aag | aaa | gtt | gag | gcg | tgg | cag | gtc | ctg | aag | cac | cta | 1392 |
| Cys | Ala | Asp | Ile | Lys | Lys | Val | Glu | Ala | Trp | Gln | Val | Leu | Lys | His | Leu |  |
| 450 |  |  |  | 455 |  |  |  | 460 |  |  |  |  |  |  |  |  |
| cgg | cat | cta | aac | ttt | aca | aac | aat | atg | ggg | gag | cag | gtg | acc | ttt | gat | 1440 |
| Arg | His | Leu | Asn | Phe | Thr | Asn | Asn | Met | Gly | Glu | Gln | Val | Thr | Phe | Asp |  |
| 465 |  |  |  | 470 |  |  |  | 475 |  |  |  | 480 |  |  |  |  |
| gag | tgt | ggt | gac | ctg | gtg | ggg | aac | tat | tcc | atc | atc | aac | tgg | cac | ctc | 1488 |
| Glu | Cys | Gly | Asp | Leu | Val | Gly | Asn | Tyr | Ser | Ile | Ile | Asn | Trp | His | Leu |  |
|  |  |  | 485 |  |  |  | 490 |  |  |  | 495 |  |  |  |  |  |
| tcc | cca | gag | gat | ggc | tcc | atc | gtg | ttt | aag | gaa | gtc | ggg | tat | tac | aac | 1536 |
| Ser | Pro | Glu | Asp | Gly | Ser | Ile | Val | Phe | Lys | Glu | Val | Gly | Tyr | Tyr | Asn |  |
|  | 500 |  |  |  | 505 |  |  |  | 510 |  |  |  |  |  |  |  |
| gtc | tat | gcc | aag | aag | gga | gaa | aga | ctc | ttc | atc | aac | gag | gag | aaa | atc | 1584 |
| Val | Tyr | Ala | Lys | Lys | Gly | Glu | Arg | Leu | Phe | Ile | Asn | Glu | Glu | Lys | Ile |  |
|  | 515 |  |  |  | 520 |  |  |  | 525 |  |  |  |  |  |  |  |
| ctg | tgg | agt | ggg | ttc | tcc | agg | gag | gtg | ccc | ttc | tcc | aac | tgc | agc | cga | 1632 |
| Leu | Trp | Ser | Gly | Phe | Ser | Arg | Glu | Val | Pro | Phe | Ser | Asn | Cys | Ser | Arg |  |

-continued

```
               530                 535                 540
gac tgc ctg gca ggg acc agg aaa ggg atc att gag ggg gag ccc acc    1680
Asp Cys Leu Ala Gly Thr Arg Lys Gly Ile Ile Glu Gly Glu Pro Thr
545                 550                 555                 560 tgc tgc ttt gag tgt gtg gag tgt cct gat ggg gag tat agt gat gag    1728
Cys Cys Phe Glu Cys Val Glu Cys Pro Asp Gly Glu Tyr Ser Asp Glu
                565                 570                 575 aca gat gcc agt gcc tgt aac aag tgc cca gat gac ttc tgg tcc aat    1776
Thr Asp Ala Ser Ala Cys Asn Lys Cys Pro Asp Asp Phe Trp Ser Asn
            580                 585                 590 gag aac cac acc tcc tgc att gcc aag cgt acg cgg ttc ctg gca tgg    1824
Glu Asn His Thr Ser Cys Ile Ala Lys Arg Thr Arg Phe Leu Ala Trp
        595                 600                 605 ggc gag ccg gct gtg ctg ctg ctc ctg ctg agc ctg gcg ctg    1872
Gly Glu Pro Ala Val Leu Leu Leu Leu Leu Leu Ser Leu Ala Leu
    610                 615                 620 ggc ctt gtg ctg gct gct ttg ggg ctg ttc gtt cac cat cgg gac agc    1920
Gly Leu Val Leu Ala Ala Leu Gly Leu Phe Val His His Arg Asp Ser
625                 630                 635                 640 cca ctg gtt cag gcc tcg ggg ggg ccc ctg gcc tgc ttt ggc ctg gtg    1968
Pro Leu Val Gln Ala Ser Gly Gly Pro Leu Ala Cys Phe Gly Leu Val
                645                 650                 655 tgc ctg ggc ctg gtc tgc ctc agc gtc ctc ctg ttc cct ggc cag ccc    2016
Cys Leu Gly Leu Val Cys Leu Ser Val Leu Leu Phe Pro Gly Gln Pro
            660                 665                 670 agc cct gcc cga tgc ctg gcc cag cag ccc ttg tcc cac ctc ccg ctc    2064
Ser Pro Ala Arg Cys Leu Ala Gln Gln Pro Leu Ser His Leu Pro Leu
        675                 680                 685 acg ggc tgc ctg agc aca ctc ttc ctg cag gcg gcc gag atc ttc gtg    2112
Thr Gly Cys Leu Ser Thr Leu Phe Leu Gln Ala Ala Glu Ile Phe Val
    690                 695                 700 gag tca gaa ctg cct ctg agc tgg gca gac cgg ctg agt ggc tgc ctg    2160
Glu Ser Glu Leu Pro Leu Ser Trp Ala Asp Arg Leu Ser Gly Cys Leu
705                 710                 715                 720 cgg ggg ccc tgg gcc tgg ctg gtg gtg ctg ctg gcc atg ctg gtg gag    2208
Arg Gly Pro Trp Ala Trp Leu Val Val Leu Leu Ala Met Leu Val Glu
                725                 730                 735 gtc gca ctg tgc acc tgg tac ctg gtg gcc ttc ccg ccg gag gtg gtg    2256
Val Ala Leu Cys Thr Trp Tyr Leu Val Ala Phe Pro Pro Glu Val Val
            740                 745                 750 acg gac tgg cac atg ctg ccc acg gag gcg ctg gtg cac tgc cgc aca    2304
Thr Asp Trp His Met Leu Pro Thr Glu Ala Leu Val His Cys Arg Thr
        755                 760                 765 cgc tcc tgg gtc agc ttc ggc cta gcg cac gcc acc aat gcc acg ctg    2352
Arg Ser Trp Val Ser Phe Gly Leu Ala His Ala Thr Asn Ala Thr Leu
    770                 775                 780 gcc ttt ctc tgc ttc ctg ggc act ttc ctg gtg cgg agc cag ccg ggc    2400
Ala Phe Leu Cys Phe Leu Gly Thr Phe Leu Val Arg Ser Gln Pro Gly
785                 790                 795                 800 cgc tac aac cgt gcc cgt ggc ctc acc ttt gcc atg ctg gcc tac ttc    2448
Arg Tyr Asn Arg Ala Arg Gly Leu Thr Phe Ala Met Leu Ala Tyr Phe
                805                 810                 815 atc acc tgg gtc tcc ttt gtg ccc ctc ctg gcc aat gtg cag gtg gtc    2496
Ile Thr Trp Val Ser Phe Val Pro Leu Leu Ala Asn Val Gln Val Val
            820                 825                 830 ctc agg ccc gcc gtg cag atg ggc gcc ctc ctg ctc tgt gtc ctg ggc    2544
Leu Arg Pro Ala Val Gln Met Gly Ala Leu Leu Leu Cys Val Leu Gly
        835                 840                 845 atc ctg gct gcc ttc cac ctg ccc agg tgt tac ctg ctc atg cgg cag    2592
Ile Leu Ala Ala Phe His Leu Pro Arg Cys Tyr Leu Leu Met Arg Gln
```

```
                        850                 855                 860
cca ggg ctc aac acc ccc gag ttc ttc ctg gga ggg ggc cct ggg gat      2640
Pro Gly Leu Asn Thr Pro Glu Phe Phe Leu Gly Gly Gly Pro Gly Asp
865                 870                 875                 880 gcc caa ggc cag aat gac ggg aac aca gga aat cag ggg aaa cat gag      2688
Ala Gln Gly Gln Asn Asp Gly Asn Thr Gly Asn Gln Gly Lys His Glu
                885                 890                 895

<210> SEQ ID NO 4
<211> LENGTH: 896
<212> TYPE: PRT
<213> ORGANISM: human

<400> SEQUENCE: 4

Met Ala Phe Tyr Ser Cys Cys Trp Val Leu Leu Ala Leu Thr Trp His
1               5                   10                  15

Thr Ser Ala Tyr Gly Pro Asp Gln Arg Ala Gln Lys Lys Gly Asp Ile
            20                  25                  30

Ile Leu Gly Gly Leu Phe Pro Ile His Phe Gly Val Ala Ala Lys Asp
        35                  40                  45

Gln Asp Leu Lys Ser Arg Pro Glu Ser Val Glu Cys Ile Arg Tyr Asn
50                  55                  60

Phe Arg Gly Phe Arg Trp Leu Gln Ala Met Ile Phe Ala Ile Glu Glu
65                  70                  75                  80

Ile Asn Ser Ser Pro Ala Leu Leu Pro Asn Leu Thr Leu Gly Tyr Arg
                85                  90                  95

Ile Phe Asp Thr Cys Asn Thr Val Ser Lys Ala Leu Glu Ala Thr Leu
            100                 105                 110

Ser Phe Val Ala Gln Asn Lys Ile Asp Ser Leu Asn Leu Asp Glu Phe
        115                 120                 125

Cys Asn Cys Ser Glu His Ile Pro Ser Thr Ile Ala Val Val Gly Ala
130                 135                 140

Thr Gly Ser Gly Val Ser Thr Ala Val Ala Asn Leu Leu Gly Leu Phe
145                 150                 155                 160

Tyr Ile Pro Gln Val Ser Tyr Ala Ser Ser Ser Arg Leu Leu Ser Asn
                165                 170                 175

Lys Asn Gln Phe Lys Ser Phe Leu Arg Thr Ile Pro Asn Asp Glu His
            180                 185                 190

Gln Ala Thr Ala Met Ala Asp Ile Ile Glu Tyr Phe Arg Trp Asn Trp
        195                 200                 205

Val Gly Thr Ile Ala Ala Asp Asp Asp Tyr Gly Arg Pro Gly Ile Glu
210                 215                 220

Lys Phe Arg Glu Glu Ala Glu Glu Arg Asp Ile Cys Ile Asp Phe Ser
225                 230                 235                 240

Glu Leu Ile Ser Gln Tyr Ser Asp Glu Glu Ile Gln His Val Val
                245                 250                 255

Glu Val Ile Gln Asn Ser Thr Ala Lys Val Ile Val Val Phe Ser Ser
            260                 265                 270

Gly Pro Asp Leu Glu Pro Leu Ile Lys Glu Ile Val Arg Arg Asn Ile
        275                 280                 285

Thr Gly Lys Ile Trp Leu Ala Ser Glu Ala Trp Ala Ser Ser Ser Leu
290                 295                 300

Ile Ala Met Pro Gln Tyr Phe His Val Val Gly Gly Thr Ile Gly Phe
305                 310                 315                 320

Ala Leu Lys Ala Gly Gln Ile Pro Gly Phe Arg Glu Phe Leu Lys Lys
                325                 330                 335
```

```
Val His Pro Arg Lys Ser Val His Asn Gly Phe Ala Lys Glu Phe Trp
            340                 345                 350
Glu Glu Thr Phe Asn Cys His Leu Gln Glu Gly Ala Lys Gly Pro Leu
            355                 360                 365
Pro Val Asp Thr Phe Leu Arg Gly His Glu Glu Ser Gly Asp Arg Phe
370                 375                 380
Ser Asn Ser Ser Thr Ala Phe Arg Pro Leu Cys Thr Gly Asp Glu Asn
385                 390                 395                 400
Ile Ser Ser Val Glu Thr Pro Tyr Ile Asp Tyr Thr His Leu Arg Ile
                405                 410                 415
Ser Tyr Asn Val Tyr Leu Ala Val Tyr Ser Ile Ala His Ala Leu Gln
                420                 425                 430
Asp Ile Tyr Thr Cys Leu Pro Gly Arg Gly Leu Phe Thr Asn Gly Ser
                435                 440                 445
Cys Ala Asp Ile Lys Lys Val Glu Ala Trp Gln Val Leu Lys His Leu
            450                 455                 460
Arg His Leu Asn Phe Thr Asn Asn Met Gly Glu Gln Val Thr Phe Asp
465                 470                 475                 480
Glu Cys Gly Asp Leu Val Gly Asn Tyr Ser Ile Ile Asn Trp His Leu
                485                 490                 495
Ser Pro Glu Asp Gly Ser Ile Val Phe Lys Glu Val Gly Tyr Tyr Asn
                500                 505                 510
Val Tyr Ala Lys Lys Gly Glu Arg Leu Phe Ile Asn Glu Glu Lys Ile
                515                 520                 525
Leu Trp Ser Gly Phe Ser Arg Glu Val Pro Phe Ser Asn Cys Ser Arg
            530                 535                 540
Asp Cys Leu Ala Gly Thr Arg Lys Gly Ile Ile Glu Gly Glu Pro Thr
545                 550                 555                 560
Cys Cys Phe Glu Cys Val Glu Cys Pro Asp Gly Glu Tyr Ser Asp Glu
                565                 570                 575
Thr Asp Ala Ser Ala Cys Asn Lys Cys Pro Asp Asp Phe Trp Ser Asn
            580                 585                 590
Glu Asn His Thr Ser Cys Ile Ala Lys Arg Thr Arg Phe Leu Ala Trp
            595                 600                 605
Gly Glu Pro Ala Val Leu Leu Leu Leu Leu Leu Leu Ser Leu Ala Leu
610                 615                 620
Gly Leu Val Leu Ala Ala Leu Gly Leu Phe Val His His Arg Asp Ser
625                 630                 635                 640
Pro Leu Val Gln Ala Ser Gly Gly Pro Leu Ala Cys Phe Gly Leu Val
                645                 650                 655
Cys Leu Gly Leu Val Cys Leu Ser Val Leu Leu Phe Pro Gly Gln Pro
            660                 665                 670
Ser Pro Ala Arg Cys Leu Ala Gln Gln Pro Leu Ser His Leu Pro Leu
            675                 680                 685
Thr Gly Cys Leu Ser Thr Leu Phe Leu Gln Ala Ala Glu Ile Phe Val
            690                 695                 700
Glu Ser Glu Leu Pro Leu Ser Trp Ala Asp Arg Leu Ser Gly Cys Leu
705                 710                 715                 720
Arg Gly Pro Trp Ala Trp Leu Val Val Leu Leu Ala Met Leu Val Glu
                725                 730                 735
Val Ala Leu Cys Thr Trp Tyr Leu Val Ala Phe Pro Pro Glu Val Val
            740                 745                 750
Thr Asp Trp His Met Leu Pro Thr Glu Ala Leu Val His Cys Arg Thr
```

```
                755                 760                 765
Arg Ser Trp Val Ser Phe Gly Leu Ala His Ala Thr Asn Ala Thr Leu
    770                 775                 780

Ala Phe Leu Cys Phe Leu Gly Thr Phe Leu Val Arg Ser Gln Pro Gly
785                 790                 795                 800

Arg Tyr Asn Arg Ala Arg Gly Leu Thr Phe Ala Met Leu Ala Tyr Phe
                805                 810                 815

Ile Thr Trp Val Ser Phe Val Pro Leu Leu Ala Asn Val Gln Val Val
            820                 825                 830

Leu Arg Pro Ala Val Gln Met Gly Ala Leu Leu Leu Cys Val Leu Gly
        835                 840                 845

Ile Leu Ala Ala Phe His Leu Pro Arg Cys Tyr Leu Leu Met Arg Gln
    850                 855                 860

Pro Gly Leu Asn Thr Pro Glu Phe Phe Leu Gly Gly Gly Pro Gly Asp
865                 870                 875                 880

Ala Gln Gly Gln Asn Asp Gly Asn Thr Gly Asn Gln Gly Lys His Glu
                885                 890                 895

<210> SEQ ID NO 5
<211> LENGTH: 51
<212> TYPE: DNA
<213> ORGANISM: herpes simplex virus
<220> FEATURE:
<221> NAME/KEY: CDS
<222> LOCATION: (1)..(51)

<400> SEQUENCE: 5 tgc ggc cgc cag cct gaa ctc gct cct gaa gac ccg gaa gat taa tct    48
Cys Gly Arg Gln Pro Glu Leu Ala Pro Glu Asp Pro Glu Asp     Ser
1               5                   10                      15 aga                                                                51
Arg

<210> SEQ ID NO 6
<211> LENGTH: 14
<212> TYPE: PRT
<213> ORGANISM: herpes simplex virus

<400> SEQUENCE: 6

Cys Gly Arg Gln Pro Glu Leu Ala Pro Glu Asp Pro Glu Asp
1               5                   10

<210> SEQ ID NO 7
<211> LENGTH: 2526
<212> TYPE: DNA
<213> ORGANISM: human
<220> FEATURE:
<221> NAME/KEY: CDS
<222> LOCATION: (1)..(2526)

<400> SEQUENCE: 7 atg ctg ctc tgc acg gct cgc ctg gtc ggc ctg cag ctt ctc att tcc    48
Met Leu Leu Cys Thr Ala Arg Leu Val Gly Leu Gln Leu Leu Ile Ser
1               5                   10                  15 tgc tgc tgg gcc ttt gcc tgc cat agc acg gag tct tct cct gac ttc    96
Cys Cys Trp Ala Phe Ala Cys His Ser Thr Glu Ser Ser Pro Asp Phe
            20                  25                  30 acc ctc ccc gga gat tac ctc ctg gca ggc ctg ttc cct ctc cat tct    144
Thr Leu Pro Gly Asp Tyr Leu Leu Ala Gly Leu Phe Pro Leu His Ser
        35                  40                  45 ggc tgt ctg cag gtg agg cac aga ccc gag gtg acc ctg tgt gac agg    192
Gly Cys Leu Gln Val Arg His Arg Pro Glu Val Thr Leu Cys Asp Arg
```

```
                    50                  55                  60
tct tgt agc ttc aat gag cat ggc tac cac ctc ttc cag gct atg cgg        240
Ser Cys Ser Phe Asn Glu His Gly Tyr His Leu Phe Gln Ala Met Arg
 65                  70                  75                  80 ctt ggg gtt gag gag ata aac aac tcc acg gcc ctg ctg ccc aac atc        288
Leu Gly Val Glu Glu Ile Asn Asn Ser Thr Ala Leu Leu Pro Asn Ile
                     85                  90                  95 acc ctg ggg tac cag ctg tat gat gtg tgt tct gac tct gcc aat gtg        336
Thr Leu Gly Tyr Gln Leu Tyr Asp Val Cys Ser Asp Ser Ala Asn Val
                100                 105                 110 tat gcc acg ctg aga gtg ctc tcc ctg cca ggg caa cac cac ata gag        384
Tyr Ala Thr Leu Arg Val Leu Ser Leu Pro Gly Gln His His Ile Glu
            115                 120                 125 ctc caa gga gac ctt ctc cac tat tcc cct acg gtg ctg gca gtg att        432
Leu Gln Gly Asp Leu Leu His Tyr Ser Pro Thr Val Leu Ala Val Ile
130                 135                 140 ggg cct gac agc acc aac cgt gct gcc acc aca gcc gcc ctg ctg agc        480
Gly Pro Asp Ser Thr Asn Arg Ala Ala Thr Thr Ala Ala Leu Leu Ser
145                 150                 155                 160 cct ttc ctg gtg ccc atg att agc tat gcg gcc agc agc gag acg ctc        528
Pro Phe Leu Val Pro Met Ile Ser Tyr Ala Ala Ser Ser Glu Thr Leu
                165                 170                 175 agc gtg aag cgg cag tat ccc tct ttc ctg cgc acc atc ccc aat gac        576
Ser Val Lys Arg Gln Tyr Pro Ser Phe Leu Arg Thr Ile Pro Asn Asp
                180                 185                 190 aag tac cag gtg gag acc atg gtg ctg ctg ctg cag aag ttc ggg tgg        624
Lys Tyr Gln Val Glu Thr Met Val Leu Leu Leu Gln Lys Phe Gly Trp
            195                 200                 205 acc tgg atc tct ctg gtt ggc agc agt gac gac tat ggg cag cta ggg        672
Thr Trp Ile Ser Leu Val Gly Ser Ser Asp Asp Tyr Gly Gln Leu Gly
210                 215                 220 gtg cag gca ctg gag aac cag gcc act ggt cag ggg atc tgc att gct        720
Val Gln Ala Leu Glu Asn Gln Ala Thr Gly Gln Gly Ile Cys Ile Ala
225                 230                 235                 240 ttc aag gac atc atg ccc ttc tct gcc cag gtg ggc gat gag agg atg        768
Phe Lys Asp Ile Met Pro Phe Ser Ala Gln Val Gly Asp Glu Arg Met
                245                 250                 255 cag tgc ctc atg cgc cac ctg gcc cag gcc ggg gcc acc gtc gtg gtt        816
Gln Cys Leu Met Arg His Leu Ala Gln Ala Gly Ala Thr Val Val Val
                260                 265                 270 gtt ttt tcc agc cgg cag ttg gcc agg gtg ttt ttc gag tcc gtg gtg        864
Val Phe Ser Ser Arg Gln Leu Ala Arg Val Phe Phe Glu Ser Val Val
            275                 280                 285 ctg acc aac ctg act ggc aag gtg tgg gtc gcc tca gaa gcc tgg gcc        912
Leu Thr Asn Leu Thr Gly Lys Val Trp Val Ala Ser Glu Ala Trp Ala
290                 295                 300 ctc tcc agg cac atc act ggg gtg ccc ggg atc cag cgc att ggg atg        960
Leu Ser Arg His Ile Thr Gly Val Pro Gly Ile Gln Arg Ile Gly Met
305                 310                 315                 320 gtg ctg ggc gtg gcc atc cag aag agg gct gtc cct ggc ctg aag gcg       1008
Val Leu Gly Val Ala Ile Gln Lys Arg Ala Val Pro Gly Leu Lys Ala
                325                 330                 335 ttt gaa gaa gcc tat gcc cgg gca gac aag aag gcc cct agg cct tgc       1056
Phe Glu Glu Ala Tyr Ala Arg Ala Asp Lys Lys Ala Pro Arg Pro Cys
                340                 345                 350 cac aag ggc tcc tgg tgc agc agc aat cag ctc tgc aga gaa tgc caa       1104
His Lys Gly Ser Trp Cys Ser Ser Asn Gln Leu Cys Arg Glu Cys Gln
            355                 360                 365 gct ttc atg gca cac acg atg ccc aag ctc aaa gcc ttc tcc atg agt       1152
Ala Phe Met Ala His Thr Met Pro Lys Leu Lys Ala Phe Ser Met Ser
```

```
                    370                 375                 380
tct gcc tac aac gca tac cgg gct gtg tat gcg gtg gcc cat ggc ctc    1200
Ser Ala Tyr Asn Ala Tyr Arg Ala Val Tyr Ala Val Ala His Gly Leu
385                 390                 395                 400 cac cag ctc ctg ggc tgt gcc tct gga gct tgt tcc agg ggc cga gtc    1248
His Gln Leu Leu Gly Cys Ala Ser Gly Ala Cys Ser Arg Gly Arg Val
            405                 410                 415 tac ccc tgg cag ctt ttg gag cag atc cac aag gtg cat ttc ctt cta    1296
Tyr Pro Trp Gln Leu Leu Glu Gln Ile His Lys Val His Phe Leu Leu
    420                 425                 430 cac aag gac act gtg gcg ttt aat gac aac aga gat ccc ctc agt agc    1344
His Lys Asp Thr Val Ala Phe Asn Asp Asn Arg Asp Pro Leu Ser Ser
435                 440                 445 tat aac ata att gcc tgg gac tgg aat gga ccc aag tgg acc ttc acg    1392
Tyr Asn Ile Ile Ala Trp Asp Trp Asn Gly Pro Lys Trp Thr Phe Thr
            450                 455                 460 gtc ctc ggt tcc tcc aca tgg tct cca gtt cag cta aac ata aat gag    1440
Val Leu Gly Ser Ser Thr Trp Ser Pro Val Gln Leu Asn Ile Asn Glu
465                 470                 475                 480 acc aaa atc cag tgg cac gga aag gac aac cag gtg cct aag tct gtg    1488
Thr Lys Ile Gln Trp His Gly Lys Asp Asn Gln Val Pro Lys Ser Val
                485                 490                 495 tgt tcc agc gac tgt ctt gaa ggg cac cag cga gtg gtt acg ggt ttc    1536
Cys Ser Ser Asp Cys Leu Glu Gly His Gln Arg Val Val Thr Gly Phe
            500                 505                 510 cat cac tgc tgc ttt gag tgt gtg ccc tgt ggg gct ggg acc ttc ctc    1584
His His Cys Cys Phe Glu Cys Val Pro Cys Gly Ala Gly Thr Phe Leu
    515                 520                 525 aac aag agt gac ctc tac aga tgc cag cct tgt ggg aaa gaa gag tgg    1632
Asn Lys Ser Asp Leu Tyr Arg Cys Gln Pro Cys Gly Lys Glu Glu Trp
530                 535                 540 gca cct gag gga agc cag acc tgc ttc ccg cgc act gtg gtt ttt ttg    1680
Ala Pro Glu Gly Ser Gln Thr Cys Phe Pro Arg Thr Val Val Phe Leu
545                 550                 555                 560 gct ttg cgt gag cac acc tct tgg gtg ctg ctg gca gct aac acg ctg    1728
Ala Leu Arg Glu His Thr Ser Trp Val Leu Leu Ala Ala Asn Thr Leu
                565                 570                 575 ctg ctg ctg ctg ctg ctt ggg act gct ggc ctg ttt gcc tgg cac cta    1776
Leu Leu Leu Leu Leu Leu Gly Thr Ala Gly Leu Phe Ala Trp His Leu
            580                 585                 590 gac acc cct gtg gtg agg tca gca ggg ggc cgc ctg tgc ttt ctt atg    1824
Asp Thr Pro Val Val Arg Ser Ala Gly Gly Arg Leu Cys Phe Leu Met
    595                 600                 605 ctg ggc tcc ctg gca gca ggt agt ggc agc ctc tat ggc ttc ttt ggg    1872
Leu Gly Ser Leu Ala Ala Gly Ser Gly Ser Leu Tyr Gly Phe Phe Gly
610                 615                 620 gaa ccc aca agg cct gcg tgc ttg cta cgc cag gcc ctc ttt gcc ctt    1920
Glu Pro Thr Arg Pro Ala Cys Leu Leu Arg Gln Ala Leu Phe Ala Leu
625                 630                 635                 640 ggt ttc acc atc ttc ctg tcc tgc ctg aca gtt cgc tca ttc caa cta    1968
Gly Phe Thr Ile Phe Leu Ser Cys Leu Thr Val Arg Ser Phe Gln Leu
                645                 650                 655 atc atc atc ttc aag ttt tcc acc aag gta cct aca ttc tac cac gcc    2016
Ile Ile Ile Phe Lys Phe Ser Thr Lys Val Pro Thr Phe Tyr His Ala
            660                 665                 670 tgg gtc caa aac cac ggt gct ggc ctg ttt gtg atg atc agc tca gcg    2064
Trp Val Gln Asn His Gly Ala Gly Leu Phe Val Met Ile Ser Ser Ala
    675                 680                 685 gcc cag ctg ctt atc tgt cta act tgg ctg gtg gtg tgg acc cca ctg    2112
Ala Gln Leu Leu Ile Cys Leu Thr Trp Leu Val Val Trp Thr Pro Leu
```

```
                    690                   695                   700
cct gct agg gaa tac cag cgc ttc ccc cat ctg gtg atg ctt gag tgc    2160
Pro Ala Arg Glu Tyr Gln Arg Phe Pro His Leu Val Met Leu Glu Cys
705                 710                 715                 720 aca gag acc aac tcc ctg ggc ttc ata ctg gcc ttc ctc tac aat ggc    2208
Thr Glu Thr Asn Ser Leu Gly Phe Ile Leu Ala Phe Leu Tyr Asn Gly
                725                 730                 735 ctc ctc tcc atc agt gcc ttt gcc tgc agc tac ctg ggt aag gac ttg    2256
Leu Leu Ser Ile Ser Ala Phe Ala Cys Ser Tyr Leu Gly Lys Asp Leu
            740                 745                 750 cca gag aac tac aac gag gcc aaa tgt gtc acc ttc agc ctc ctc ttc    2304
Pro Glu Asn Tyr Asn Glu Ala Lys Cys Val Thr Phe Ser Leu Leu Phe
        755                 760                 765 aac ttc gtg tcc tgg atc gcc ttc ttc acc acg gcc agc gtc tac gac    2352
Asn Phe Val Ser Trp Ile Ala Phe Phe Thr Thr Ala Ser Val Tyr Asp
    770                 775                 780 ggc aag tac ctg cct gcg gcc aac atg atg gct ggg ctg agc agc ctg    2400
Gly Lys Tyr Leu Pro Ala Ala Asn Met Met Ala Gly Leu Ser Ser Leu
785                 790                 795                 800 agc agc ggc ttc ggt ggg tat ttt ctg cct aag tgc tac gtg atc ctc    2448
Ser Ser Gly Phe Gly Gly Tyr Phe Leu Pro Lys Cys Tyr Val Ile Leu
                805                 810                 815 tgc cgc cca gac ctc aac agc aca gag cac ttc cag gcc tcc att cag    2496
Cys Arg Pro Asp Leu Asn Ser Thr Glu His Phe Gln Ala Ser Ile Gln
            820                 825                 830 gac tac acg agg cgc tgc ggc tcc acc tga                            2526
Asp Tyr Thr Arg Arg Cys Gly Ser Thr
        835                 840

<210> SEQ ID NO 8
<211> LENGTH: 841
<212> TYPE: PRT
<213> ORGANISM: human

<400> SEQUENCE: 8

Met Leu Leu Cys Thr Ala Arg Leu Val Gly Leu Gln Leu Leu Ile Ser
1               5                   10                  15

Cys Cys Trp Ala Phe Ala Cys His Ser Thr Glu Ser Ser Pro Asp Phe
            20                  25                  30

Thr Leu Pro Gly Asp Tyr Leu Leu Ala Gly Leu Phe Pro Leu His Ser
        35                  40                  45

Gly Cys Leu Gln Val Arg His Arg Pro Glu Val Thr Leu Cys Asp Arg
    50                  55                  60

Ser Cys Ser Phe Asn Glu His Gly Tyr His Leu Phe Gln Ala Met Arg
65                  70                  75                  80

Leu Gly Val Glu Glu Ile Asn Asn Ser Thr Ala Leu Leu Pro Asn Ile
                85                  90                  95

Thr Leu Gly Tyr Gln Leu Tyr Asp Val Cys Ser Asp Ser Ala Asn Val
            100                 105                 110

Tyr Ala Thr Leu Arg Val Leu Ser Leu Pro Gly Gln His His Ile Glu
        115                 120                 125

Leu Gln Gly Asp Leu Leu His Tyr Ser Pro Thr Val Leu Ala Val Ile
    130                 135                 140

Gly Pro Asp Ser Thr Asn Arg Ala Ala Thr Thr Ala Ala Leu Leu Ser
145                 150                 155                 160

Pro Phe Leu Val Pro Met Ile Ser Tyr Ala Ala Ser Ser Glu Thr Leu
                165                 170                 175

Ser Val Lys Arg Gln Tyr Pro Ser Phe Leu Arg Thr Ile Pro Asn Asp
```

-continued

```
            180                 185                 190
Lys Tyr Gln Val Glu Thr Met Val Leu Leu Gln Lys Phe Gly Trp
            195                 200                 205
Thr Trp Ile Ser Leu Val Gly Ser Ser Asp Tyr Gly Gln Leu Gly
            210                 215                 220
Val Gln Ala Leu Glu Asn Gln Ala Thr Gly Gln Gly Ile Cys Ile Ala
225                         230                         240
Phe Lys Asp Ile Met Pro Phe Ser Ala Gln Val Gly Asp Glu Arg Met
                    245                 250                 255
Gln Cys Leu Met Arg His Leu Ala Gln Ala Gly Ala Thr Val Val Val
                    260                 265                 270
Val Phe Ser Ser Arg Gln Leu Ala Arg Val Phe Phe Glu Ser Val Val
                    275                 280                 285
Leu Thr Asn Leu Thr Gly Lys Val Trp Val Ala Ser Glu Ala Trp Ala
            290                 295                 300
Leu Ser Arg His Ile Thr Gly Val Pro Gly Ile Gln Arg Ile Gly Met
305                         310                 315                 320
Val Leu Gly Val Ala Ile Gln Lys Arg Ala Val Pro Gly Leu Lys Ala
                            325                 330                 335
Phe Glu Glu Ala Tyr Ala Arg Ala Asp Lys Lys Ala Pro Arg Pro Cys
                    340                 345                 350
His Lys Gly Ser Trp Cys Ser Ser Asn Gln Leu Cys Arg Glu Cys Gln
            355                 360                 365
Ala Phe Met Ala His Thr Met Pro Lys Leu Lys Ala Phe Ser Met Ser
    370                 375                 380
Ser Ala Tyr Asn Ala Tyr Arg Ala Val Tyr Ala Val Ala His Gly Leu
385                 390                 395                 400
His Gln Leu Leu Gly Cys Ala Ser Gly Ala Cys Ser Arg Gly Arg Val
                405                 410                 415
Tyr Pro Trp Gln Leu Leu Glu Gln Ile His Lys Val His Phe Leu Leu
                    420                 425                 430
His Lys Asp Thr Val Ala Phe Asn Asp Asn Arg Asp Pro Leu Ser Ser
            435                 440                 445
Tyr Asn Ile Ile Ala Trp Asp Trp Asn Gly Pro Lys Trp Thr Phe Thr
    450                 455                 460
Val Leu Gly Ser Ser Thr Trp Ser Pro Val Gln Leu Asn Ile Asn Glu
465                 470                 475                 480
Thr Lys Ile Gln Trp His Gly Lys Asp Asn Gln Val Pro Lys Ser Val
                    485                 490                 495
Cys Ser Ser Asp Cys Leu Glu Gly His Gln Arg Val Val Thr Gly Phe
                500                 505                 510
His His Cys Cys Phe Glu Cys Val Pro Cys Gly Ala Gly Thr Phe Leu
            515                 520                 525
Asn Lys Ser Asp Leu Tyr Arg Cys Gln Pro Cys Gly Lys Glu Glu Trp
    530                 535                 540
Ala Pro Glu Gly Ser Gln Thr Cys Phe Pro Arg Thr Val Val Phe Leu
545                 550                 555                 560
Ala Leu Arg Glu His Thr Ser Trp Val Leu Leu Ala Ala Asn Thr Leu
                565                 570                 575
Leu Leu Leu Leu Leu Leu Gly Thr Ala Gly Leu Phe Ala Trp His Leu
            580                 585                 590
Asp Thr Pro Val Val Arg Ser Ala Gly Gly Arg Leu Cys Phe Leu Met
            595                 600                 605
```

-continued

```
Leu Gly Ser Leu Ala Ala Gly Ser Gly Ser Leu Tyr Gly Phe Phe Gly
            610             615                 620

Glu Pro Thr Arg Pro Ala Cys Leu Leu Arg Gln Ala Leu Phe Ala Leu
625                 630                 635                 640

Gly Phe Thr Ile Phe Leu Ser Cys Leu Thr Val Arg Ser Phe Gln Leu
                645                 650                 655

Ile Ile Ile Phe Lys Phe Ser Thr Lys Val Pro Thr Phe Tyr His Ala
            660                 665                 670

Trp Val Gln Asn His Gly Ala Gly Leu Phe Val Met Ile Ser Ser Ala
                675                 680                 685

Ala Gln Leu Leu Ile Cys Leu Thr Trp Leu Val Val Trp Thr Pro Leu
690                 695                 700

Pro Ala Arg Glu Tyr Gln Arg Phe Pro His Leu Val Met Leu Glu Cys
705                 710                 715                 720

Thr Glu Thr Asn Ser Leu Gly Phe Ile Leu Ala Phe Leu Tyr Asn Gly
                725                 730                 735

Leu Leu Ser Ile Ser Ala Phe Ala Cys Ser Tyr Leu Gly Lys Asp Leu
            740                 745                 750

Pro Glu Asn Tyr Asn Glu Ala Lys Cys Val Thr Phe Ser Leu Leu Phe
                755                 760                 765

Asn Phe Val Ser Trp Ile Ala Phe Phe Thr Thr Ala Ser Val Tyr Asp
            770                 775                 780

Gly Lys Tyr Leu Pro Ala Ala Asn Met Met Ala Gly Leu Ser Ser Leu
785                 790                 795                 800

Ser Ser Gly Phe Gly Gly Tyr Phe Leu Pro Lys Cys Tyr Val Ile Leu
                805                 810                 815

Cys Arg Pro Asp Leu Asn Ser Thr Glu His Phe Gln Ala Ser Ile Gln
            820                 825                 830

Asp Tyr Thr Arg Arg Cys Gly Ser Thr
                835                 840

<210> SEQ ID NO 9
<211> LENGTH: 2559
<212> TYPE: DNA
<213> ORGANISM: human
<220> FEATURE:
<221> NAME/KEY: CDS
<222> LOCATION: (1)..(2559)

<400> SEQUENCE: 9 atg ctg ggc cct gct gtc ctg ggc ctc agc ctc tgg gct ctc ctg cac      48
Met Leu Gly Pro Ala Val Leu Gly Leu Ser Leu Trp Ala Leu Leu His
1               5                   10                  15 cct ggg acg ggg gcc cca ttg tgc ctg tca cag caa ctt agg atg aag      96
Pro Gly Thr Gly Ala Pro Leu Cys Leu Ser Gln Gln Leu Arg Met Lys
            20                  25                  30 ggg gac tac gtg ctg ggg ggg ctg ttc ccc ctg ggc gag gcc gag gag     144
Gly Asp Tyr Val Leu Gly Gly Leu Phe Pro Leu Gly Glu Ala Glu Glu
        35                  40                  45 gct ggc ctc cgc agc cgg aca cgg ccc agc agc cct gtg tgc acc agg     192
Ala Gly Leu Arg Ser Arg Thr Arg Pro Ser Ser Pro Val Cys Thr Arg
    50                  55                  60 ttc tcc tca aac ggc ctg ctc tgg gca ctg gcc atg aaa atg gcc gtg     240
Phe Ser Ser Asn Gly Leu Leu Trp Ala Leu Ala Met Lys Met Ala Val
65                  70                  75                  80 gag gag atc aac aac aag tcg gat ctg ctg ccc ggg ctg cgc ctg ggc     288
Glu Glu Ile Asn Asn Lys Ser Asp Leu Leu Pro Gly Leu Arg Leu Gly
                85                  90                  95
```

| | | | | | | | | | | | | | | | | |
|---|---|---|---|---|---|---|---|---|---|---|---|---|---|---|---|---|
| tac | gac | ctc | ttt | gat | acg | tgc | tcg | gag | cct | gtg | gtg | gcc | atg | aag | ccc | 336 |
| Tyr | Asp | Leu | Phe | Asp | Thr | Cys | Ser | Glu | Pro | Val | Val | Ala | Met | Lys | Pro | |
| | | | 100 | | | | 105 | | | | 110 | | | | | |

| | | | | | | | | | | | | | | | | |
|---|---|---|---|---|---|---|---|---|---|---|---|---|---|---|---|---|
| agc | ctc | atg | ttc | ctg | gcc | aag | gca | ggc | agc | cgc | gac | atc | gcc | gcc | tac | 384 |
| Ser | Leu | Met | Phe | Leu | Ala | Lys | Ala | Gly | Ser | Arg | Asp | Ile | Ala | Ala | Tyr | |
| | | 115 | | | | | 120 | | | | | 125 | | | | |

| | | | | | | | | | | | | | | | | |
|---|---|---|---|---|---|---|---|---|---|---|---|---|---|---|---|---|
| tgc | aac | tac | acg | cag | tac | cag | ccc | cgt | gtg | ctg | gct | gtc | atc | ggg | ccc | 432 |
| Cys | Asn | Tyr | Thr | Gln | Tyr | Gln | Pro | Arg | Val | Leu | Ala | Val | Ile | Gly | Pro | |
| | 130 | | | | | 135 | | | | | 140 | | | | | |

| | | | | | | | | | | | | | | | | |
|---|---|---|---|---|---|---|---|---|---|---|---|---|---|---|---|---|
| cac | tcg | tca | gag | ctc | gcc | atg | gtc | acc | ggc | aag | ttc | ttc | agc | ttc | ttc | 480 |
| His | Ser | Ser | Glu | Leu | Ala | Met | Val | Thr | Gly | Lys | Phe | Phe | Ser | Phe | Phe | |
| 145 | | | | | 150 | | | | | 155 | | | | | 160 | |

| | | | | | | | | | | | | | | | | |
|---|---|---|---|---|---|---|---|---|---|---|---|---|---|---|---|---|
| ctc | atg | ccc | cag | gtc | agc | tac | ggt | gct | agc | atg | gag | ctg | ctg | agc | gcc | 528 |
| Leu | Met | Pro | Gln | Val | Ser | Tyr | Gly | Ala | Ser | Met | Glu | Leu | Leu | Ser | Ala | |
| | | | | 165 | | | | | 170 | | | | | 175 | | |

| | | | | | | | | | | | | | | | | |
|---|---|---|---|---|---|---|---|---|---|---|---|---|---|---|---|---|
| cgg | gag | acc | ttc | ccc | tcc | ttc | ttc | cgc | acc | gtg | ccc | agc | gac | cgt | gtg | 576 |
| Arg | Glu | Thr | Phe | Pro | Ser | Phe | Phe | Arg | Thr | Val | Pro | Ser | Asp | Arg | Val | |
| | | | 180 | | | | | 185 | | | | | 190 | | | |

| | | | | | | | | | | | | | | | | |
|---|---|---|---|---|---|---|---|---|---|---|---|---|---|---|---|---|
| cag | ctg | acg | gcc | gcc | gcg | gag | ctg | ctg | cag | gag | ttc | ggc | tgg | aac | tgg | 624 |
| Gln | Leu | Thr | Ala | Ala | Ala | Glu | Leu | Leu | Gln | Glu | Phe | Gly | Trp | Asn | Trp | |
| | | 195 | | | | | 200 | | | | | 205 | | | | |

| | | | | | | | | | | | | | | | | |
|---|---|---|---|---|---|---|---|---|---|---|---|---|---|---|---|---|
| gtg | gcc | gcc | ctg | ggc | agc | gac | gac | gag | tac | ggc | cgg | cag | ggc | ctg | agc | 672 |
| Val | Ala | Ala | Leu | Gly | Ser | Asp | Asp | Glu | Tyr | Gly | Arg | Gln | Gly | Leu | Ser | |
| | 210 | | | | | 215 | | | | | 220 | | | | | |

| | | | | | | | | | | | | | | | | |
|---|---|---|---|---|---|---|---|---|---|---|---|---|---|---|---|---|
| atc | ttc | tcg | gcc | ctg | gcc | gcg | gca | cgc | ggc | atc | tgc | atc | gcg | cac | gag | 720 |
| Ile | Phe | Ser | Ala | Leu | Ala | Ala | Ala | Arg | Gly | Ile | Cys | Ile | Ala | His | Glu | |
| 225 | | | | | 230 | | | | | 235 | | | | | 240 | |

| | | | | | | | | | | | | | | | | |
|---|---|---|---|---|---|---|---|---|---|---|---|---|---|---|---|---|
| ggc | ctg | gtg | ccg | ctg | ccc | cgt | gcc | gat | gac | tcg | cgg | ctg | ggg | aag | gtg | 768 |
| Gly | Leu | Val | Pro | Leu | Pro | Arg | Ala | Asp | Asp | Ser | Arg | Leu | Gly | Lys | Val | |
| | | | | 245 | | | | | 250 | | | | | 255 | | |

| | | | | | | | | | | | | | | | | |
|---|---|---|---|---|---|---|---|---|---|---|---|---|---|---|---|---|
| cag | gac | gtc | ctg | cac | cag | gtg | aac | cag | agc | agc | gtg | cag | gtg | gtg | ctg | 816 |
| Gln | Asp | Val | Leu | His | Gln | Val | Asn | Gln | Ser | Ser | Val | Gln | Val | Val | Leu | |
| | | | 260 | | | | | 265 | | | | | 270 | | | |

| | | | | | | | | | | | | | | | | |
|---|---|---|---|---|---|---|---|---|---|---|---|---|---|---|---|---|
| ctg | ttc | gcc | tcc | gtg | cac | gcc | gcc | cac | gcc | ctc | ttc | aac | tac | agc | atc | 864 |
| Leu | Phe | Ala | Ser | Val | His | Ala | Ala | His | Ala | Leu | Phe | Asn | Tyr | Ser | Ile | |
| | | 275 | | | | | 280 | | | | | 285 | | | | |

| | | | | | | | | | | | | | | | | |
|---|---|---|---|---|---|---|---|---|---|---|---|---|---|---|---|---|
| agc | agc | agg | ctc | tcg | ccc | aag | gtg | tgg | gtg | gcc | agc | gag | gcc | tgg | ctg | 912 |
| Ser | Ser | Arg | Leu | Ser | Pro | Lys | Val | Trp | Val | Ala | Ser | Glu | Ala | Trp | Leu | |
| | 290 | | | | | 295 | | | | | 300 | | | | | |

| | | | | | | | | | | | | | | | | |
|---|---|---|---|---|---|---|---|---|---|---|---|---|---|---|---|---|
| acc | tct | gac | ctg | gtc | atg | ggg | ctg | ccc | ggc | atg | gcc | cag | atg | ggc | acg | 960 |
| Thr | Ser | Asp | Leu | Val | Met | Gly | Leu | Pro | Gly | Met | Ala | Gln | Met | Gly | Thr | |
| 305 | | | | | 310 | | | | | 315 | | | | | 320 | |

| | | | | | | | | | | | | | | | | |
|---|---|---|---|---|---|---|---|---|---|---|---|---|---|---|---|---|
| gtg | ctt | ggc | ttc | ctc | cag | agg | ggt | gcc | cag | ctg | cac | gag | ttc | ccc | cag | 1008 |
| Val | Leu | Gly | Phe | Leu | Gln | Arg | Gly | Ala | Gln | Leu | His | Glu | Phe | Pro | Gln | |
| | | | | 325 | | | | | 330 | | | | | 335 | | |

| | | | | | | | | | | | | | | | | |
|---|---|---|---|---|---|---|---|---|---|---|---|---|---|---|---|---|
| tac | gtg | aag | acg | cac | ctg | gcc | ctg | gcc | acc | gac | ccg | gcc | ttc | tgc | tct | 1056 |
| Tyr | Val | Lys | Thr | His | Leu | Ala | Leu | Ala | Thr | Asp | Pro | Ala | Phe | Cys | Ser | |
| | | | 340 | | | | | 345 | | | | | 350 | | | |

| | | | | | | | | | | | | | | | | |
|---|---|---|---|---|---|---|---|---|---|---|---|---|---|---|---|---|
| gcc | ctg | ggc | gag | agg | gag | cag | ggt | ctg | gag | gag | gac | gtg | gtg | ggc | cag | 1104 |
| Ala | Leu | Gly | Glu | Arg | Glu | Gln | Gly | Leu | Glu | Glu | Asp | Val | Val | Gly | Gln | |
| | | 355 | | | | | 360 | | | | | 365 | | | | |

| | | | | | | | | | | | | | | | | |
|---|---|---|---|---|---|---|---|---|---|---|---|---|---|---|---|---|
| cgc | tgc | ccg | cag | tgt | gac | tgc | atc | acg | ctg | cag | aac | gtg | agc | gca | ggg | 1152 |
| Arg | Cys | Pro | Gln | Cys | Asp | Cys | Ile | Thr | Leu | Gln | Asn | Val | Ser | Ala | Gly | |
| | 370 | | | | | 375 | | | | | 380 | | | | | |

| | | | | | | | | | | | | | | | | |
|---|---|---|---|---|---|---|---|---|---|---|---|---|---|---|---|---|
| cta | aat | cac | cac | cag | acg | ttc | tct | gtc | tac | gca | gct | gtg | tat | agc | gtg | 1200 |
| Leu | Asn | His | His | Gln | Thr | Phe | Ser | Val | Tyr | Ala | Ala | Val | Tyr | Ser | Val | |
| 385 | | | | | 390 | | | | | 395 | | | | | 400 | |

| | | | | | | | | | | | | | | | | |
|---|---|---|---|---|---|---|---|---|---|---|---|---|---|---|---|---|
| gcc | cag | gcc | ctg | cac | aac | act | ctt | cag | tgc | aac | gcc | tca | ggc | tgc | ccc | 1248 |
| Ala | Gln | Ala | Leu | His | Asn | Thr | Leu | Gln | Cys | Asn | Ala | Ser | Gly | Cys | Pro | |
| | | | | 405 | | | | | 410 | | | | | 415 | | |

| | | |
|---|---|---|
| gcg cag gac ccc gtg aag ccc tgg cag ctc ctg gag aac atg tac aac<br>Ala Gln Asp Pro Val Lys Pro Trp Gln Leu Leu Glu Asn Met Tyr Asn<br>420                 425                 430 | | 1296 |
| ctg acc ttc cac gtg ggc ggg ctg ccg ctg cgg ttc gac agc agc gga<br>Leu Thr Phe His Val Gly Gly Leu Pro Leu Arg Phe Asp Ser Ser Gly<br>        435                 440                 445 | | 1344 |
| aac gtg gac atg gag tac gac ctg aag ctg tgg gtg tgg cag ggc tca<br>Asn Val Asp Met Glu Tyr Asp Leu Lys Leu Trp Val Trp Gln Gly Ser<br>450                 455                 460 | | 1392 |
| gtg ccc agg ctc cac gac gtg ggc agg ttc aac ggc agc ctc agg aca<br>Val Pro Arg Leu His Asp Val Gly Arg Phe Asn Gly Ser Leu Arg Thr<br>465                 470                 475                 480 | | 1440 |
| gag cgc ctg aag atc cgc tgg cac acg tct gac aac cag aag ccc gtg<br>Glu Arg Leu Lys Ile Arg Trp His Thr Ser Asp Asn Gln Lys Pro Val<br>            485                 490                 495 | | 1488 |
| tcc cgg tgc tcg cgg cag tgc cag gag ggc cag gtg cgc cgg gtc aag<br>Ser Arg Cys Ser Arg Gln Cys Gln Glu Gly Gln Val Arg Arg Val Lys<br>        500                 505                 510 | | 1536 |
| ggg ttc cac tcc tgc tgc tac gac tgt gtg gac tgc gag gcg ggc agc<br>Gly Phe His Ser Cys Cys Tyr Asp Cys Val Asp Cys Glu Ala Gly Ser<br>        515                 520                 525 | | 1584 |
| tac cgg caa aac cca gac gac atc gcc tgc acc ttt tgt ggc cag gat<br>Tyr Arg Gln Asn Pro Asp Asp Ile Ala Cys Thr Phe Cys Gly Gln Asp<br>530                 535                 540 | | 1632 |
| gag tgg tcc ccg gag cga agc aca cgc tgc ttc cgc cgc agg tct cgg<br>Glu Trp Ser Pro Glu Arg Ser Thr Arg Cys Phe Arg Arg Arg Ser Arg<br>545                 550                 555                 560 | | 1680 |
| ttc ctg gca tgg ggc gag ccg gct gtg ctg ctg ctc ctg ctg<br>Phe Leu Ala Trp Gly Glu Pro Ala Val Leu Leu Leu Leu Leu Leu<br>                565                 570                 575 | | 1728 |
| agc ctg gcg ctg ggc ctt gtg ctg gct gct ttg ggg ctg ttc gtt cac<br>Ser Leu Ala Leu Gly Leu Val Leu Ala Ala Leu Gly Leu Phe Val His<br>        580                 585                 590 | | 1776 |
| cat cgg gac agc cca ctg gtt cag gcc tcg ggg ggc ccc ctg gcc tgc<br>His Arg Asp Ser Pro Leu Val Gln Ala Ser Gly Gly Pro Leu Ala Cys<br>            595                 600                 605 | | 1824 |
| ttt ggc ctg gtg tgc ctg ggc ctg gtc tgc ctc agc gtc ctc ctg ttc<br>Phe Gly Leu Val Cys Leu Gly Leu Val Cys Leu Ser Val Leu Leu Phe<br>610                 615                 620 | | 1872 |
| cct ggc cag ccc agc cct gcc cga tgc ctg gcc cag cag ccc ttg tcc<br>Pro Gly Gln Pro Ser Pro Ala Arg Cys Leu Ala Gln Gln Pro Leu Ser<br>625                 630                 635                 640 | | 1920 |
| cac ctc ccg ctc acg ggc tgc ctg agc aca ctc ttc ctg cag gcg gcc<br>His Leu Pro Leu Thr Gly Cys Leu Ser Thr Leu Phe Leu Gln Ala Ala<br>            645                 650                 655 | | 1968 |
| gag atc ttc gtg gag tca gaa ctg cct ctg agc tgg gca gac cgg ctg<br>Glu Ile Phe Val Glu Ser Glu Leu Pro Leu Ser Trp Ala Asp Arg Leu<br>        660                 665                 670 | | 2016 |
| agt ggc tgc ctg cgg ggg ccc tgg gcc tgg ctg gtg gtg ctg ctg gcc<br>Ser Gly Cys Leu Arg Gly Pro Trp Ala Trp Leu Val Val Leu Leu Ala<br>        675                 680                 685 | | 2064 |
| atg ctg gtg gag gtc gca ctg tgc acc tgg tac ctg gtg gcc ttc ccg<br>Met Leu Val Glu Val Ala Leu Cys Thr Trp Tyr Leu Val Ala Phe Pro<br>690                 695                 700 | | 2112 |
| ccg gag gtg gtg acg gac tgg cac atg ctg ccc acg gag gcg ctg gtg<br>Pro Glu Val Val Thr Asp Trp His Met Leu Pro Thr Glu Ala Leu Val<br>705                 710                 715                 720 | | 2160 |
| cac tgc cgc aca cgc tcc tgg gtc agc ttc ggc cta gcg cac gcc acc<br>His Cys Arg Thr Arg Ser Trp Val Ser Phe Gly Leu Ala His Ala Thr<br>            725                 730                 735 | | 2208 |

```
aat gcc acg ctg gcc ttt ctc tgc ttc ctg ggc act ttc ctg gtg cgg    2256
Asn Ala Thr Leu Ala Phe Leu Cys Phe Leu Gly Thr Phe Leu Val Arg
        740                 745                 750 agc cag ccg ggc cgc tac aac cgt gcc cgt ggc ctc acc ttt gcc atg    2304
Ser Gln Pro Gly Arg Tyr Asn Arg Ala Arg Gly Leu Thr Phe Ala Met
    755                 760                 765 ctg gcc tac ttc atc acc tgg gtc tcc ttt gtg ccc ctc ctg gcc aat    2352
Leu Ala Tyr Phe Ile Thr Trp Val Ser Phe Val Pro Leu Leu Ala Asn
770                 775                 780 gtg cag gtg gtc ctc agg ccc gcc gtg cag atg ggc gcc ctg ctc ctc    2400
Val Gln Val Val Leu Arg Pro Ala Val Gln Met Gly Ala Leu Leu Leu
785                 790                 795                 800 tgt gtc ctg ggc atc ctg gct gcc ttc cac ctg ccc agg tgt tac ctg    2448
Cys Val Leu Gly Ile Leu Ala Ala Phe His Leu Pro Arg Cys Tyr Leu
                805                 810                 815 ctc atg cgg cag cca ggg ctc aac acc ccc gag ttc ttc ctg gga ggg    2496
Leu Met Arg Gln Pro Gly Leu Asn Thr Pro Glu Phe Phe Leu Gly Gly
            820                 825                 830 ggc cct ggg gat gcc caa ggc cag aat gac ggg aac aca gga aat cag    2544
Gly Pro Gly Asp Ala Gln Gly Gln Asn Asp Gly Asn Thr Gly Asn Gln
        835                 840                 845 ggg aaa cat gag tga                                                 2559
Gly Lys His Glu
    850

<210> SEQ ID NO 10
<211> LENGTH: 852
<212> TYPE: PRT
<213> ORGANISM: human

<400> SEQUENCE: 10

Met Leu Gly Pro Ala Val Leu Gly Leu Ser Leu Trp Ala Leu Leu His
1               5                   10                  15

Pro Gly Thr Gly Ala Pro Leu Cys Leu Ser Gln Gln Leu Arg Met Lys
            20                  25                  30

Gly Asp Tyr Val Leu Gly Gly Leu Phe Pro Leu Gly Glu Ala Glu Glu
        35                  40                  45

Ala Gly Leu Arg Ser Arg Thr Arg Pro Ser Ser Pro Val Cys Thr Arg
    50                  55                  60

Phe Ser Ser Asn Gly Leu Leu Trp Ala Leu Ala Met Lys Met Ala Val
65                  70                  75                  80

Glu Glu Ile Asn Asn Lys Ser Asp Leu Leu Pro Gly Leu Arg Leu Gly
                85                  90                  95

Tyr Asp Leu Phe Asp Thr Cys Ser Glu Pro Val Val Ala Met Lys Pro
            100                 105                 110

Ser Leu Met Phe Leu Ala Lys Ala Gly Ser Arg Asp Ile Ala Ala Tyr
        115                 120                 125

Cys Asn Tyr Thr Gln Tyr Gln Pro Arg Val Leu Ala Val Ile Gly Pro
    130                 135                 140

His Ser Ser Glu Leu Ala Met Val Thr Gly Lys Phe Phe Ser Phe Phe
145                 150                 155                 160

Leu Met Pro Gln Val Ser Tyr Gly Ala Ser Met Glu Leu Leu Ser Ala
                165                 170                 175

Arg Glu Thr Phe Pro Ser Phe Phe Arg Thr Val Pro Ser Asp Arg Val
            180                 185                 190

Gln Leu Thr Ala Ala Ala Glu Leu Leu Gln Glu Phe Gly Trp Asn Trp
        195                 200                 205

Val Ala Ala Leu Gly Ser Asp Asp Glu Tyr Gly Arg Gln Gly Leu Ser
```

```
              210                 215                 220
Ile Phe Ser Ala Leu Ala Ala Arg Gly Ile Cys Ile Ala His Glu
225                 230                 235                 240

Gly Leu Val Pro Leu Pro Arg Ala Asp Asp Ser Arg Leu Gly Lys Val
                    245                 250                 255

Gln Asp Val Leu His Gln Val Asn Gln Ser Val Gln Val Val Leu
        260                 265                 270

Leu Phe Ala Ser Val His Ala Ala His Ala Leu Phe Asn Tyr Ser Ile
            275                 280                 285

Ser Ser Arg Leu Ser Pro Lys Val Trp Val Ala Ser Glu Ala Trp Leu
290                 295                 300

Thr Ser Asp Leu Val Met Gly Leu Pro Gly Met Ala Gln Met Gly Thr
305                 310                 315                 320

Val Leu Gly Phe Leu Gln Arg Gly Ala Gln Leu His Glu Phe Pro Gln
                325                 330                 335

Tyr Val Lys Thr His Leu Ala Leu Ala Thr Asp Pro Ala Phe Cys Ser
            340                 345                 350

Ala Leu Gly Glu Arg Glu Gln Gly Leu Glu Glu Asp Val Val Gly Gln
            355                 360                 365

Arg Cys Pro Gln Cys Asp Cys Ile Thr Leu Gln Asn Val Ser Ala Gly
    370                 375                 380

Leu Asn His His Gln Thr Phe Ser Val Tyr Ala Val Tyr Ser Val
385                 390                 395                 400

Ala Gln Ala Leu His Asn Thr Leu Gln Cys Asn Ala Ser Gly Cys Pro
                405                 410                 415

Ala Gln Asp Pro Val Lys Pro Trp Gln Leu Leu Glu Asn Met Tyr Asn
            420                 425                 430

Leu Thr Phe His Val Gly Gly Leu Pro Leu Arg Phe Asp Ser Ser Gly
            435                 440                 445

Asn Val Asp Met Glu Tyr Asp Leu Lys Leu Trp Val Trp Gln Gly Ser
    450                 455                 460

Val Pro Arg Leu His Asp Val Gly Arg Phe Asn Gly Ser Leu Arg Thr
465                 470                 475                 480

Glu Arg Leu Lys Ile Arg Trp His Thr Ser Asp Asn Gln Lys Pro Val
                485                 490                 495

Ser Arg Cys Ser Arg Gln Cys Gln Glu Gly Gln Val Arg Arg Val Lys
            500                 505                 510

Gly Phe His Ser Cys Cys Tyr Asp Cys Val Asp Cys Glu Ala Gly Ser
            515                 520                 525

Tyr Arg Gln Asn Pro Asp Asp Ile Ala Cys Thr Phe Cys Gly Gln Asp
    530                 535                 540

Glu Trp Ser Pro Glu Arg Ser Thr Arg Cys Phe Arg Arg Ser Arg
545                 550                 555                 560

Phe Leu Ala Trp Gly Glu Pro Ala Val Leu Leu Leu Leu Leu Leu
                565                 570                 575

Ser Leu Ala Leu Gly Leu Val Leu Ala Ala Leu Gly Leu Phe Val His
            580                 585                 590

His Arg Asp Ser Pro Leu Val Gln Ala Ser Gly Gly Pro Leu Ala Cys
        595                 600                 605

Phe Gly Leu Val Cys Leu Gly Leu Val Cys Leu Ser Val Leu Leu Phe
    610                 615                 620

Pro Gly Gln Pro Ser Pro Ala Arg Cys Leu Ala Gln Gln Pro Leu Ser
625                 630                 635                 640
```

```
His Leu Pro Leu Thr Gly Cys Leu Ser Thr Leu Phe Leu Gln Ala Ala
            645                 650                 655

Glu Ile Phe Val Glu Ser Glu Leu Pro Leu Ser Trp Ala Asp Arg Leu
            660                 665                 670

Ser Gly Cys Leu Arg Gly Pro Trp Ala Trp Leu Val Val Leu Leu Ala
            675                 680                 685

Met Leu Val Glu Val Ala Leu Cys Thr Trp Tyr Leu Val Ala Phe Pro
            690                 695                 700

Pro Glu Val Val Thr Asp Trp His Met Leu Pro Thr Glu Ala Leu Val
705                 710                 715                 720

His Cys Arg Thr Arg Ser Trp Val Ser Phe Gly Leu Ala His Ala Thr
            725                 730                 735

Asn Ala Thr Leu Ala Phe Leu Cys Phe Leu Gly Thr Phe Leu Val Arg
            740                 745                 750

Ser Gln Pro Gly Arg Tyr Asn Arg Ala Arg Gly Leu Thr Phe Ala Met
            755                 760                 765

Leu Ala Tyr Phe Ile Thr Trp Val Ser Phe Val Pro Leu Leu Ala Asn
            770                 775                 780

Val Gln Val Val Leu Arg Pro Ala Val Gln Met Gly Ala Leu Leu Leu
785                 790                 795                 800

Cys Val Leu Gly Ile Leu Ala Ala Phe His Leu Pro Arg Cys Tyr Leu
            805                 810                 815

Leu Met Arg Gln Pro Gly Leu Asn Thr Pro Glu Phe Phe Leu Gly Gly
            820                 825                 830

Gly Pro Gly Asp Ala Gln Gly Gln Asn Asp Gly Asn Thr Gly Asn Gln
            835                 840                 845

Gly Lys His Glu
    850

<210> SEQ ID NO 11
<211> LENGTH: 3237
<212> TYPE: DNA
<213> ORGANISM: human
<220> FEATURE:
<221> NAME/KEY: CDS
<222> LOCATION: (1)..(3237)

<400> SEQUENCE: 11 atg gca ttt tat agc tgc tgc tgg gtc ctc ttg gca ctc acc tgg cac      48
Met Ala Phe Tyr Ser Cys Cys Trp Val Leu Leu Ala Leu Thr Trp His
1               5                   10                  15 acc tct gcc tac ggg cca gac cag cga gcc caa aag aag ggg gac att      96
Thr Ser Ala Tyr Gly Pro Asp Gln Arg Ala Gln Lys Lys Gly Asp Ile
                20                  25                  30 atc ctt ggg ggg ctc ttt cct att cat ttt gga gta gca gct aaa gat      144
Ile Leu Gly Gly Leu Phe Pro Ile His Phe Gly Val Ala Ala Lys Asp
            35                  40                  45 caa gat ctc aaa tca agg ccg gag tct gtg gaa tgt atc agg tat aat      192
Gln Asp Leu Lys Ser Arg Pro Glu Ser Val Glu Cys Ile Arg Tyr Asn
        50                  55                  60 ttc cgt ggg ttt cgc tgg tta cag gct atg ata ttt gcc ata gag gag      240
Phe Arg Gly Phe Arg Trp Leu Gln Ala Met Ile Phe Ala Ile Glu Glu
65                  70                  75                  80 ata aac agc agc cca gcc ctt ctt ccc aac ttg acg ctg gga tac agg      288
Ile Asn Ser Ser Pro Ala Leu Leu Pro Asn Leu Thr Leu Gly Tyr Arg
                85                  90                  95 ata ttt gac act tgc aac acc gtt tct aag gcc ttg gaa gcc acc ctg      336
Ile Phe Asp Thr Cys Asn Thr Val Ser Lys Ala Leu Glu Ala Thr Leu
                100                 105                 110
```

```
agt ttt gtt gct caa aac aaa att gat tct ttg aac ctt gat gag ttc      384
Ser Phe Val Ala Gln Asn Lys Ile Asp Ser Leu Asn Leu Asp Glu Phe
        115                 120                 125 tgc aac tgc tca gag cac att ccc tct acg att gct gtg gtg gga gca      432
Cys Asn Cys Ser Glu His Ile Pro Ser Thr Ile Ala Val Val Gly Ala
130                 135                 140 act ggc tca ggc gtc tcc acg gca gtg gca aat ctg ctg ggg ctc ttc      480
Thr Gly Ser Gly Val Ser Thr Ala Val Ala Asn Leu Leu Gly Leu Phe
145                 150                 155                 160 tac att ccc cag gtc agt tat gcc tcc tcc agc aga ctc ctc agc aac      528
Tyr Ile Pro Gln Val Ser Tyr Ala Ser Ser Ser Arg Leu Leu Ser Asn
                165                 170                 175 aag aat caa ttc aag tct ttc ctc cga acc atc ccc aat gat gag cac      576
Lys Asn Gln Phe Lys Ser Phe Leu Arg Thr Ile Pro Asn Asp Glu His
            180                 185                 190 cag gcc act gcc atg gca gac atc atc gag tat ttc cgc tgg aac tgg      624
Gln Ala Thr Ala Met Ala Asp Ile Ile Glu Tyr Phe Arg Trp Asn Trp
        195                 200                 205 gtg ggc aca att gca gct gat gac gac tat ggg cgg ccg ggg att gag      672
Val Gly Thr Ile Ala Ala Asp Asp Asp Tyr Gly Arg Pro Gly Ile Glu
210                 215                 220 aaa ttc cga gag gaa gct gag gaa agg gat atc tgc atc gac ttc agt      720
Lys Phe Arg Glu Glu Ala Glu Glu Arg Asp Ile Cys Ile Asp Phe Ser
225                 230                 235                 240 gaa ctc atc tcc cag tac tct gat gag gaa gag atc cag cat gtg gta      768
Glu Leu Ile Ser Gln Tyr Ser Asp Glu Glu Glu Ile Gln His Val Val
                245                 250                 255 gag gtg att caa aat tcc acg gcc aaa gtc atc gtg gtt ttc tcc agt      816
Glu Val Ile Gln Asn Ser Thr Ala Lys Val Ile Val Val Phe Ser Ser
            260                 265                 270 ggc cca gat ctt gag ccc ctc atc aag gag att gtc cgg cgc aat atc      864
Gly Pro Asp Leu Glu Pro Leu Ile Lys Glu Ile Val Arg Arg Asn Ile
        275                 280                 285 acg ggc aag atc tgg ctg gcc agc gag gcc tgg gcc agc tcc tcc ctg      912
Thr Gly Lys Ile Trp Leu Ala Ser Glu Ala Trp Ala Ser Ser Ser Leu
290                 295                 300 atc gcc atg cct cag tac ttc cac gtg gtt ggc ggc acc att gga ttc      960
Ile Ala Met Pro Gln Tyr Phe His Val Val Gly Gly Thr Ile Gly Phe
305                 310                 315                 320 gct ctg aag gct ggg cag atc cca ggc ttc cgg gaa ttc ctg aag aag     1008
Ala Leu Lys Ala Gly Gln Ile Pro Gly Phe Arg Glu Phe Leu Lys Lys
                325                 330                 335 gtc cat ccc agg aag tct gtc cac aat ggt ttt gcc aag gag ttt tgg     1056
Val His Pro Arg Lys Ser Val His Asn Gly Phe Ala Lys Glu Phe Trp
            340                 345                 350 gaa gaa aca ttt aac tgc cac ctc caa gaa ggt gca aaa gga cct tta     1104
Glu Glu Thr Phe Asn Cys His Leu Gln Glu Gly Ala Lys Gly Pro Leu
        355                 360                 365 cct gtg gac acc ttt ctg aga ggt cac gaa gaa agt ggc gac agg ttt     1152
Pro Val Asp Thr Phe Leu Arg Gly His Glu Glu Ser Gly Asp Arg Phe
370                 375                 380 agc aac agc tcg aca gcc ttc cga ccc ctc tgt aca ggg gat gag aac     1200
Ser Asn Ser Ser Thr Ala Phe Arg Pro Leu Cys Thr Gly Asp Glu Asn
385                 390                 395                 400 atc agc agt gtc gag acc cct tac ata gat tac acg cat tta cgg ata     1248
Ile Ser Ser Val Glu Thr Pro Tyr Ile Asp Tyr Thr His Leu Arg Ile
                405                 410                 415 tcc tac aat gtg tac tta gca gtc tac tcc att gcc cac gcc ttg caa     1296
Ser Tyr Asn Val Tyr Leu Ala Val Tyr Ser Ile Ala His Ala Leu Gln
            420                 425                 430
```

```
gat ata tat acc tgc tta cct ggg aga ggg ctc ttc acc aat ggc tcc    1344
Asp Ile Tyr Thr Cys Leu Pro Gly Arg Gly Leu Phe Thr Asn Gly Ser
        435                 440                 445 tgt gca gac atc aag aaa gtt gag gcg tgg cag gtc ctg aag cac cta    1392
Cys Ala Asp Ile Lys Lys Val Glu Ala Trp Gln Val Leu Lys His Leu
450                 455                 460 cgg cat cta aac ttt aca aac aat atg ggg gag cag gtg acc ttt gat    1440
Arg His Leu Asn Phe Thr Asn Asn Met Gly Glu Gln Val Thr Phe Asp
465                 470                 475                 480 gag tgt ggt gac ctg gtg ggg aac tat tcc atc atc aac tgg cac ctc    1488
Glu Cys Gly Asp Leu Val Gly Asn Tyr Ser Ile Ile Asn Trp His Leu
                485                 490                 495 tcc cca gag gat ggc tcc atc gtg ttt aag gaa gtc ggg tat tac aac    1536
Ser Pro Glu Asp Gly Ser Ile Val Phe Lys Glu Val Gly Tyr Tyr Asn
                500                 505                 510 gtc tat gcc aag aag gga gaa aga ctc ttc atc aac gag gag aaa atc    1584
Val Tyr Ala Lys Lys Gly Glu Arg Leu Phe Ile Asn Glu Glu Lys Ile
            515                 520                 525 ctg tgg agt ggg ttc tcc agg gag gtg ccc ttc tcc aac tgc agc cga    1632
Leu Trp Ser Gly Phe Ser Arg Glu Val Pro Phe Ser Asn Cys Ser Arg
530                 535                 540 gac tgc ctg gca ggg acc agg aaa ggg atc att gag ggg gag ccc acc    1680
Asp Cys Leu Ala Gly Thr Arg Lys Gly Ile Ile Glu Gly Glu Pro Thr
545                 550                 555                 560 tgc tgc ttt gag tgt gtg gag tgt cct gat ggg gag tat agt gat gag    1728
Cys Cys Phe Glu Cys Val Glu Cys Pro Asp Gly Glu Tyr Ser Asp Glu
                565                 570                 575 aca gat gcc agt gcc tgt aac aag tgc cca gat gac ttc tgg tcc aat    1776
Thr Asp Ala Ser Ala Cys Asn Lys Cys Pro Asp Asp Phe Trp Ser Asn
                580                 585                 590 gag aac cac acc tcc tgc att gcc aag gag atc gag ttt ctg tcg tgg    1824
Glu Asn His Thr Ser Cys Ile Ala Lys Glu Ile Glu Phe Leu Ser Trp
            595                 600                 605 acg gag ccc ttt ggg atc gca ctc acc ctc ttt gcc gtg ctg ggc att    1872
Thr Glu Pro Phe Gly Ile Ala Leu Thr Leu Phe Ala Val Leu Gly Ile
610                 615                 620 ttc ctg aca gcc ttt gtg ctg ggt gtg ttt atc aag ttc cgc aac aca    1920
Phe Leu Thr Ala Phe Val Leu Gly Val Phe Ile Lys Phe Arg Asn Thr
625                 630                 635                 640 ccc att gtc aag gcc acc aac cga gag ctc tcc tac ctc ctc ctc ttc    1968
Pro Ile Val Lys Ala Thr Asn Arg Glu Leu Ser Tyr Leu Leu Leu Phe
                645                 650                 655 tcc ctg ctc tgc tgc ttc tcc agc tcc ctg ttc ttc atc ggg gag ccc    2016
Ser Leu Leu Cys Cys Phe Ser Ser Ser Leu Phe Phe Ile Gly Glu Pro
                660                 665                 670 cag gac tgg acg tgc cgc ctg cgc cag ccg gcc ttt ggc atc agc ttc    2064
Gln Asp Trp Thr Cys Arg Leu Arg Gln Pro Ala Phe Gly Ile Ser Phe
            675                 680                 685 gtg ctc tgc atc tca tgc atc ctg gtg aaa acc aac cgt gtc ctc ctg    2112
Val Leu Cys Ile Ser Cys Ile Leu Val Lys Thr Asn Arg Val Leu Leu
690                 695                 700 gtg ttt gag gcc aag atc ccc acc agc ttc cac cgc aag tgg tgg ggg    2160
Val Phe Glu Ala Lys Ile Pro Thr Ser Phe His Arg Lys Trp Trp Gly
705                 710                 715                 720 ctc aac ctg cag ttc ctg ctg gtt ttc ctc tgc acc ttc atg cag att    2208
Leu Asn Leu Gln Phe Leu Leu Val Phe Leu Cys Thr Phe Met Gln Ile
                725                 730                 735 gtc atc tgt gtg atc tgg ctc tac acc gcg ccc ccc tca agc tac cgc    2256
Val Ile Cys Val Ile Trp Leu Tyr Thr Ala Pro Pro Ser Ser Tyr Arg
                740                 745                 750
```

| | |
|---|---:|
| aac cag gag ctg gag gat gag atc atc ttc atc acg tgc cac gag ggc<br>Asn Gln Glu Leu Glu Asp Glu Ile Ile Phe Ile Thr Cys His Glu Gly<br>             755                 760                765 | 2304 |
| tcc ctc atg gcc ctg ggc ttc ctg atc ggc tac acc tgc ctg ctg gct<br>Ser Leu Met Ala Leu Gly Phe Leu Ile Gly Tyr Thr Cys Leu Leu Ala<br>770                   775                 780 | 2352 |
| gcc atc tgc ttc ttc ttt gcc ttc aag tcc cgg aag ctg ccg gag aac<br>Ala Ile Cys Phe Phe Phe Ala Phe Lys Ser Arg Lys Leu Pro Glu Asn<br>785                  790                795               800 | 2400 |
| ttc aat gaa gcc aag ttc atc acc ttc agc atg ctc atc ttc ttc atc<br>Phe Asn Glu Ala Lys Phe Ile Thr Phe Ser Met Leu Ile Phe Phe Ile<br>                     805                810               815 | 2448 |
| gtc tgg atc tcc ttc att cca gcc tat gcc agc acc tat ggc aag ttt<br>Val Trp Ile Ser Phe Ile Pro Ala Tyr Ala Ser Thr Tyr Gly Lys Phe<br>820                   825                 830 | 2496 |
| gtc tct gcc gta gag gtg att gcc atc ctg gca gcc agc ttt ggc ttg<br>Val Ser Ala Val Glu Val Ile Ala Ile Leu Ala Ala Ser Phe Gly Leu<br>             835                840               845 | 2544 |
| ctg gcg tgc atc ttc ttc aac aag atc tac atc att ctc ttc aag cca<br>Leu Ala Cys Ile Phe Phe Asn Lys Ile Tyr Ile Ile Leu Phe Lys Pro<br>850                   855                 860 | 2592 |
| tcc cgc aac acc atc gag gag gtg cgt tgc agc acc gca gct cac gct<br>Ser Arg Asn Thr Ile Glu Glu Val Arg Cys Ser Thr Ala Ala His Ala<br>865                  870                875               880 | 2640 |
| ttc aag gtg gct gcc cgg gcc acg ctg cgc cgc agc aac gtc tcc cgc<br>Phe Lys Val Ala Ala Arg Ala Thr Leu Arg Arg Ser Asn Val Ser Arg<br>                     885                890               895 | 2688 |
| aag cgg tcc agc agc ctt gga ggc tcc acg gga tcc acc ccc tcc tcc<br>Lys Arg Ser Ser Ser Leu Gly Gly Ser Thr Gly Ser Thr Pro Ser Ser<br>             900                905               910 | 2736 |
| tcc atc agc agc aag agc aac agc gaa gac cca ttc cca cag ccc gag<br>Ser Ile Ser Ser Lys Ser Asn Ser Glu Asp Pro Phe Pro Gln Pro Glu<br>                     915                920               925 | 2784 |
| agg cag aag cag cag cag ccg ctg gcc cta acc cag caa gag cag cag<br>Arg Gln Lys Gln Gln Gln Pro Leu Ala Leu Thr Gln Gln Glu Gln Gln<br>930                   935                 940 | 2832 |
| cag cag ccc ctg acc ctc cca cag cag caa cga tct cag cag cag ccc<br>Gln Gln Pro Leu Thr Leu Pro Gln Gln Gln Arg Ser Gln Gln Gln Pro<br>945                   950                955               960 | 2880 |
| aga tgc aag cag aag gtc atc ttt ggc agc ggc acg gtc acc ttc tca<br>Arg Cys Lys Gln Lys Val Ile Phe Gly Ser Gly Thr Val Thr Phe Ser<br>                     965                970               975 | 2928 |
| ctg agc ttt gat gag cct cag aag aac gcc atg gcc cac agg aat tct<br>Leu Ser Phe Asp Glu Pro Gln Lys Asn Ala Met Ala His Arg Asn Ser<br>980                   985                990 | 2976 |
| acg cac cag aac tcc ctg gag gcc cag aaa agc agc gat acg ctg acc<br>Thr His Gln Asn Ser Leu Glu Ala Gln Lys Ser Ser Asp Thr Leu Thr<br>             995                1000             1005 | 3024 |
| cga cac cag cca tta ctc ccg ctg cag tgc ggg gaa acg gac tta<br>Arg His Gln Pro Leu Leu Pro Leu Gln Cys Gly Glu Thr Asp Leu<br>1010                 1015               1020 | 3069 |
| gat ctg acc gtc cag gaa aca ggt ctg caa gga cct gtg ggt gga<br>Asp Leu Thr Val Gln Glu Thr Gly Leu Gln Gly Pro Val Gly Gly<br>1025                 1030               1035 | 3114 |
| gac cag cgg cca gag gtg gag gac cct gaa gag ttg tcc cca gca<br>Asp Gln Arg Pro Glu Val Glu Asp Pro Glu Glu Leu Ser Pro Ala<br>1040                 1045               1050 | 3159 |
| ctt gta gtg tcc agt tca cag agc ttt gtc atc agt ggt gga ggc<br>Leu Val Val Ser Ser Ser Gln Ser Phe Val Ile Ser Gly Gly Gly<br>1055                 1060               1065 | 3204 |

```
agc  act  gtt  aca  gaa  aac  gta  gtg  aat  tca  taa                       3237
Ser  Thr  Val  Thr  Glu  Asn  Val  Val  Asn  Ser
     1070                    1075

<210> SEQ ID NO 12
<211> LENGTH: 1078
<212> TYPE: PRT
<213> ORGANISM: human

<400> SEQUENCE: 12

Met Ala Phe Tyr Ser Cys Cys Trp Val Leu Leu Ala Leu Thr Trp His
1               5                   10                  15

Thr Ser Ala Tyr Gly Pro Asp Gln Arg Ala Gln Lys Lys Gly Asp Ile
            20                  25                  30

Ile Leu Gly Gly Leu Phe Pro Ile His Phe Gly Val Ala Ala Lys Asp
        35                  40                  45

Gln Asp Leu Lys Ser Arg Pro Glu Ser Val Glu Cys Ile Arg Tyr Asn
    50                  55                  60

Phe Arg Gly Phe Arg Trp Leu Gln Ala Met Ile Phe Ala Ile Glu Glu
65                  70                  75                  80

Ile Asn Ser Ser Pro Ala Leu Leu Pro Asn Leu Thr Leu Gly Tyr Arg
                85                  90                  95

Ile Phe Asp Thr Cys Asn Thr Val Ser Lys Ala Leu Glu Ala Thr Leu
            100                 105                 110

Ser Phe Val Ala Gln Asn Lys Ile Asp Ser Leu Asn Leu Asp Glu Phe
        115                 120                 125

Cys Asn Cys Ser Glu His Ile Pro Ser Thr Ile Ala Val Val Gly Ala
    130                 135                 140

Thr Gly Ser Gly Val Ser Thr Ala Val Ala Asn Leu Leu Gly Leu Phe
145                 150                 155                 160

Tyr Ile Pro Gln Val Ser Tyr Ala Ser Ser Arg Leu Leu Ser Asn
                165                 170                 175

Lys Asn Gln Phe Lys Ser Phe Leu Arg Thr Ile Pro Asn Asp Glu His
            180                 185                 190

Gln Ala Thr Ala Met Ala Asp Ile Ile Glu Tyr Phe Arg Trp Asn Trp
        195                 200                 205

Val Gly Thr Ile Ala Ala Asp Asp Asp Tyr Gly Arg Pro Gly Ile Glu
    210                 215                 220

Lys Phe Arg Glu Glu Ala Glu Glu Arg Asp Ile Cys Ile Asp Phe Ser
225                 230                 235                 240

Glu Leu Ile Ser Gln Tyr Ser Asp Glu Glu Ile Gln His Val Val
                245                 250                 255

Glu Val Ile Gln Asn Ser Thr Ala Lys Val Ile Val Phe Ser Ser
            260                 265                 270

Gly Pro Asp Leu Glu Pro Leu Ile Lys Glu Ile Val Arg Arg Asn Ile
        275                 280                 285

Thr Gly Lys Ile Trp Leu Ala Ser Glu Ala Trp Ala Ser Ser Ser Leu
    290                 295                 300

Ile Ala Met Pro Gln Tyr Phe His Val Val Gly Thr Ile Gly Phe
305                 310                 315                 320

Ala Leu Lys Ala Gly Gln Ile Pro Gly Phe Arg Glu Phe Leu Lys Lys
                325                 330                 335

Val His Pro Arg Lys Ser Val His Asn Gly Phe Ala Lys Glu Phe Trp
            340                 345                 350

Glu Glu Thr Phe Asn Cys His Leu Gln Glu Gly Ala Lys Gly Pro Leu
```

-continued

```
              355                 360                 365
    Pro Val Asp Thr Phe Leu Arg Gly His Glu Glu Ser Gly Asp Arg Phe
    370                 375                 380

Ser Asn Ser Ser Thr Ala Phe Arg Pro Leu Cys Thr Gly Asp Glu Asn
    385                 390                 395                 400

Ile Ser Ser Val Glu Thr Pro Tyr Ile Asp Tyr Thr His Leu Arg Ile
                        405                 410                 415

Ser Tyr Asn Val Tyr Leu Ala Val Tyr Ser Ile Ala His Ala Leu Gln
                    420                 425                 430

Asp Ile Tyr Thr Cys Leu Pro Gly Arg Gly Leu Phe Thr Asn Gly Ser
                435                 440                 445

Cys Ala Asp Ile Lys Lys Val Glu Ala Trp Gln Val Leu Lys His Leu
    450                 455                 460

Arg His Leu Asn Phe Thr Asn Asn Met Gly Glu Gln Val Thr Phe Asp
    465                 470                 475                 480

Glu Cys Gly Asp Leu Val Gly Asn Tyr Ser Ile Ile Asn Trp His Leu
                        485                 490                 495

Ser Pro Glu Asp Gly Ser Ile Val Phe Lys Glu Val Gly Tyr Tyr Asn
                    500                 505                 510

Val Tyr Ala Lys Lys Gly Glu Arg Leu Phe Ile Asn Glu Glu Lys Ile
                515                 520                 525

Leu Trp Ser Gly Phe Ser Arg Glu Val Pro Phe Ser Asn Cys Ser Arg
    530                 535                 540

Asp Cys Leu Ala Gly Thr Arg Lys Gly Ile Ile Glu Gly Glu Pro Thr
    545                 550                 555                 560

Cys Cys Phe Glu Cys Val Glu Cys Pro Asp Gly Glu Tyr Ser Asp Glu
                        565                 570                 575

Thr Asp Ala Ser Ala Cys Asn Lys Cys Pro Asp Asp Phe Trp Ser Asn
                    580                 585                 590

Glu Asn His Thr Ser Cys Ile Ala Lys Glu Ile Glu Phe Leu Ser Trp
                595                 600                 605

Thr Glu Pro Phe Gly Ile Ala Leu Thr Leu Phe Ala Val Leu Gly Ile
    610                 615                 620

Phe Leu Thr Ala Phe Val Leu Gly Val Phe Ile Lys Phe Arg Asn Thr
    625                 630                 635                 640

Pro Ile Val Lys Ala Thr Asn Arg Glu Leu Ser Tyr Leu Leu Leu Phe
                        645                 650                 655

Ser Leu Leu Cys Cys Phe Ser Ser Ser Leu Phe Phe Ile Gly Glu Pro
                    660                 665                 670

Gln Asp Trp Thr Cys Arg Leu Arg Gln Pro Ala Phe Gly Ile Ser Phe
                675                 680                 685

Val Leu Cys Ile Ser Cys Ile Leu Val Lys Thr Asn Arg Val Leu Leu
    690                 695                 700

Val Phe Glu Ala Lys Ile Pro Thr Ser Phe His Arg Lys Trp Trp Gly
    705                 710                 715                 720

Leu Asn Leu Gln Phe Leu Leu Val Phe Leu Cys Thr Phe Met Gln Ile
                        725                 730                 735

Val Ile Cys Val Ile Trp Leu Tyr Thr Ala Pro Pro Ser Ser Tyr Arg
                    740                 745                 750

Asn Gln Glu Leu Glu Asp Glu Ile Ile Phe Ile Thr Cys His Glu Gly
                755                 760                 765

Ser Leu Met Ala Leu Gly Phe Leu Ile Gly Tyr Thr Cys Leu Leu Ala
    770                 775                 780
```

-continued

Ala Ile Cys Phe Phe Phe Ala Phe Lys Ser Arg Lys Leu Pro Glu Asn
785                 790                 795                 800

Phe Asn Glu Ala Lys Phe Ile Thr Phe Ser Met Leu Ile Phe Phe Ile
                805                 810                 815

Val Trp Ile Ser Phe Ile Pro Ala Tyr Ala Ser Thr Tyr Gly Lys Phe
            820                 825                 830

Val Ser Ala Val Glu Val Ile Ala Ile Leu Ala Ala Ser Phe Gly Leu
        835                 840                 845

Leu Ala Cys Ile Phe Phe Asn Lys Ile Tyr Ile Ile Leu Phe Lys Pro
850                 855                 860

Ser Arg Asn Thr Ile Glu Glu Val Arg Cys Ser Thr Ala Ala His Ala
865                 870                 875                 880

Phe Lys Val Ala Ala Arg Ala Thr Leu Arg Arg Ser Asn Val Ser Arg
                885                 890                 895

Lys Arg Ser Ser Ser Leu Gly Gly Ser Thr Gly Ser Thr Pro Ser Ser
            900                 905                 910

Ser Ile Ser Ser Lys Ser Asn Ser Glu Asp Pro Phe Gln Pro Gln Glu
        915                 920                 925

Arg Gln Lys Gln Gln Gln Pro Leu Ala Leu Thr Gln Gln Glu Gln Gln
    930                 935                 940

Gln Gln Pro Leu Thr Leu Pro Gln Gln Arg Ser Gln Gln Gln Pro
945                 950                 955                 960

Arg Cys Lys Gln Lys Val Ile Phe Gly Ser Gly Thr Val Thr Phe Ser
                965                 970                 975

Leu Ser Phe Asp Glu Pro Gln Lys Asn Ala Met Ala His Arg Asn Ser
            980                 985                 990

Thr His Gln Asn Ser Leu Glu Ala Gln Lys Ser Ser Asp Thr Leu Thr
        995                 1000                1005

Arg His Gln Pro Leu Leu Pro Leu Gln Cys Gly Glu Thr Asp Leu
    1010                1015                1020

Asp Leu Thr Val Gln Glu Thr Gly Leu Gln Gly Pro Val Gly Gly
1025                1030                1035

Asp Gln Arg Pro Glu Val Glu Asp Pro Glu Glu Leu Ser Pro Ala
    1040                1045                1050

Leu Val Val Ser Ser Ser Gln Ser Phe Val Ile Ser Gly Gly Gly
1055                1060                1065

Ser Thr Val Thr Glu Asn Val Val Asn Ser
    1070                1075

<210> SEQ ID NO 13
<211> LENGTH: 28
<212> TYPE: DNA
<213> ORGANISM: artificial
<220> FEATURE:
<223> OTHER INFORMATION: Primer sequence

<400> SEQUENCE: 13
caccaagctt atggcatttt atagctgc                                              28

<210> SEQ ID NO 14
<211> LENGTH: 28
<212> TYPE: DNA
<213> ORGANISM: artificial
<220> FEATURE:
<223> OTHER INFORMATION: Primer sequence

<400> SEQUENCE: 14
atatcgtacg cttggcaatg caggaggt                                              28

```
<210> SEQ ID NO 15
<211> LENGTH: 28
<212> TYPE: DNA
<213> ORGANISM: artificial
<220> FEATURE:
<223> OTHER INFORMATION: Primer sequence

<400> SEQUENCE: 15
atatcgtacg gtgtttttgg ctttgcgt                                              28

<210> SEQ ID NO 16
<211> LENGTH: 31
<212> TYPE: DNA
<213> ORGANISM: artificial
<220> FEATURE:
<223> OTHER INFORMATION: Primer sequence

<400> SEQUENCE: 16
atatgcggcc gcaggtggag ccgcagcgcc t                                          31

<210> SEQ ID NO 17
<211> LENGTH: 28
<212> TYPE: DNA
<213> ORGANISM: artificial
<220> FEATURE:
<223> OTHER INFORMATION: Primer sequence

<400> SEQUENCE: 17
atatcgtacg cggttcctgg catggggc                                              28

<210> SEQ ID NO 18
<211> LENGTH: 31
<212> TYPE: DNA
<213> ORGANISM: artificial
<220> FEATURE:
<223> OTHER INFORMATION: Primer sequence

<400> SEQUENCE: 18
atatgcggcc gcactcatgt ttcccctgat t                                          31
```